(12) United States Patent
Kshirsagar et al.

(10) Patent No.: US 8,143,270 B2
(45) Date of Patent: Mar. 27, 2012

(54) 2-AMINO 1H-IN-IMIDAZO RING SYSTEMS AND METHODS

(75) Inventors: Tushar A. Kshirsagar, Woodbury, MN (US); Scott E. Langer, Woodbury, MN (US); Shri Niwas, Maple Grove, MN (US); Philip D. Heppner, Forest Lake, MN (US); David T. Amos, Forest Lake, MN (US)

(73) Assignee: 3M Innovative Properties Company, St. Pau, MN (US)

( * ) Notice: Subject to any disclaimer, the term of this patent is extended or adjusted under 35 U.S.C. 154(b) by 1025 days.

(21) Appl. No.: 11/574,460

(22) PCT Filed: Sep. 1, 2005

(86) PCT No.: PCT/US2005/031616
§ 371 (c)(1),
(2), (4) Date: Feb. 28, 2007

(87) PCT Pub. No.: WO2006/029115
PCT Pub. Date: Mar. 16, 2006

(65) Prior Publication Data
US 2009/0023720 A1    Jan. 22, 2009

Related U.S. Application Data

(60) Provisional application No. 60/606,607, filed on Sep. 2, 2004.

(51) Int. Cl.
C07D 471/04 (2006.01)
A61K 31/437 (2006.01)

(52) U.S. Cl. .......................... 514/293; 546/82
(58) Field of Classification Search .................. 546/82; 514/293
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria et al. |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 02/36592 | 5/2002 |
| WO | WO 2005/018551 | 3/2005 |
| WO | WO 2005/018555 | 3/2005 |
| WO | WO 2005/018556 | 3/2005 |

(Continued)

OTHER PUBLICATIONS

Wozniak et al., "The Amination of 3-nitro-1, 5-naphthyridines by Liquid Ammonia/Potassium Permanganate [1,2]. A New and Convenient Amination Method", *Journal of the Royal Netherlands Chemical Society*, 102, pp. 511-513, Dec. 12, 1983.

(Continued)

*Primary Examiner* — Rita Desai

(57) ABSTRACT

1H-Imidazo ring systems (e.g., imidazopyridines, imidazoquinolines, imidazonaphthyridines, 6,7,8,9-tetrahydro imidazoquinolines and imidazonaphthyridines) with an amino substituent at the 2-position, pharmaceutical compositions containing these compounds, methods of making the compounds, intermediates, and methods of use of these compounds as immunomodulators, for modulating cytokine biosynthesis in animals and in the treatment of diseases including viral and neoplastic diseases, are disclosed.

19 Claims, No Drawings

U.S. PATENT DOCUMENTS

| | | |
|---|---|---|
| 6,706,728 B2 | 3/2004 | Hedenstrom et al. |
| 6,743,920 B2 | 6/2004 | Lindstrom et al. |
| 6,756,382 B2 | 6/2004 | Coleman et al. |
| 6,797,718 B2 | 9/2004 | Dellaria et al. |
| 6,818,650 B2 | 11/2004 | Griesgraber |
| 6,841,678 B2 | 1/2005 | Merli et al. |
| 6,852,861 B2 | 2/2005 | Merli et al. |
| 7,163,947 B2 | 1/2007 | Griesgraber et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2003/0096835 A1 | 5/2003 | Crooks et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0144286 A1 | 7/2003 | Frenkel et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0214851 A1 | 10/2004 | Birmachu et al. |
| 2005/0054590 A1 | 3/2005 | Averett |
| 2005/0085500 A1 | 4/2005 | Gutman et al. |
| 2005/0165236 A1 | 7/2005 | Colombo et al. |
| 2005/0245562 A1 | 11/2005 | Garcia-Echeverria et al. |

FOREIGN PATENT DOCUMENTS

| | | |
|---|---|---|
| WO | WO 2005/020999 | 3/2005 |
| WO | WO 2005/032484 | 4/2005 |
| WO | WO 2005/048933 | 6/2005 |
| WO | WO 2005/048945 | 6/2005 |
| WO | WO 2005/051317 | 6/2005 |
| WO | WO 2005/051324 | 6/2005 |
| WO | WO 2005/054237 | 6/2005 |
| WO | WO 2005/054238 | 6/2005 |
| WO | WO 2005/066169 | 7/2005 |
| WO | WO 2005/066170 | 7/2005 |
| WO | WO 2005/066172 | 7/2005 |
| WO | WO 2005/076783 | 8/2005 |
| WO | WO 2005/079195 | 9/2005 |
| WO | WO 2005/094531 | 10/2005 |
| WO | WO 2005/123079 | 12/2005 |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO 2006/065280 | 6/2006 |
| WO | WO 2006/074003 | 7/2006 |
| WO | WO 2006/074046 | 7/2006 |
| WO | WO 2006/004737 | 8/2006 |
| WO | WO 2006/083400 | 8/2006 |
| WO | WO 2006/083440 | 8/2006 |
| WO | WO 2006/086449 | 8/2006 |
| WO | WO 2006/086633 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO 2006/098852 | 9/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO 2007/028129 | 3/2007 |
| WO | WO 2007/030775 | 3/2007 |
| WO | WO 2007/030777 | 3/2007 |
| WO | WO 2007/035935 | 3/2007 |
| WO | WO 2007/056112 | 5/2007 |

OTHER PUBLICATIONS

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.*, 15, pp. 1278-1284 (1950).

Jain et al., "Chemical and Pharmacological Investigation sof Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", *Chem. Abs.* 85, 94362, (1976).

Berényi et al., "Ring Transformation of Condensed Dihydro-astriazines.", *J. Heterocyclic Chem.*, 18, pp. 1537-1540 (1981).

Chollet et al., "Development of a Topically Active Imiquimiod Formulation.", *Pharmaceutical Development and Technology*, 4(1), pp. 35-43 (1999).

Izumi et al., "1*H*-Imidazo[4,5-*c*]quinoline Derivatives as Novel Potent TNF-α Suppressors: Synthesis and Structure-Activity Relationship of 1-, 2- and 4-Substituted 1*H*-imidazo[4,5-*c*]pyridines.", *Bioorganic & Medicinal Chemistry*, 11, pp. 2541-2550 (2003).

Patani, G.A. et al., Bioisosterism: A Rational Approach in Drug Design, *Chemical Reviews*, vol. 96, (1996) p. 3147-3176.

2-AMINO 1H-IN-IMIDAZO RING SYSTEMS AND METHODS

RELATED APPLICATIONS

This application is the National Stage of International Application No. PCT/US2005/031616, filed Sep. 1, 2005, which claims priority to U.S. Provisional Application Ser. No. 60/606,607, filed Sep. 2, 2004, which is incorporated herein by reference in its entirety.

BACKGROUND

Certain compounds have been found to be useful as immune response modifiers (IRMs), rendering them useful in the treatment of a variety of disorders. There continues to be interest in and a need for compounds that have the ability to modulate the immune response, by induction of cytokine biosynthesis or other mechanisms.

SUMMARY OF THE INVENTION

It has now been found that certain 2-amino 1H-imidazo ring systems modulate cytokine biosynthesis. In one aspect, the present invention provides compounds of the Formula I:

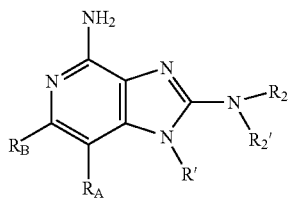

I and more specifically the following compounds of the Formulas II, III, IV, V, VI, VII, and VIII:

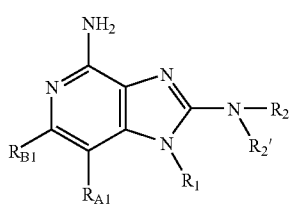

II

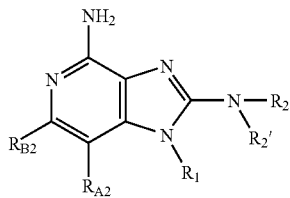

III

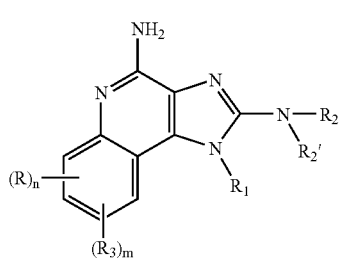

IV

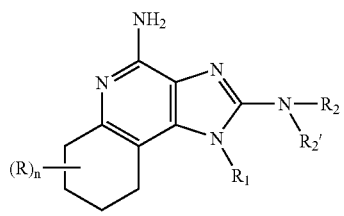

V

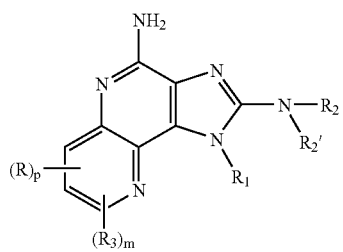

VI

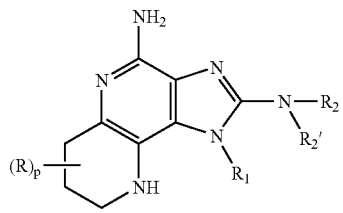

VII

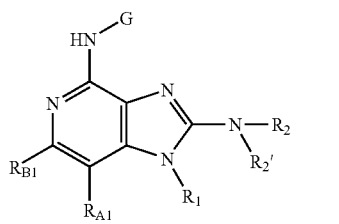

VIII wherein R, R', $R_1$, $R_2$, $R_2'$, $R_3$, $R_4$, $R_B$, $R_{A1}$, $R_{B1}$, $R_{A2}$, $R_{B2}$, G, m, n, and p are as defined below; and pharmaceutically acceptable salts thereof.

The compounds of Formulas I, II, III, IV, V, VI, VII, and VIII are useful as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested per the test procedures described in the Examples Section. Compounds can be tested for induction of cytokine biosynthesis by incubating human peripheral blood mononuclear cells (PBMC) in a culture with the compound(s) at a concentration range of 30 to 0.014 μM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 μM and analyzing for tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing the immune response modifier compounds, and methods of inducing cytokine biosynthesis in animal cells, treating a viral disease in an animal, and/or treating a neoplastic disease in an animal by administering to the animal one or more compounds of the Formulas I, II, III, IV, V, VI, VII, and/or VIII, and/or pharmaceutically acceptable salts thereof.

In another aspect, the invention provides methods of synthesizing the compounds of Formulas I, II, III, IV, V, VI, VII, and VIII and intermediate compounds useful in the synthesis of these compounds.

As used herein, "a", "an", "the", "at least one", and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

The present invention provides compounds of the following Formulas I through VII:

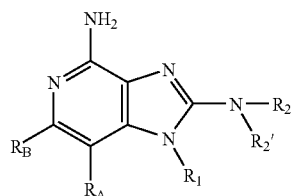

I

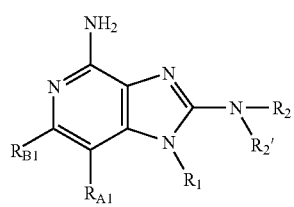

II

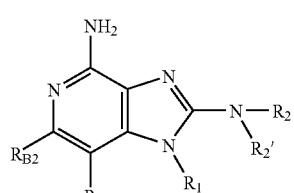

III

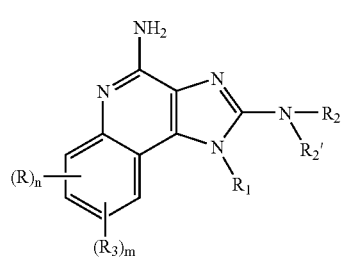

IV

-continued

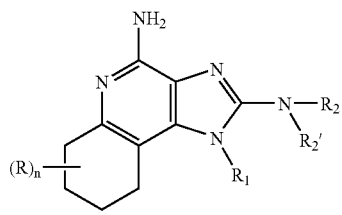

V

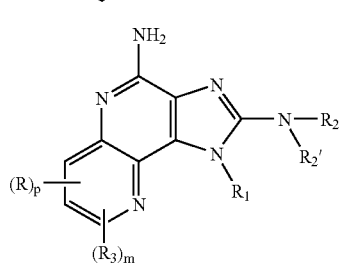

VI

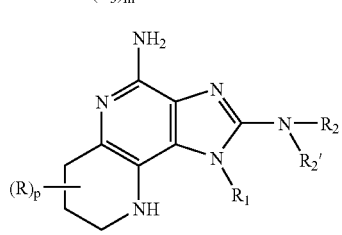

VII

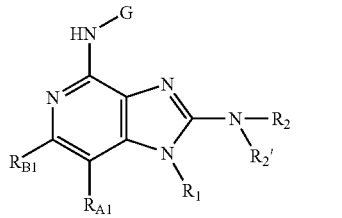

VIII and intermediates of the following Formulas IX, X, XI, and XII:

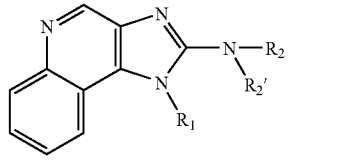

IX

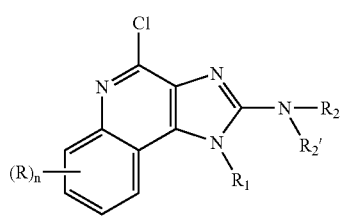

X

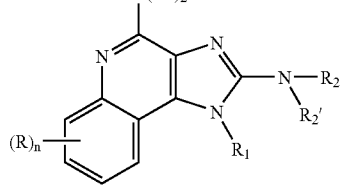

XI

-continued

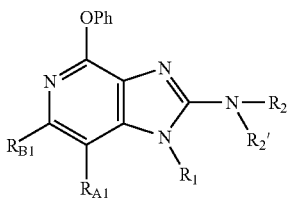

wherein R, R', R₁, R₂, R₂', R₃, R$_A$, R$_B$, R$_{A1}$, R$_{B1}$, R$_{A2}$, R$_{B2}$, G, m, n, and p are as defined below; and pharmaceutically acceptable salts thereof.

In one embodiment, the present invention provides a compound of the following Formula I:

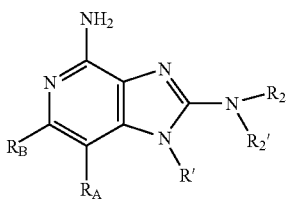

wherein:

R₂ is selected from the group consisting of:
—R$_{4a}$,
-Q$_a$-R$_{4a}$,
—X₂—R$_{5a}$, and
—X₂—N(R$_{8a}$)-Q$_a$-R$_{4a}$;

R₂' is selected from the group consisting of hydrogen, C$_{1-4}$ alkyl, hydroxyC$_{2-4}$ alkylenyl, and alkoxyC$_{2-4}$ alkylenyl;

Q$_a$ is selected from the group consisting of a bond, —C(R₆)—, —C(R₆)—C(R₆)—, —S(O)₂—, —C(R₆)—N(R$_{8a}$)—W—, —S(O)₂—N(R$_{8a}$)—, and —C(R₆)—O—;

X₂ is selected from the group consisting of C$_{2-4}$ alkylene and C$_{2-4}$ alkenylene;

R$_{4a}$ is selected from the group consisting of hydrogen, C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl wherein the C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl groups are unsubstituted or substituted by one or more substituents independently selected from the group consisting of C$_{1-4}$ alkyl, C$_{1-4}$ alkoxy, C$_{1-4}$ alkanoyl, C$_{1-4}$ alkoxycarbonyl, hydroxyC$_{1-4}$ alkyl, haloC$_{1-4}$ alkyl, haloC$_{1-4}$ alkoxy, halogen, nitro, hydroxy, mercapto, cyano, amino, C$_{1-4}$ alkylamino, di(C$_{1-4}$ alkyl)amino, and in the case of C$_{1-4}$ alkyl, C$_{2-4}$ alkenyl, C$_{2-4}$ alkynyl, and heterocyclyl, oxo;

R$_{5a}$ is selected from the group consisting of:

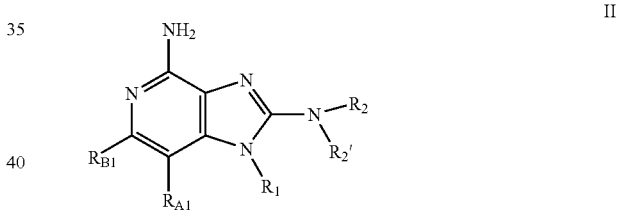

R$_{7a}$ is C$_{2-4}$ alkylene;
R$_{8a}$ is selected from the group consisting of hydrogen and C$_{1-4}$ alkyl;

R$_A$ and R$_B$ are independently selected from the group consisting of:
hydrogen,
halogen,
alkyl,
alkenyl,
alkoxy,
alkylthio, and
—N(R₉)₂;

or R$_A$ and R$_B$ taken together form a fused benzene ring or a fused pyridine ring wherein the benzene ring or pyridine ring is unsubstituted or substituted by one or more R''' groups;

or R$_A$ and R$_B$ taken together form a fused 5 to 7 membered saturated ring optionally containing one nitrogen atom wherein the ring is unsubstituted or substituted by one or more R groups;

R is selected from the group consisting of halogen, hydroxy, alkyl, alkenyl, haloalkyl, alkoxy, alkylthio, and —N(R₉)₂;

R' is selected from the group consisting of hydrogen and a non-interfering substituent;

R''' is a non-interfering substituent;

W is selected from the group consisting of a bond, —C(O)—, and —S(O)₂—;

R₆ is selected from the group consisting of =O and =S; and

R₉ is selected from the group consisting of hydrogen and alkyl;

or a pharmaceutically acceptable salt thereof.

In one embodiment, the present invention provides a compound of the following Formula II:

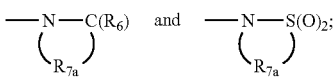

wherein:

R₂ is selected from the group consisting of:
—R$_{4a}$,
-Q$_a$-R$_{4a}$,
—X₂—R$_{5a}$, and
—X₂—N(R$_{8a}$)-Q$_a$-R$_{4a}$;

R₂' is selected from the group consisting of hydrogen, C$_{1-4}$ alkyl, hydroxyC$_{2-4}$ alkylenyl, and alkoxyC$_{2-4}$ alkylenyl;

Q$_a$ is selected from the group consisting of a bond, —C(R₆)—, —C(R₆)—C(R₆)—, —S(O)₂—, —C(R₆)—N(R$_{8a}$)—W—, —S(O)₂—N(R$_{8a}$)—, and —C(R₆)—O—;

X₂ is selected from the group consisting of C$_{2-4}$ alkylene and C$_{2-4}$ alkenylene;

R$_{4a}$ is selected from the group consisting of hydrogen, C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl wherein the C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl groups are unsubstituted or substituted by one or more substituents independently selected from the group consisting of $C_{1-4}$ alkyl, $C_{1-4}$ alkoxy, $C_{1-4}$ alkanoyl, $C_{1-4}$ alkoxycarbonyl, hydroxy$C_{1-4}$ alkyl, halo$C_{1-4}$ alkyl, halo$C_{1-4}$ alkoxy, halogen, nitro, hydroxy, mercapto, cyano, amino, $C_{1-4}$ alkylamino, di($C_{1-4}$ alkyl)amino, and in the case of $C_{1-4}$ alkyl, $C_{2-4}$ alkenyl, $C_{2-4}$ alkynyl, and heterocyclyl, oxo;

$R_{5a}$ is selected from the group consisting of:

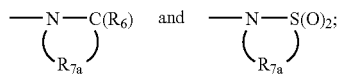

$R_{7a}$ is $C_{2-4}$ alkylene;
$R_{8a}$ is selected from the group consisting of hydrogen and $C_{1-4}$ alkyl;
$R_{A1}$ and $R_{B1}$ are independently selected from the group consisting of:
hydrogen,
halogen,
alkyl,
alkenyl,
alkoxy,
alkylthio, and
—N(R$_9$)$_2$;
or $R_{A1}$ and $R_{B1}$ taken together form a fused benzene ring or a fused pyridine ring wherein the benzene ring or pyridine ring is unsubstituted or substituted by one $R_3$ group, or substituted by one $R_3$ group and one R group, or substituted by one or more R groups;
or $R_{A1}$ and $R_{B1}$ taken together form a fused 5 to 7 membered saturated ring optionally containing one nitrogen atom wherein the ring is unsubstituted or substituted by one or more R groups;
R is selected from the group consisting of halogen, hydroxy, alkyl, alkenyl, haloalkyl, alkoxy, alkylthio, and —N(R$_9$)$_2$;
$R_1$ is selected from the group consisting of:
—$R_4$,
—$X_1$—$R_4$,
—$X_1$—$Y_1$—$R_4$,
—$X_1$—$Y_1$—$X_1$—$Y_1$—$R_4$, and
—$X_1$—$R_5$;
$R_3$ is selected from the group consisting of:
—Z—$R_4$,
—Z—X—$R_4$,
—Z—X—Y—$R_4$, and
—Z—X—$R_5$;
X and $X_1$ are independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;
Y and $Y_1$ are independently selected from the group consisting of:

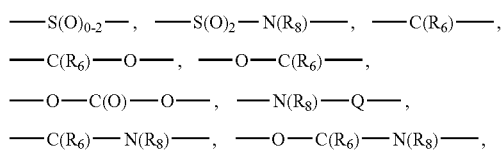

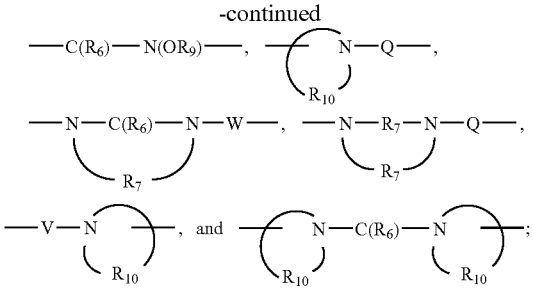

Z is selected from the group consisting of a bond and —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;
$R_5$ is selected from the group consisting of:

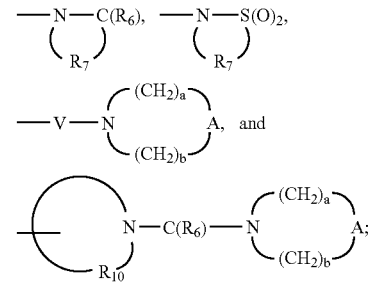

A is selected from the group consisting of —O—, —C(O)—, —S(O)$_{0-2}$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—;
a and b are independently integers from 1 to 6 with the proviso that a+b is ≤7;
$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl; and
$R_{10}$ is $C_{3-8}$ alkylene;
or a pharmaceutically acceptable salt thereof.

In one embodiment, the present invention provides a compound of the following Formula III:

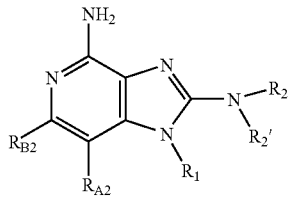

wherein:

$R_2$ is selected from the group consisting of:
- $-R_{4a}$,
- $-Q_a$-$R_{4a}$,
- $-X_2-R_{5a}$, and
- $-X_2-N(R_{8a})$-$Q_a$-$R_{4a}$;

$R_2'$ is selected from the group consisting of hydrogen, $C_{1-4}$ alkyl, hydroxy$C_{2-4}$ alkylenyl, and alkoxy$C_{2-4}$ alkylenyl;

$Q_a$ is selected from the group consisting of a bond, $-C(R_6)-$, $-C(R_6)-C(R_6)-$, $-S(O)_2-$, $-C(R_6)-N(R_{8a})-W-$, $-S(O)_2-N(R_{8a})-$, and $-C(R_6)-O-$;

$X_2$ is selected from the group consisting of $C_{2-4}$ alkylene and $C_{2-4}$ alkenylene;

$R_{4a}$ is selected from the group consisting of hydrogen, $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl wherein the $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl groups are unsubstituted or substituted by one or more substituents independently selected from the group consisting of $C_{1-4}$ alkyl, $C_{1-4}$ alkoxy, $C_{1-4}$ alkanoyl, $C_{1-4}$ alkoxycarbonyl, hydroxy$C_{1-4}$ alkyl, halo$C_{1-4}$ alkyl, halo$C_{1-4}$ alkoxy, halogen, nitro, hydroxy, mercapto, cyano, amino, $C_{1-4}$ alkylamino, di($C_{1-4}$ alkyl)amino, and in the case of $C_{1-4}$ alkyl, $C_{2-4}$ alkenyl, $C_{2-4}$ alkynyl, and heterocyclyl, oxo;

$R_{5a}$ is selected from the group consisting of:

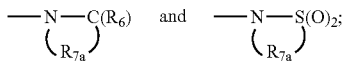

$R_{7a}$ is $C_{2-4}$ alkylene;
$R_{8a}$ is selected from the group consisting of hydrogen and $C_{1-4}$ alkyl;
$R_{A2}$ and $R_{B2}$ are independently selected from the group consisting of:
hydrogen,
halogen,
alkyl,
alkenyl,
alkoxy,
alkylthio, and
$-N(R_9)_2$;

$R_1$ is selected from the group consisting of:
- $-R_4$,
- $-X_1-R_4$,
- $-X_1-Y_1-R_4$,
- $-X_1-Y_1-X_1-Y_1-R_4$, and
- $-X_1-R_5$;

$X_1$ is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$Y_1$ is selected from the group consisting of:

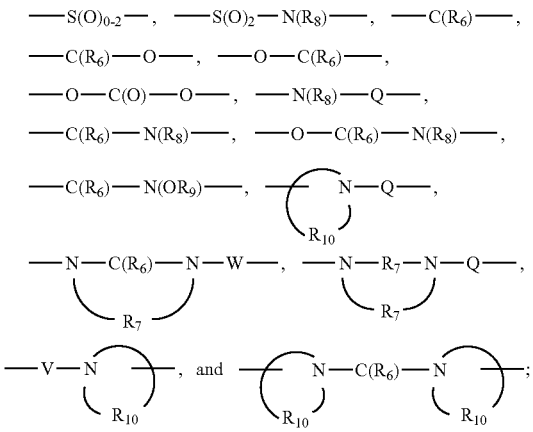

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

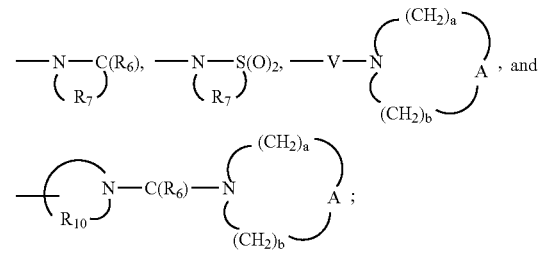

A is selected from the group consisting of —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≦7;

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl; and
$R_{10}$ is $C_{3-8}$ alkylene;
or a pharmaceutically acceptable salt thereof.

In one embodiment, the present invention provides a compound of the following Formula IV:

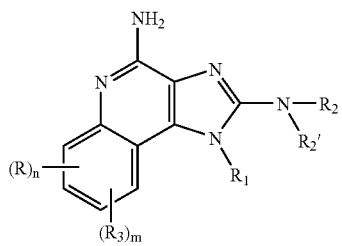

wherein:
$R_2$ is selected from the group consisting of:
—$R_{4a}$,
-$Q_a$-$R_{4a}$,
—$X_2$—$R_{5a}$, and
—$X_2$—N($R_{8a}$)-$Q_a$-$R_{4a}$;

$R_2'$ is selected from the group consisting of hydrogen, $C_{1-4}$ alkyl, hydroxy$C_{2-4}$ alkylenyl, and alkoxy$C_{2-4}$ alkylenyl;

$Q_a$ is selected from the group consisting of a bond, —C($R_6$)—, —C($R_6$)—C($R_6$)—, —S(O)$_2$—, —C($R_6$)—N($R_{8a}$)—W—, —S(O)$_2$—N($R_{8a}$)—, and —C($R_6$)—O—;

$X_2$ is selected from the group consisting of $C_{2-4}$ alkylene and $C_{2-4}$ alkenylene;

$R_{4a}$ is selected from the group consisting of hydrogen, $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl wherein the $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl groups are unsubstituted or substituted by one or more substituents independently selected from the group consisting of $C_{1-4}$ alkyl, $C_{1-4}$ alkoxy, $C_{1-4}$ alkanoyl, $C_{1-4}$ alkoxycarbonyl, hydroxy$C_{1-4}$ alkyl, halo$C_{1-4}$ alkyl, halo$C_{1-4}$ alkoxy, halogen, nitro, hydroxy, mercapto, cyano, amino, $C_{1-4}$ alkylamino, di($C_{1-4}$ alkyl)amino, and in the case of $C_{1-4}$ alkyl, $C_{2-4}$ alkenyl, $C_{2-4}$ alkynyl, and heterocyclyl, oxo;

$R_{5a}$ is selected from the group consisting of:

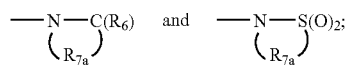

$R_{7a}$ is $C_{2-4}$ alkylene;
$R_{8a}$ is selected from the group consisting of hydrogen and $C_{1-4}$ alkyl;
R is selected from the group consisting of halogen, hydroxy, alkyl, alkenyl, haloalkyl, alkoxy, alkylthio, and —N($R_9$)$_2$;

$R_1$ is selected from the group consisting of:
—$R_4$,
—$X_1$—$R_4$,
—$X_1$—$Y_1$—$R_4$,
—$X_1$—$Y_1$—$X_1$—$Y_1$—$R_4$, and
—$X_1$—$R_5$;

$R_3$ is selected from the group consisting of:
—Z—$R_4$,
—Z—X—$R_4$,
—Z—X—Y—$R_4$, and
—Z—X—$R_5$;

X and $X_1$ are independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y and $Y_1$ are independently selected from the group consisting of:

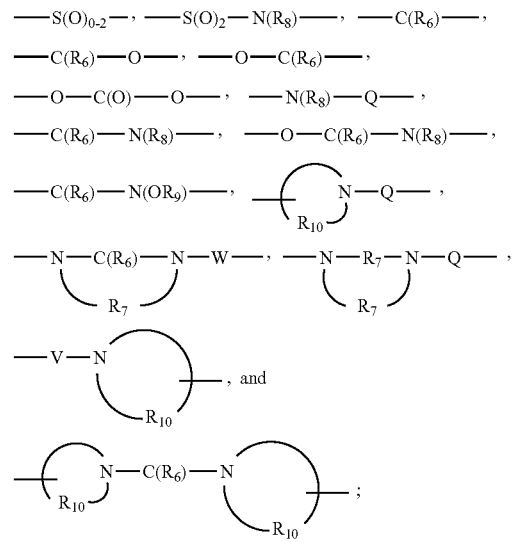

Z is selected from the group consisting of a bond and —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

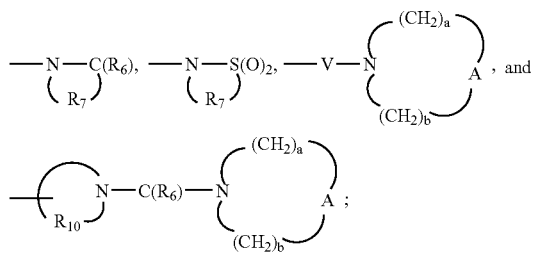

A is selected from the group consisting of —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_8$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is $\leq 7$;

n is an integer from 0 to 4;

m is 0 or 1, with the proviso that when m is 1, n is 0 or 1;

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl; and $R_{10}$ is $C_{3-8}$ alkylene;

or a pharmaceutically acceptable salt thereof.

In one embodiment, the present invention provides a compound of the following Formula V:

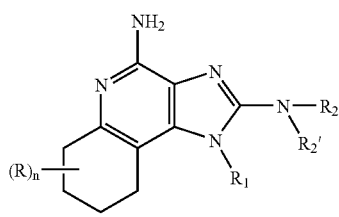

V wherein:

$R_2$ is selected from the group consisting of:
—R$_{4a}$,
-Q$_a$-R$_{4a}$,
—X$_2$—R$_{5a}$, and
—X$_2$—N(R$_{8a}$)-Q$_a$-R$_{4a}$;

$R_2'$ is selected from the group consisting of hydrogen, $C_{1-4}$ alkyl, hydroxyC$_{2-4}$ alkylenyl, and alkoxyC$_{2-4}$ alkylenyl;

$Q_a$ is selected from the group consisting of a bond, —C(R$_6$)—, —C(R$_6$)—C(R$_6$)—, —S(O)$_2$—, —C(R$_6$)—N(R$_{8a}$)—W—, —S(O)$_2$—N(R$_{8a}$)—, and —C(R$_6$)—O—;

$X_2$ is selected from the group consisting of $C_{2-4}$ alkylene and $C_{2-4}$ alkenylene;

$R_{4a}$ is selected from the group consisting of hydrogen, $C_{1-4}$ alkyl, $C_{2-4}$ alkenyl, $C_{2-4}$ alkynyl, aryl, arylC$_{1-4}$ alkylenyl, aryloxyC$_{1-4}$ alkylenyl, $C_{1-4}$ alkylarylenyl, heteroaryl, heteroarylC$_{1-4}$ alkylenyl, heteroaryloxyC$_{1-4}$ alkylenyl, $C_{1-4}$ alkylheteroarylenyl, heterocyclyl, and heterocyclylC$_{1-4}$ alkylenyl wherein the $C_{1-4}$ alkyl, $C_{2-4}$ alkenyl, $C_{2-4}$ alkynyl, aryl, arylC$_{1-4}$ alkylenyl, aryloxyC$_{1-4}$ alkylenyl, $C_{1-4}$ alkylarylenyl, heteroaryl, heteroarylC$_{1-4}$ alkylenyl, heteroaryloxyC$_{1-4}$ alkylenyl, $C_{1-4}$ alkylheteroarylenyl, heterocyclyl, and heterocyclylC$_{1-4}$ alkylenyl groups are unsubstituted or substituted by one or more substituents independently selected from the group consisting of $C_{1-4}$ alkyl, $C_{1-4}$ alkoxy, $C_{1-4}$ alkanoyl, $C_{1-4}$ alkoxycarbonyl, hydroxyC$_{1-4}$ alkyl, haloC$_{1-4}$ alkyl, haloC$_{1-4}$ alkoxy, halogen, nitro, hydroxy, mercapto, cyano, amino, $C_{1-4}$ alkylamino, di($C_{1-4}$ alkyl)amino, and in the case of $C_{1-4}$ alkyl, $C_{2-4}$ alkenyl, $C_{2-4}$ alkynyl, and heterocyclyl, oxo;

$R_{5a}$ is selected from the group consisting of:

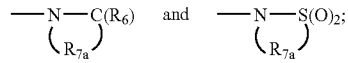

$R_{7a}$ is $C_{2-4}$ alkylene;

$R_{8a}$ is selected from the group consisting of hydrogen and $C_{1-4}$ alkyl;

R is selected from the group consisting of halogen, hydroxy, alkyl, alkenyl, haloalkyl, alkoxy, alkylthio, and —N(R$_9$)$_2$;

$R_1$ is selected from the group consisting of:
—R$_4$,
—X$_1$—R$_4$,
—X$_1$—Y$_1$—R$_4$,
—X$_1$—Y$_1$—X$_1$—Y$_1$—R$_4$, and
—X$_1$—R$_5$;

$X_1$ is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$Y_1$ is selected from the group consisting of:

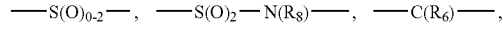
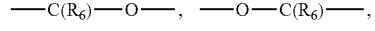
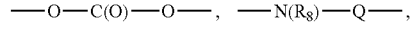
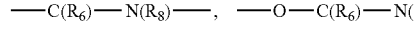
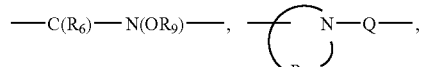
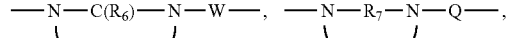
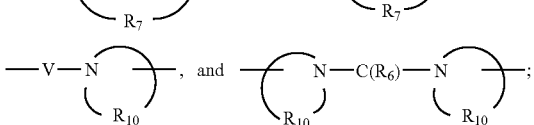

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

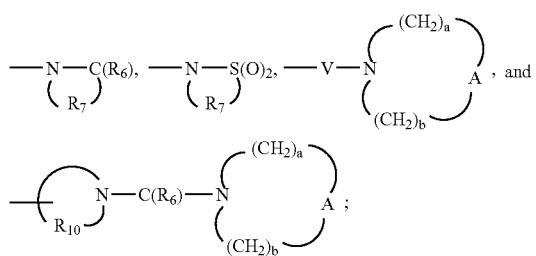

A is selected from the group consisting of —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≦7;

n is an integer from 0 to 4;

$R_6$ is selected from the group consisting of =O and =S;

$R_7$ is C$_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl; and $R_{10}$ is C$_{3-8}$ alkylene;

or a pharmaceutically acceptable salt thereof.

In one embodiment, the present invention provides a compound of the following Formula VI:

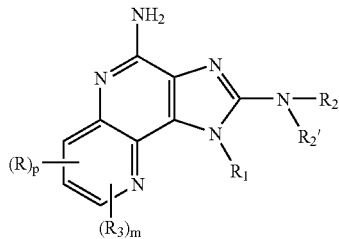

VI wherein:

$R_2$ is selected from the group consisting of:
—R$_{4a}$,
-Q$_a$-R$_{4a}$,
—X$_2$—R$_{5a}$, and
—X$_2$—N(R$_{8a}$)-Q$_a$-R$_{4a}$;

$R_2'$ is selected from the group consisting of hydrogen, C$_{1-4}$ alkyl, hydroxyC$_{2-4}$ alkylenyl, and alkoxyC$_{2-4}$ alkylenyl;

$Q_a$ is selected from the group consisting of a bond, —C(R$_6$)—, —C(R$_6$)—C(R$_6$)—, —S(O)$_2$—, —C(R$_6$)—N(R$_{8a}$)—W—, —S(O)$_2$—N(R$_{8a}$)—, and —C(R$_6$)—O—;

$X_2$ is selected from the group consisting of C$_{2-4}$ alkylene and C$_{2-4}$ alkenylene;

$R_{4a}$ is selected from the group consisting of hydrogen, C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl wherein the C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl groups are unsubstituted or substituted by one or more substituents independently selected from the group consisting of C$_{1-4}$ alkyl, C$_{1-4}$ alkoxy, C$_{1-4}$ alkanoyl, C$_{1-4}$ alkoxycarbonyl, hydroxyC$_{1-4}$ alkyl, haloC$_{1-4}$ alkyl, haloC$_{1-4}$ alkoxy, halogen, nitro, hydroxy, mercapto, cyano, amino, C$_{1-4}$ alkylamino, di(C$_{1-4}$ alkyl)amino, and in the case of C$_{1-4}$ alkyl, C$_{2-4}$ alkenyl, C$_{2-4}$ alkynyl, and heterocyclyl, oxo;

$R_{5a}$ is selected from the group consisting of:

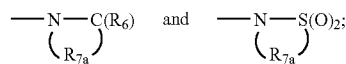

$R_{7a}$ is C$_{2-4}$ alkylene;

$R_{8a}$ is selected from the group consisting of hydrogen and C$_{1-4}$ alkyl;

R is selected from the group consisting of halogen, hydroxy, alkyl, alkenyl, haloalkyl, alkoxy, alkylthio, and —N(R$_9$)$_2$;

$R_1$ is selected from the group consisting of:
—R$_4$,
—X$_1$—R$_4$,
—X$_1$—Y$_1$—R$_4$,
—X$_1$—Y$_1$—X$_1$—Y$_1$—R$_4$, and
—X$_1$—R$_5$;

$R_3$ is selected from the group consisting of:
—Z—R$_4$,
—Z—X—R$_4$,
—Z—X—Y—R$_4$, and
—Z—X—R$_5$;

X and X$_1$ are independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

Y and Y$_1$ are independently selected from the group consisting of:

—S(O)$_{0-2}$—, —S(O)$_2$—N(R$_8$)—, —C(R$_6$)—,

—C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—,

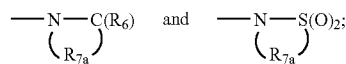

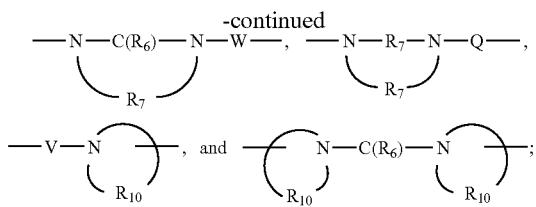

Z is selected from the group consisting of a bond and —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R$_5$ is selected from the group consisting of:

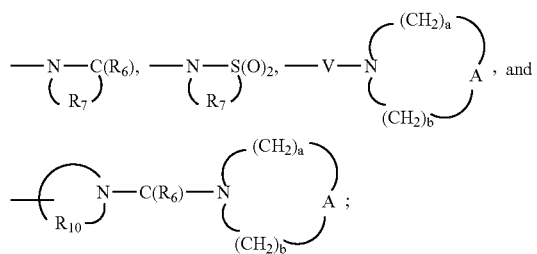

A is selected from the group consisting of —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≤7;

p is an integer from 0 to 3;

m is 0 or 1, with the proviso that when m is 1, p is 0 or 1;

R$_6$ is selected from the group consisting of =O and =S;

R$_7$ is C$_{2-7}$ alkylene;

R$_8$ is selected from the group consisting of hydrogen, alkyl, alkoxyalkylenyl, and arylalkylenyl;

R$_9$ is selected from the group consisting of hydrogen and alkyl; and

R$_{10}$ is C$_{3-8}$ alkylene;

or a pharmaceutically acceptable salt thereof.

In one embodiment, the present invention provides a compound of the following Formula VII:

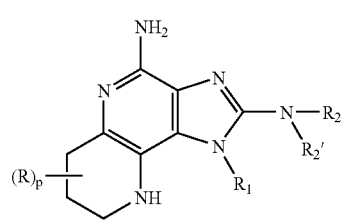

wherein:

R$_2$ is selected from the group consisting of:
—R$_{4a}$,
-Q$_a$-R$_{4a}$,
—X$_2$—R$_{5a}$, and
—X$_2$—N(R$_{8a}$)-Q$_a$-R$_{4a}$;

R$_2$' is selected from the group consisting of hydrogen, C$_{1-4}$ alkyl, hydroxyC$_{2-4}$ alkylenyl, and alkoxyC$_{2-4}$ alkylenyl;

Q$_a$ is selected from the group consisting of a bond, —C(R$_6$)—, —C(R$_6$)—C(R$_6$)—, —S(O)$_2$—, —C(R$_6$)—N(R$_{8a}$)—W—, —S(O)$_2$—N(R$_{8a}$)—, and —C(R$_6$)—O—;

X$_2$ is selected from the group consisting of C$_{2-4}$ alkylene and C$_{2-4}$ alkenylene;

R$_{4a}$ is selected from the group consisting of hydrogen, C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl wherein the C$_{1-4}$ alkyl, C$_{2-4}$ alkenyl, C$_{2-4}$ alkynyl, aryl, arylC$_{1-4}$ alkylenyl, aryloxyC$_{1-4}$ alkylenyl, C$_{1-4}$ alkylarylenyl, heteroaryl, heteroarylC$_{1-4}$ alkylenyl, heteroaryloxyC$_{1-4}$ alkylenyl, C$_{1-4}$ alkylheteroarylenyl, heterocyclyl, and heterocyclylC$_{1-4}$ alkylenyl groups are unsubstituted or substituted by one or more substituents independently selected from the group consisting of C$_{1-4}$ alkyl, C$_{1-4}$ alkoxy, C$_{1-4}$ alkanoyl, C$_{1-4}$ alkoxycarbonyl, hydroxyC$_{1-4}$ alkyl, haloC$_{1-4}$ alkyl, haloC$_{1-4}$ alkoxy, halogen, nitro, hydroxy, mercapto, cyano, amino, C$_{1-4}$ alkylamino, di(C$_{1-4}$ alkyl)amino, and in the case of C$_{1-4}$ alkyl, C$_{2-4}$ alkenyl, C$_{2-4}$ alkynyl, and heterocyclyl, oxo;

R$_{5a}$ is selected from the group consisting of:

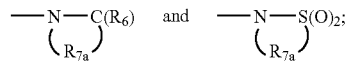

R$_{7a}$ is C$_{2-4}$ alkylene;

R$_{8a}$ is selected from the group consisting of hydrogen and C$_{1-4}$ alkyl;

R is selected from the group consisting of halogen, hydroxy, alkyl, alkenyl, haloalkyl, alkoxy, alkylthio, and —N(R$_9$)$_2$;

R$_1$ is selected from the group consisting of:
—R$_4$,
—X$_1$—R$_4$,
—X$_1$—Y$_1$—R$_4$,
—X$_1$—Y$_1$—X$_1$—Y$_1$—R$_4$, and
—X$_1$—R$_5$;

X$_1$ is selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups;

$Y_1$ is selected from the group consisting of:

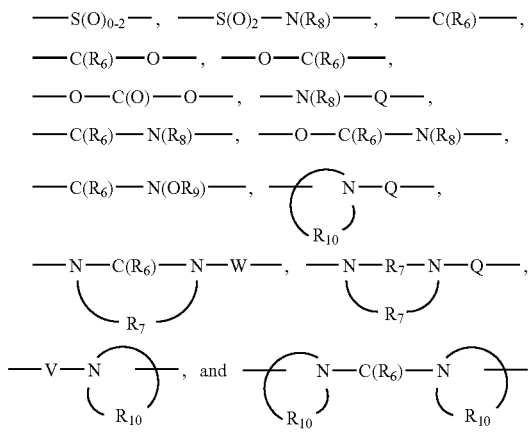

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

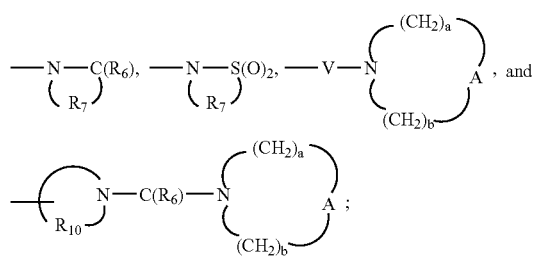

A is selected from the group consisting of —O—, —C(O)—, —S(O)$_{0-2}$—, and —N(R$_4$)—;

Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;

V is selected from the group consisting of —C(R$_6$)—, —O—C(R$_6$)—, —N(R$_8$)—C(R$_6$)—, and —S(O)$_2$—;

W is selected from the group consisting of a bond, —C(O)—, and —S(O)$_2$—;

a and b are independently integers from 1 to 6 with the proviso that a+b is ≦7;

p is an integer from 0 to 3;

$R_6$ is selected from the group consisting of =O and =S;

$R_7$ is $C_{2-7}$ alkylene;

$R_8$ is selected from the group consisting of hydrogen, alkyl, alkoxyalkylenyl, and arylalkylenyl;

$R_9$ is selected from the group consisting of hydrogen and alkyl; and $R_{10}$ is $C_{3-8}$ alkylene;

or a pharmaceutically acceptable salt thereof.

In one embodiment, the present invention provides a compound of the following Formula VIII, which is a prodrug:

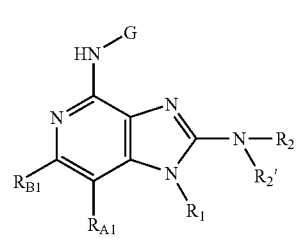

VIII wherein:

G is selected from the group consisting of:
—C(O)—R",
α-aminoacyl,
α-aminoacyl-α-aminoacyl,
—C(O)—O—R",
—C(O)—N(R"")R",
—C(=NY')—R",
—CH(OH)—C(O)—OY',
—CH(OC$_{1-4}$ alkyl)Y$_0$,
—CH$_2$Y$_2$, and
—CH(CH$_3$)Y$_2$;

R" and R"" are independently selected from the group consisting of $C_{1-10}$ alkyl, $C_{3-7}$ cycloalkyl, phenyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R"" can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

Y$_0$ is selected from the group consisting of $C_{1-6}$ alkyl, carboxyC$_{1-6}$ alkylenyl, aminoC$_{1-4}$ alkylenyl, mono-N-C$_{1-6}$ alkylaminoC$_{1-4}$ alkylenyl, and di-N,N-C$_{1-6}$ alkylaminoC$_{1-4}$ alkylenyl;

Y$_2$ is selected from the group consisting of mono-N-C$_{1-6}$ alkylamino, di-N,N-C$_{1-6}$ alkylamino, morpholin-4-yl, piperidin-1-yl, pyrrolidin-1-yl, and 4-C$_{1-4}$ alkylpiperazin-1-yl; and $R_{A1}$, $R_{B1}$, $R_1$, $R_2$, and $R_2'$, are as defined in Formula II above;

or a pharmaceutically acceptable salt thereof.

In another aspect, the present invention provides intermediate compounds of the Formulas IX, X, XI, and XII described below.

In one embodiment, the present invention provides a compound of the following Formula IX:

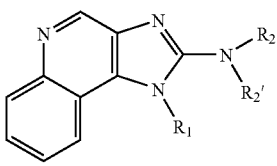

wherein $R_1$, $R_2$, and $R_2'$, are as defined in Formula IV above; or a pharmaceutically acceptable salt thereof.

In one embodiment, the present invention provides a compound of the following Formula X:

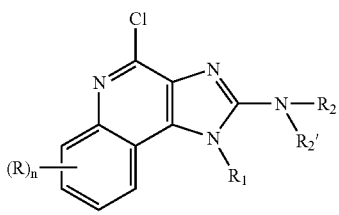

wherein R, n, $R_1$, $R_2$, and $R_2'$, are as defined in Formula IV above;
or a pharmaceutically acceptable salt thereof.

In another embodiment, the present invention provides a compound of the following Formula XI:

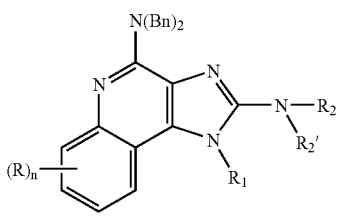

wherein:
—N(Bn)$_2$ is an amino group selected from the group consisting of di(benzyl)amino, di(p-methoxybenzyl)amino, di(p-methylbenzyl)amino, and di(2-furanylmethyl)amino; and R, n, $R_1$, $R_2$, and $R_2'$, are as defined in Formula IV above;
or a pharmaceutically acceptable salt thereof.

In another embodiment, the present invention provides a compound of the following Formula XII:

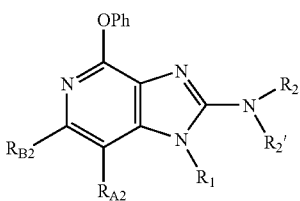

wherein:
—OPh is phenoxy; and
$R_{A2}$, $R_{B2}$, $R_1$, $R_2$, and $R_2'$, are as defined in Formula III above;
or a pharmaceutically acceptable salt thereof.

For any of the compounds presented herein, each one of the following variables (e.g., R, R', $R_1$, $R_2$, $R_2'$, $R_3$, $R_4$, $R_B$, $R_{A1}$, $R_{B1}$, m, n, p, A, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments, e.g., of Formula I, each of R' and R''' is independently a non-interfering substituent. Herein, "non-interfering" means that the ability of the compound or salt, which includes a non-interfering substituent, to modulate the biosynthesis of one or more cytokines (for example, the ability to induce the biosynthesis of one or more cytokines or the ability to inhibit the biosynthesis of one or more cytokines) is not destroyed. Illustrative R' groups include those described herein for $R_1$. Illustrative R''' groups include those described herein for R and $R_3$.

For certain embodiments, including embodiments of Formulas I, II, IV, V, VI, VII, VII, X, XI, or XII, R is selected from the group consisting of halogen, hydroxy, alkyl, alkenyl, haloalkyl, alkoxy, alkylthio, and —N($R_9$)$_2$. For certain embodiments, R is selected from the group consisting of alkyl, alkoxy, halogen, hydroxy, and trifluoromethyl. For certain embodiments, R is selected from the group consisting of halogen and hydroxy. For certain of these embodiments, e.g., of Formula Iv or VI, m is 0. For certain embodiments, e.g., of Formula IV or VI, m is 0, and R is selected from the group consisting of bromo and hydroxy. For certain of these embodiments, R is hydroxy.

For certain embodiments, e.g., of Formula I, R' is selected from the group consisting of hydrogen and non-interfering substituents.

For certain embodiments, including any one of the above embodiments of Formula I, R' is selected from the group consisting of —$R_4$, —$X_1$—$R_4$, —$X_1$—$Y_1$—$R_4$, —$X_1$—$Y_1$—$X_1$—$Y_1$—$R_4$, and —$X_1$—$R_5$.

For certain embodiments, including any one of the above embodiments of Formula I, R' is selected from the group consisting of alkyl, arylalkylenyl, aryloxyalkylenyl, hydroxyalkyl, dihydroxyalkyl, alkylsulfonylalkylenyl, —$X_1$—$Y_1$—$R_4$, and —$X_1$—$R_5$; wherein $X_1$ is alkylene, $Y_1$ is —N($R_8$)—C(O)—, —N($R_8$)—S(O)$_2$—, —N($R_8$)—C($R_6$)—N($R_9$)—, —N($R_8$)—C($R_6$)—O—, or

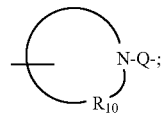

$R_4$ is alkyl, aryl, heteroaryl, arylalkylenyl, heteroarylalkylenyl, or arylalkenylenyl, wherein alkyl, aryl, heteroaryl, or arylalkylenyl is optionally substituted by one or more substituents selected from the group consisting of alkyl, halogen, haloalkyl, haloalkoxy, heterocyclyl, cyano, alkoxy, and dialkylamino; and $R_5$ is

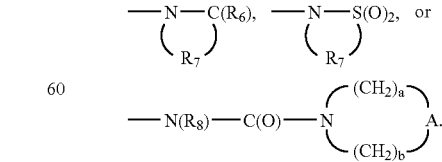

For certain embodiments, including any one of the above embodiments of Formula I, where not excluded, R' is selected from the group consisting of alkyl, aryloxyalkylenyl, hydroxyalkyl, dihydroxyalkyl, haloalkyl, alkylsulfonylalkylenyl, —X$_1$—Y—R$_4$, —X$_1$—R$_5$, and —X$_1$—Y$_1$—X$_1$'—Y$_1$'—R$_4$; wherein X$_1$ is alkylene, X$_1$' is C$_{1-4}$ alkylene or phenylene, Y$_1$ is —C(O)—, —N(R$_8$)—C(O)—, —N(R$_8$)—S(O)$_2$—, —N(R$_8$)—C(R$_6$)—N(R$_8$)—, —N(R$_8$)—C(R$_6$)—N(R$_8$)—C(O)—, —N(R$_8$)—C(R$_6$)—O—,

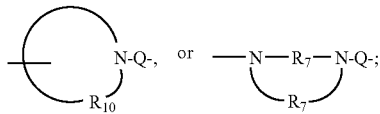

Y$_1$' is —S—, —NHC(O)—, —C(O)—O—, or —C(O)—; R$_4$ is alkyl, aryl, heteroaryl, heterocyclyl, arylalkylenyl, heteroarylalkylenyl, or arylalkenylenyl, wherein alkyl, aryl, heteroaryl, heterocyclyl, or arylalkylenyl is optionally substituted by one or more substituents independently selected from the group consisting of alkyl, halogen, haloalkyl, haloalkoxy, heterocyclyl, cyano, alkoxy, dialkylamino, and, in the case of alkyl or heterocyclyl, oxo; and R$_5$ is

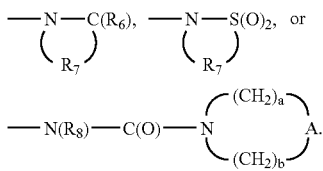

For certain of these embodiments, heterocyclyl as R$_4$ is piperidinyl, imidazolidinyl, or pyrrolidinyl. For certain of these embodiments, heterocyclyl as a substituent on R$_4$ is tetrahydrofuranyl or morpholinyl, and R$_4$ is alkyl.

For certain embodiments of R', including any one of the above embodiments, X$_1$ is C$_{2-4}$ alkylene.

For certain embodiments of R', including any one of the above embodiments, where not excluded, Y$_1$ is —N(R$_8$)—C(O)—, —N(R$_8$)—S(O)$_2$—, —N(R$_8$)—C(R$_6$)—N(R$_8$)—,

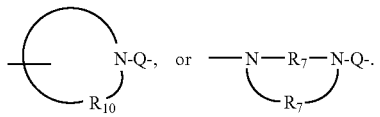

For certain embodiments of R', including any one of the above embodiments, Y$_1$ is —N(R$_8$)—C(O)—, —N(R$_8$)—S(O)$_2$—, —N(R$_9$)—C(R$_6$)—N(R$_8$)—, or

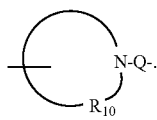

For certain embodiments, including any one of the above embodiments of Formula I, where not excluded, R' is hydrogen.

For certain embodiments, including any one of the above embodiments of Formula I, where not excluded, R' is selected from the group consisting of 2-hydroxy-2-methylpropyl, 2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, and 2-[(cyclohexylcarbonyl)amino]-2-methylpropyl.

For certain embodiments, including any one of the above embodiments of Formula I, where not excluded, R' is selected from the group consisting of 2-hydroxy-2-methylpropyl, 2-methylpropyl, 2-fluoro-2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, 2-[(cyclohexylcarbonyl)amino]-2-methylpropyl, 2,2-dimethyl-4-oxopentyl, (1-hydroxycyclobutyl)methyl, tetrahydro-2H-pyran-4-ylmethyl, 2-(4-methylpiperazin-1-yl)ethyl, (1-acetylpiperidin-4-yl)methyl, 2-(4-acetylpiperazin-1-yl)ethyl, 2-[4-(methylsulfonyl)piperazin-1-yl]ethyl, and [1-(methylsulfonyl)piperidin-4-yl]methyl.

For certain embodiments, e.g., of Formulas II, III, IV, V, VI, VII, VIII, IX, X, XI, or XII, R$_1$ is selected from the group consisting of —R$_4$, —X$_1$—R$_4$, —X$_1$—Y$_1$—R$_4$, —X$_1$—Y$_1$—X$_1$—Y$_1$—R$_4$, and —X$_1$—R$_5$.

For certain embodiments, including any one of the above embodiments of Formulas II, III, IV, V, VI, VII, VIII, IX, X, XI, or XII, R$_1$ is selected from the group consisting of alkyl, arylalkylenyl, aryloxyalkylenyl, hydroxyalkyl, dihydroxyalkyl, alkylsulfonylalkylenyl, —X$_1$—Y$_1$—R$_4$, and —X$_1$—R$_5$; wherein X$_1$ is alkylene, Y$_1$ is —N(R$_8$)—C(O)—, —N(R$_8$)—S(O)$_2$—, —N(R$_8$)—C(R$_6$)—N(R$_8$)—, —N(R$_8$)—C(R$_6$)—O—, or

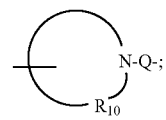

R$_4$ is alkyl, aryl, heteroaryl, arylalkylenyl, heteroarylalkylenyl, or arylalkenylenyl, wherein alkyl, aryl, heteroaryl, or arylalkylenyl is optionally substituted by one or more substituents selected from the group consisting of alkyl, halogen, haloalkyl, haloalkoxy, heterocyclyl, cyano, alkoxy, and dialkylamino; and R$_5$ is

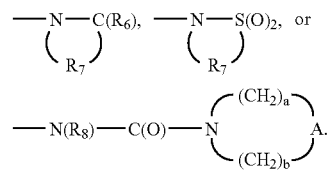

For certain of these embodiments, R$_1$ is benzyl.

For certain embodiments, including any one of the above embodiments of Formulas II, III, IV, V, VI, VII, VIII, IX, X, XI, or XII, where not excluded, R$_1$ is selected from the group consisting of alkyl, aryloxyalkylenyl, hydroxyalkyl, dihydroxyalkyl, haloalkyl, alkylsulfonylalkylenyl, —X$_1$—Y$_1$—R$_4$, —X$_1$—R$_5$, and —X$_1$—Y$_1$—X$_1$'—Y$_1$'—R$_4$; wherein X$_1$ is alkylene, X$_1$' is C$_{1-4}$ alkylene or phenylene, Y$_1$ is —C(O)—, —N(R$_8$)—C(O)—, —N(R$_8$)—S(O)$_2$—, —N(R$_8$)—C(R$_6$)—N(R$_8$)—, —N(R$_8$)—C(R$_6$)—N(R$_8$)—C(O)—, —N(R$_8$)—C(R$_6$)—O—,

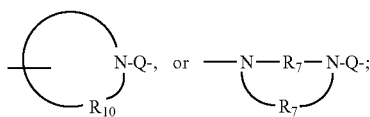

$Y_1'$ is —S—, —NHC(O)—, —C(O)—O—, or —C(O)—; $R_4$ is alkyl, aryl, heteroaryl, heterocyclyl, arylalkylenyl, heteroarylalkylenyl, or arylalkenylenyl, wherein alkyl, aryl, heteroaryl, heterocyclyl, or arylalkylenyl is optionally substituted by one or more substituents independently selected from the group consisting of alkyl, halogen, haloalkyl, haloalkoxy, heterocyclyl, cyano, alkoxy, dialkylamino, and, in the case of alkyl or heterocyclyl, oxo; and $R_5$ is

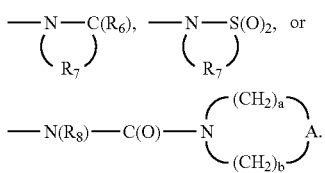

For certain of these embodiments, heterocyclyl as $R_4$ is piperidinyl, imidazolidinyl, or pyrrolidinyl. For certain of these embodiments, heterocyclyl as a substituent on $R_4$ is tetrahydrofuranyl or morpholinyl, and $R_4$ is alkyl.

For certain embodiments of $R_1$, including any one of the above embodiments of Formulas II, III, IV, V, VI, VII, VIII, IX, X, XI, or XII, $X_1$ is $C_{2-4}$ alkylene.

For certain embodiments of $R_1$, including any one of the above embodiments of Formulas II, III, IV, V, VI, VII, VIII, IX, X, XI, or XII, where not excluded, $Y_1$ is —N($R_8$)—C(O)—, —N($R_8$)—S(O)$_2$—, —N($R_8$)—C($R_6$)—N($R_8$)—,

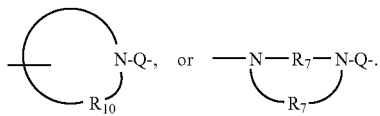

For certain embodiments of $R_1$, including any one of the above embodiments of Formulas II, III, IV, V, VI, VII, VIII, IX, X, XI, or XII, $Y_1$ is —N($R_8$)—C(O)—, —N($R_8$)—S(O)$_2$—, —N($R_8$)—C($R_6$)—N($R_8$)—, or

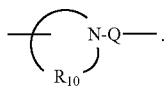

For certain embodiments, including any one of the above embodiments of Formulas II, III, IV, V, VI, VII, VIII, IX, X, XI, or XII, where not excluded, $R_1$ is hydrogen.

For certain embodiments, including any one of the above embodiments of Formulas II, III, IV, V, VI, VII, VIII, IX, X, XI, or XII, where not excluded, $R_1$ is selected from the group consisting of 2-hydroxy-2-methylpropyl, 2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, and 2-[(cyclohexylcarbonyl)amino]-2-methylpropyl.

For certain embodiments, including any one of the above embodiments of Formulas II, III, IV, V, VI, VII, VIII, IX, X, XI, or XII, where not excluded, $R_1$ is selected from the group consisting of 2-hydroxy-2-methylpropyl, 2-methylpropyl, 2-fluoro-2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, 2-[(cyclohexylcarbonyl)amino]-2-methylpropyl, 2,2-dimethyl-4-oxopentyl, (1-hydroxycyclobutyl)methyl, tetrahydro-2H-pyran-4-ylmethyl, 2-(4-methylpiperazin-1-yl)ethyl, (1-acetylpiperidin-4-yl)methyl, 2-(4-acetylpiperazin-1-yl)ethyl, 2-[4-(methylsulfonyl)piperazin-1-yl]ethyl, and [1-(methylsulfonyl)piperidin-4-yl]methyl.

For certain embodiments, including any one of the above embodiments of Formulas I, II, III, IV, V, VI, VII, VIII, IX, X, XI, or XII, $R_2$ is selected from the group consisting of —$R_{4a}$, -$Q_a$-$R_{4a}$, —$X_2$—$R_{5a}$, and —$X_2$—N($R_{8a}$)-$Q_a$-$R_{4a}$.

For certain embodiments, including any one of the above embodiments of Formulas I, II, III, IV, V, VI, VII, VIII, IX, X, XI, or XII, $R_2$ is selected from the group consisting of —$R_{4a}$ and -$Q_a$-$R_{4a}$. For certain of these embodiments, $R_2$ is -$Q_a$-$R_{4a}$. For certain of these embodiments, $Q_a$ is —C(O)—O—. For certain of these embodiments, $R_2$ is O—C(O)—O—$C_{1-4}$ alkyl.

For certain embodiments, including any one of the above embodiments of Formulas I, II, III, IV, V, VI, VII, VIII, IX, X, XI, or XII, where not excluded, $Q_a$ is —C(O)—, —S(O)$_2$—, or —N($R_{8a}$)—C(O)—N($R_{8a}$)—.

For certain embodiments, including any one of the above embodiments of Formulas I, II, III, IV, V, VI, VII, VIII, IX, X, XI, or XII, where not excluded, $R_2$ is $R_{4a}$.

For certain of these embodiments, $R_{4a}$ is selected from the group consisting of hydrogen, $C_{1-4}$ alkyl, $C_{1-4}$ alkoxy$C_{2-4}$ alkylenyl, and hydroxy$C_{2-4}$ alkylenyl. For certain of these embodiments, $R_{4a}$ is selected from the group consisting of hydrogen, methyl, ethyl, 2-methoxyethyl, 3-methoxypropyl, 2-hydroxyethyl, and 3-hydroxypropyl. For certain of these embodiments, $R_{4a}$ is hydrogen.

For certain embodiments, including any one of the above embodiments of Formulas I, II, III, IV, V, VI, VII, VIII, IX, X, XI, or XII, $R_2'$ is selected from the group consisting of hydrogen, $C_{1-4}$ alkyl, hydroxy$C_{2-4}$ alkylenyl, and alkoxy$C_{2-4}$ alkylenyl.

For certain embodiments, including any one of the above embodiments of Formulas I, II, III, IV, V, VI, VII, VIII, IX, X, XI, or XII, $R_2'$ is hydrogen.

For certain embodiments, including any one of the above embodiments of Formulas I, II, III, IV, V, VI, VII, VIII, IX, X, XI, or XII, $R_{4a}$ is hydrogen, and $R_2'$ is hydrogen.

For certain embodiments of Formulas I, II, III, IV, V, VI, VII, VIII, IX, X, XI, or XII, $R_2$ is —C(O)—O—$C_{1-4}$ alkyl, and $R_2'$ is hydrogen.

For certain embodiments, including any one of the above embodiments of Formulas I, II, III, IV, V, VI, VII, VIII, IX, X, XI, or XII, where not excluded, $R_2$ is selected from the group consisting of —$R_{4a}$, —$X_2$—$R_{5a}$, and —$X_2$—N($R_{8a}$)-$Q_a$-$R_{4a}$. For certain of these embodiments, $X_2$ is ethylene. For certain of these embodiments, $Q_a$ is —C(O)—, —S(O)$_2$—, or —N($R_{8a}$)—C(O)—N($R_{8a}$)—. For certain of these embodiments, $R_{8a}$ is hydrogen. For certain of these embodiments, $R_{4a}$ is selected from the group consisting of hydrogen, $C_{1-4}$ alkyl, $C_{1-4}$ alkoxy$C_{2-4}$ alkylenyl, or hydroxy$C_{2-4}$ alkylenyl.

For certain embodiments, e.g., of Formulas II, IV, VI, and VIII, $R_3$ is selected from the group consisting of —Z—$R_4$, —Z—X—$R_4$, —Z—X—Y—$R_4$, and —Z—X—$R_5$. For certain of these embodiments, Z is a bond. For certain of these embodiments, X is selected from the group consisting of alkylene, arylene, heteroarylene, and heterocyclylene wherein the alkylene group can be optionally interrupted or terminated with arylene, heteroarylene, or heterocyclylene, and optionally interrupted by one or more —O— groups.

For certain embodiments, including any one of the above embodiments of Formulas II, IV, VI, and VIII, where $R_3$ is present, $R_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, 3-(N,N-dimethylaminocarbonyl)phenyl, 4-methoxyphenyl, 4-(hydroxymethyl)phenyl, 3-chlorophenyl, and 4-chlorophenyl. For certain of these embodiments, m is 1, and n is 0.

For certain embodiments, including any one of the above embodiments of Formulas II, IV, VI, and VIII, where $R_3$ is present, $R_3$ is selected from the group consisting of phenyl, pyridin-3-yl, pyridin-4-yl, 5-(hydroxymethyl)pyridin-3-yl, 2-ethoxyphenyl, 3-(morpholine-4-carbonyl)phenyl, and 3-(N,N-dimethylaminocarbonyl)phenyl. For certain of these embodiments, m is 1, and n is 0.

For certain embodiments, including any one of the above embodiments of Formulas II, IV, VI, and VIII, where $R_3$ is present, $R_3$ is at the 7-position.

For certain embodiments, including any one of the above embodiments of Formula I, $R_A$ and $R_B$ are independently selected from the group consisting of hydrogen, halogen, alkyl, alkenyl, alkoxy, alkylthio, and —N($R_9$)$_2$.

For certain embodiments, including any one of the above embodiments of Formula I, where not excluded, $R_A$ and $R_B$ taken together form a fused benzene ring or a fused pyridine ring wherein the benzene ring or pyridine ring is unsubstituted or substituted by one or more R''' groups. For certain of these embodiments, one R''' group is present. For certain embodiments, $R_A$ and $R_B$ taken together form a fused benzene ring or a fused pyridine ring wherein the benzene ring or pyridine ring is unsubstituted or substituted by one $R_3$ group, or substituted by one $R_3$ group and one R group, or substituted by one or more R groups. In certain of these embodiments, $R_A$ and $R_B$ taken together form a fused benzene ring. In certain of these embodiments, $R_A$ and $R_B$ taken together form a fused pyridine ring. In certain of these embodiments, the fused benzene ring or fused pyridine ring is unsubstituted.

For certain embodiments, including any one of the above embodiments of Formula I, where not excluded, $R_A$ and $R_B$ taken together form a fused 5 to 7 membered saturated ring optionally containing one nitrogen atom wherein the ring is unsubstituted or substituted by one or more R groups. In certain of these embodiments, the fused 5 to 7 membered saturated ring is a carbocyclic ring. In certain of these embodiments, the fused 5 to 7 membered saturated ring contains one nitrogen atom. In certain of these embodiments, the fused 5 to 7 membered saturated ring is unsubstituted.

For certain embodiments, including any one of the above embodiments of Formulas II or VIII, $R_{A1}$ and $R_{B1}$ are independently selected from the group consisting of hydrogen, halogen, alkyl, alkenyl, alkoxy, alkylthio, and —N($R_9$)$_2$.

For certain embodiments, including any one of the above embodiments of Formulas II or VIII, where not excluded, $R_{A1}$ and $R_{B1}$ taken together form a fused benzene ring or a fused pyridine ring wherein the benzene ring or pyridine ring is unsubstituted or substituted by one $R_3$ group, or substituted by one $R_3$ group and one R group, or substituted by one or more R groups. In certain of these embodiments, $R_{A1}$ and $R_{B1}$ taken together form a fused benzene ring. In certain of these embodiments, $R_{A1}$ and $R_{B1}$ taken together form a fused pyridine ring. In certain of these embodiments, the fused benzene ring or fused pyridine ring is unsubstituted.

For certain embodiments, including any one of the above embodiments of Formulas II or VIII, where not excluded, $R_{A1}$ and $R_{B1}$ taken together form a fused 5 to 7 membered saturated ring optionally containing one nitrogen atom wherein the ring is unsubstituted or substituted by one or more R groups. In certain of these embodiments, the fused 5 to 7 membered saturated ring is a carbocyclic ring. In certain of these embodiments, the fused 5 to 7 membered saturated ring contains one nitrogen atom. In certain of these embodiments, the fused 5 to 7 membered saturated ring is unsubstituted.

For certain embodiments, e.g., of Formulas III and XII, $R_{A2}$ and $R_{B2}$ are independently selected from the group consisting of hydrogen, halogen, alkyl, alkenyl, alkoxy, alkylthio, and —N($R_9$)$_2$. For certain embodiments, $R_{A2}$ and $R_{B2}$ are each independently selected from the group consisting of hydrogen and alkyl. For certain embodiments, $R_{A2}$ and $R_{B2}$ are each methyl.

For certain embodiments, $R_{4a}$ is selected from the group consisting of hydrogen, $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl wherein the $C_{1-4}$ alkyl, $C_{2-4}$ alkenyl, $C_{2-4}$ alkynyl, aryl, aryl$C_{1-4}$ alkylenyl, aryloxy$C_{1-4}$ alkylenyl, $C_{1-4}$ alkylarylenyl, heteroaryl, heteroaryl$C_{1-4}$ alkylenyl, heteroaryloxy$C_{1-4}$ alkylenyl, $C_{1-4}$ alkylheteroarylenyl, heterocyclyl, and heterocyclyl$C_{1-4}$ alkylenyl groups are unsubstituted or substituted by one or more substituents independently selected from the group consisting of $C_{1-4}$ alkyl, $C_{1-4}$ alkoxy, $C_{1-4}$ alkanoyl, $C_{1-4}$ alkoxycarbonyl, hydroxy$C_{1-4}$ alkyl, halo$C_{1-4}$ alkyl, halo$C_{1-4}$ alkoxy, halogen, nitro, hydroxy, mercapto, cyano, amino, $C_{1-4}$ alkylamino, di($C_{1-4}$ alkyl)amino, and in the case of $C_{1-4}$ alkyl, $C_{2-4}$ alkenyl, $C_{2-4}$ alkynyl, and heterocyclyl, oxo.

For certain embodiments, $R_{4a}$ is selected from the group consisting of hydrogen, $C_{1-4}$ alkyl, $C_{1-4}$ alkoxy$C_{2-4}$ alkylenyl, or hydroxy$C_{2-4}$ alkylenyl.

For certain embodiments, $R_{4a}$ is hydrogen.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo.

For certain embodiments, $R_4$ is alkyl, aryl, heteroaryl, arylalkylenyl, heteroarylalkylenyl, or arylalkenylenyl, wherein alkyl, aryl, heteroaryl, or arylalkylenyl is optionally substituted by one or more substituents selected from the group consisting of alkyl, halogen, haloalkyl, haloalkoxy, heterocyclyl, cyano, alkoxy, and dialkylamino. For certain embodiments, $R_4$ is alkyl, aryl, heteroaryl, heterocyclyl, arylalkylenyl, heteroarylalkylenyl, or arylalkenylenyl, wherein alkyl, aryl, heteroaryl, heterocyclyl, or arylalkylenyl is optionally substituted by one or more substituents independently selected from the group consisting of alkyl, halogen, haloalkyl, haloalkoxy, heterocyclyl, cyano, alkoxy, dialkylamino, and, in the case of alkyl or heterocyclyl, oxo. For certain of these embodiments, heterocyclyl as $R_4$ is piperidinyl, imidazolidinyl, or pyrrolidinyl. For certain of these embodiments, heterocyclyl as a substituent on $R_4$ is tetrahydrofuranyl or morpholinyl, and $R_4$ is alkyl.

For certain embodiments, $R_{5a}$ is selected from the group consisting of:

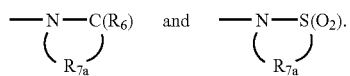

For certain embodiments, $R_5$ is selected from the group consisting of:

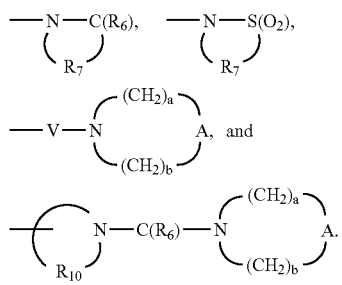

For certain embodiments, $R_5$ is

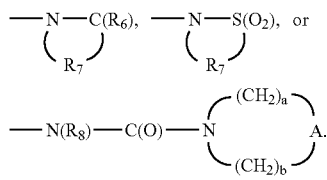

For certain embodiments, $R_6$ is selected from the group consisting of =O and =S. For certain embodiments, $R_6$ is =O.

For certain embodiments, $R_{7a}$ is $C_{2-4}$ alkylene.

For certain embodiments, $R_7$ is $C_{2-7}$ alkylene. For certain embodiments, $R_7$ is ethylene. For certain embodiments, $R_7$ is propylene.

For certain embodiments, $R_{8a}$ is selected from the group consisting of hydrogen and $C_{1-4}$ alkyl. For certain embodiments, $R_{8a}$ is hydrogen.

For certain embodiments, $R_8$ is selected from the group consisting of hydrogen, alkyl, alkoxyalkylenyl, and arylalkylenyl. For certain embodiments, $R_8$ is hydrogen.

For certain embodiments, $R_9$ is selected from the group consisting of hydrogen and alkyl.

For certain embodiments, $R_{10}$ is $C_{3-8}$ alkylene. For certain embodiments, $R_{10}$ is pentylene.

For certain embodiments, A is selected from the group consisting of —O—, —C(O)—, —S(O)$_{0-2}$—, and —N($R_4$)—. For certain embodiments, A is —O—. For certain embodiments, A is —N($R_4$)—.

For certain embodiments, $Q_a$ is selected from the group consisting of a bond, —C($R_6$)—, —C($R_6$)—C($R_6$)—, —S(O)$_2$—, C($R_6$)—N($R_{8a}$)—W—, —S(O)$_2$—N($R_{8a}$)—, and —C($R_6$)—O—. For certain embodiments, $Q_a$ is —C(O)—, —S(O)$_2$—, or —N($R_{8a}$)—C(O)—N($R_{8a}$)—. For certain embodiments, $Q_a$ is —C(O)—O—.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(OR$_9$)—. For certain embodiments, Q is —C($R_6$)—N($R_8$)—. For certain embodiments, Q is —S(O)$_2$—. For certain embodiments, Q is —C($R_6$)—. For certain embodiments, Q is selected from the group consisting of —C(O)—, —S(O)$_2$—, —C($R_6$)—N($R_8$)—W—, and —C($R_6$)—O—. For certain of these embodiments, W is a bond. For certain of these embodiments, W is —C(O)—.

For certain embodiments, V is selected from the group consisting of —C($R_6$)—, —O—C($R_6$)—, —N($R_8$)—C($R_6$)—, and —S(O)$_2$—. For certain embodiments, V is —N($R_8$)—C(O)—.

For certain embodiments, W is selected from the group consisting of a bond, —C(O)—, and —S(O)$_2$—. For certain embodiments, W is a bond. For certain embodiments, W is —C(O)—.

For certain embodiments, X and $X_1$ are independently selected from the group consisting of alkylene, alkenylene, alkynylene, arylene, heteroarylene, and heterocyclylene wherein the alkylene, alkenylene, and alkynylene groups can be optionally interrupted or terminated with arylene, heteroarylene, or heterocyclylene, and optionally interrupted by one or more —O— groups.

For certain embodiments, X is selected from the group consisting of alkylene, arylene, heteroarylene, and heterocyclylene wherein the alkylene group can be optionally interrupted or terminated with arylene, heteroarylene, or heterocyclylene, and optionally interrupted by one or more —O— groups. For certain embodiments, X is phenylene. For certain embodiments, X is pyridinylene.

For certain embodiments, $X_1$ is alkylene. For certain embodiments, $X_1$ is $C_{2-4}$ alkylene.

For certain embodiments, $X_1$ is $C_{1-4}$ alkylene or phenylene.

For certain embodiments, $X_2$ is selected from the group consisting of $C_{2-4}$ alkylene and $C_{2-4}$ alkenylene. For certain embodiments, $X_2$ is ethylene.

For certain embodiments, Y and $Y_1$ are independently selected from the group consisting of —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_9$)—, —C($R_6$)—N(OR$_9$)—,

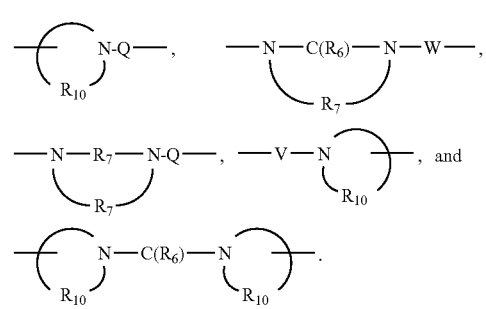

For certain embodiments, Y or $Y_1$ is —C(O)—, —N($R_8$)—C(O)—, —N($R_8$)—S(O)$_2$—, —N($R_8$)—C($R_6$)—N($R_8$)—, —N($R_8$)—C($R_6$)—N($R_8$)—C(O)—, —N($R_8$)—C($R_6$)—O—,

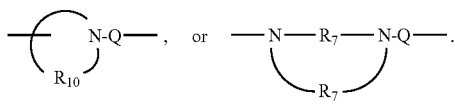

For certain embodiments, Y or $Y_1$ is —N($R_8$)—C(O)—, —N($R_8$)—S(O)$_2$—, —N($R_8$)—C($R_6$)—N($R_8$)—, —N($R_8$)—C($R_6$)—O—, or

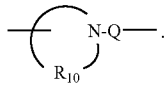

For certain embodiments, Y or $Y_1$ is —N($R_8$)—C(O)—, —N($R_8$)—S(O)$_2$—, —N($R_8$)—C($R_6$)—N($R_8$)—, or

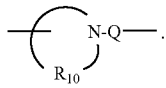

For certain embodiments, $Y_1$ is —S—, —NHC(O)—, —C(O)—O—, or —C(O)—.

For certain embodiments, Z is selected from the group consisting of a bond and —O—. For certain embodiments, Z is a bond.

For certain embodiments, a and b are independently integers from 1 to 6 with the proviso that a+b is ≦7. For certain embodiments, a and b are each 2.

For certain embodiments, including any one of the above embodiments of Formulas IV or V, where not excluded, n is an integer from 0 to 4.

For certain embodiments, e.g., of Formula IV, m is 0 or 1, with the proviso that when m is 1, n is 0 or 1.

For certain embodiments, including any one of the above embodiments of Formula IV, where not excluded, m is 1, and n is 0.

For certain embodiments, including any one of the above embodiments of Formula V, where not excluded, n is 0.

For certain embodiments, including any one of the above embodiments of Formulas IV or VI, where not excluded, m is 0.

For certain embodiments, including any one of the above embodiments of Formula IV, where not excluded, m is 0, and n is 0.

For certain embodiments, e.g., of Formula VI, m is 0 or 1, with the proviso that when m is 1, p is 0 or 1.

For certain embodiments, including any one of the above embodiments of Formulas VI or VII, where not excluded, p is an integer from 0 to 3.

For certain embodiments, including any one of the above embodiments of Formula VI, where not excluded, m is 1, and p is 0.

For certain embodiments, including any one of the above embodiments of Formula VI, where not excluded, m is 0, and p is 0.

For certain embodiments, including any one of the above embodiments of Formula VII, where not excluded, p is 0.

For certain embodiments of the compounds of Formulas I, II, III, IV, V, VI, or VII the —NH$_2$ group can be replaced by an —NH-G group, as shown in the compound of Formula VIII, to form prodrugs. In such embodiments, G is selected from the group consisting of —C(O)—R", α-aminoacyl, α-aminoacyl-α-aminoacyl, —C(O)—O—R", —C(O)—N(R"")R", —C(=NY')—R", —CH(OH)—C(O)—OY', —CH(OC$_{1-4}$ alkyl)Y$_0$, —CH$_2$Y$_2$, and —CH(CH$_3$)Y$_2$. In some embodiments G is selected from the group consisting of —C(O)—R", α-aminoacyl, α-aminoacyl-α-aminoacyl, and —C(O)—O—R". Preferably, R" and R"" are independently selected from the group consisting of C$_{1-10}$ alkyl, C$_{3-7}$ cycloalkyl, phenyl, and benzyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$. R"" may also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_4$ alkylenyl, mono-N-C$_{1-6}$ alkylaminoC$_{1-4}$ alkylenyl, and di-N,N-C$_{1-6}$ alkylaminoC$_{1-4}$ alkylenyl. Preferably, Y$_2$ is selected from the group consisting of mono-N-C$_{1-6}$ alkylamino, di-N,N-C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments containing —NH-G, G is —C(O)—R", α-aminoacyl, α-aminoacyl-α-aminoacyl, or —C(O)—O—R".

In some embodiments, a compound of Formula I, II, III, IV, V, VI, VI, VII, VIII, or any of the embodiments thereof described herein induces the biosynthesis of one or more cytokines (for example, IFN-α and/or TNF-α).

In some embodiments, a compound of Formula I, II, III, IV, V, VI, VI, VII, VIII, or any of the embodiments thereof described herein inhibits the biosynthesis of one or more cytokines (for example, TNF-α).

For certain embodiments, the present invention provides a pharmaceutical composition comprising a therapeutically effective amount of a compound or salt of any one of the above embodiments of Formulas I, II, III, IV, V, VI, VII, and VIII, and a pharmaceutically acceptable carrier.

For certain embodiments, the present invention provides a method of inducing cytokine biosynthesis in an animal comprising administering an effective amount of a compound or salt of any one of the above embodiments of Formulas I, II, III, IV, V, VI, VII, and VIII, or a pharmaceutical composition of any one of the above embodiments of Formulas I, II, III, IV, V, VI, VII, and VIII to the animal.

For certain embodiments, the present invention provides a method of treating a viral disease in an animal comprising administering a therapeutically effective amount of a compound or salt of any one of the above embodiments of Formulas I, II, III, IV, V, VI, VII, and VIII or a pharmaceutical composition of any one of the above embodiments of Formulas I, II, III, IV, V, VI, VII, and VIII to the animal.

For certain embodiments, the present invention provides a method of treating a neoplastic disease in an animal comprising administering a therapeutically effective amount of a compound or salt of any one of the above embodiments of Formulas I II, III, IV, V, VI, VII, and VIII or a pharmaceutical composition of any one of the above embodiments of Formulas I, II, III, IV, V, VI, VII, and VIII to the animal.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclobutyl, cyclobutylmethyl, cyclopentyl, cyclopentylmethyl, cyclohexyl, cyclohexylmethyl, adamantyl, and substituted and unsubstituted bornyl, norbornyl, and norbornenyl.

Unless otherwise specified, "alkylene", "-alkylene-", "alkenylene", "-alkenylene-", "alkynylene", and "-alkynylene-" are the divalent forms of the "alkyl", "alkenyl", and "alkynyl" groups defined above. The terms "alkylenyl", "alkenylenyl", and "alkynylenyl" are used when "alkylene", "alkenylene", and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene," and "heterocyclylene", respectively, are substituted. For example, an alkylarylenyl group comprises an arylene moiety to which an alkyl group is attached.

The term "fused 5 to 7 membered saturated ring" includes rings which are fully saturated except for the bond where the ring is fused.

When a group (or substituent or variable) is present more than once in any Formula described herein, each group (or substituent or variable) is independently selected, whether explicitly stated or not. For example, for the formula —N($R_9$)$_2$ each $R_9$ group is independently selected. In another example, when an $R_1$ and an $R_3$ group both contain an $R_4$ group, each $R_4$ group is independently selected. In a further example, when more than one —N($R_8$)—C($R_6$)—N($R_8$)— group is present (i.e., Y and $Y_1$ both contain a —N($R_8$)—C($R_6$)—N($R_8$)— group) each $R_8$ group is independently selected and each $R_6$ group is independently selected.

The invention is inclusive of the compounds described herein (including intermediates) in any of their pharmaceutically acceptable forms, including isomers (e.g., diastereomers and enantiomers), salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Preparation of The Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive*

Organic Synthesis, v. 1-8, Pergamon Press, Oxford, England, (1991); or Beilsteins Handbuch der organischen Chemie, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, Protective Groups in Organic Synthesis, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R, $R_1$, $R_2$, $R_2'$, $R_{4a}$, and n are as defined above, and $R_{2a}$ is —$X_2$—$R_{5a}$ or —$X_2$—N($R_{8a}$)-$Q_a$-$R_{4a}$. In step (1) or (1a) of Reaction Scheme I, a 2-chloroquinoline-3,4-diamine of Formula XIII reacts with a isothiocyanate of Formula $R_{4a}$N═C═S or $R_2'$N═C═S to provide a thiourea, which cyclizes to a 1H-imidazo[4,5-c]quinolin-2-amine of Formula XIV or XVI. Many isothiocyanates are commercially available; others can be prepared using conventional synthetic methods. Several 2-chloroquinoline-3,4-diamines of Formula XIII are known or can be prepared using known methods. See, for example, U.S. Pat. No. 4,988,815 (André et al); U.S. Pat. No. 6,069,149 (Nanba et al); U.S. Pat. No. 6,518,265 (Kato et al.), U.S. Pat. No. 6,670,372 (Charles et al); U.S. Pat. No. 6,683,088 (Crooks et al); and U.S. Pat. No. 6,664,260 (Charles et al). For some embodiments, the $R_1$ group on a compound of Formula XIII is converted to another $R_1$ group using a variety of synthetic methods. For example, a compound or salt of Formula XIII wherein $R_1$ is a tert-butyl group can be converted to a compound of Formula XIII wherein $R_1$ is hydrogen by heating the tert-butyl amine with hydrochloric acid in a suitable solvent such as methanol at an elevated temperature such as 75° C. In another example, a compound of Formula XIII wherein $R_1$ is —$X_1$—NH-Boc, in which Boc is tert-butoxycarbonyl, can be converted to a compound of Formula XIII wherein $R_1$ is $R_{1a}$ using the methods of Reaction Scheme III below. Similarly, a compound of Formula XIII wherein $R_1$ is

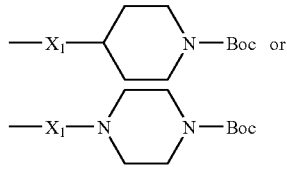

can be converted to a compound of Formula XIII wherein $R_1$ is

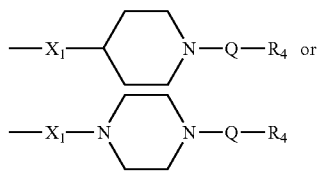

using the methods of Reaction Scheme III.

Some compounds of XIII in which $R_1$ is a 1-hydroxycycloalkylmethyl group or a 2-fluoro-2-methylpropyl group can be prepared in two steps by (i) reacting 2,4-dichloro-3-nitroquinoline with an amine of formula $H_2N$—$R_1$ or a salt thereof and (ii) reducing the nitro group using conventional methods. Methods that can be used to carry out step (i) and step (ii) are described in the U.S. patents referenced above.

Some amines of the Formula $H_2N$—$R_1$ in which $R_1$ is a 1-hydroxycycloalkylmethyl group, or salts thereof, are commercially available. Others can be prepared by known methods. For example, cyanide anion, which can be generated by complexing potassium cyanide and 18-Crown-6, can be added to a cyclic ketone in the presence of trimethylsilyl cyanide. The reaction may be carried out neat or in a suitable solvent at or below room temperature. The resulting cyanohydrin can then be reduced to a 1-aminomethyl alcohol using conventional methods; for example, the cyanohydrin can be combined with lithium aluminum hydride in a suitable solvent, such as tetrahydrofuran, at a sub-ambient temperature, such as 0° C. Amines of Formula $H_2N$—$R_1$ in which $R_1$ is a 1-hydroxycycloalkylmethyl may also be prepared by combining a cyclic ketone with excess nitromethane in a suitable solvent such as ethanol or methanol in the presence of a catalytic amount of base such as sodium ethoxide or sodium hydroxide and reducing the resultant nitromethyl-substituted compound using conventional heterogeneous hydrogenation conditions. The hydrogenation is typically carried out in the presence of a catatlyst such as palladium hydroxide on carbon, palladium on carbon, or Raney nickel in a suitable solvent such as ethanol. Both the reaction with nitromethane and the reduction can be carried out at ambient temperature. A wide variety of cyclic ketones, such as cyclopentanone and cyclobutanone, can be obtained from commercial sources; others can be synthesized using known synthetic methods.

For some embodiments, $R_1$ is a 2-fluoro-2-methylpropyl group. The corresponding amine of Formula $H_2N$—$R_1$ or a salt thereof can be prepared in three steps by (i) protecting the amino group of 1-amino-2-methylpropan-2-ol with a suitable protecting group such as a Boc group, (ii) converting the hydroxy group into a fluoro group, and (iii) deprotecting the amino group. The fluorination in step (ii) can be carried out by combining the protected amino alcohol with (diethylamino) sulfur trifluoride in a suitable solvent such as dichloromethane. The reaction can be carried out at or below room temperature. The protection and deprotection steps can be carried out by conventional methods.

The syntheses of other useful amines of Formula $H_2N$—$R_1$, such as 2,2-dimethyl-3-(2-methyl-[1,3]dioxolan-2-yl)propylamine and tetrahydro-2H-pyran-4-ylmethylamine, have been reported; see, International Patent Application Publication No. WO2005/051317 (Krepski et al.) and U.S. Patent Application Publication No. 2004/0147543 (Hays et al.) Examples 477-480. These amines can be used to prepare compounds of Formula XIII wherein $R_1$ is a 2,2-dimethyl-4-oxopentyl, after ketal deprotection, or a tetrahydro-2H-pyran-4-ylmethyl group. Many other amines of Formula $H_2N$—$R_1$, such as, for example, substituted benzyl amines, are commercially available and can be used to make compounds of Formula XIII.

The reaction in step (1) and (1a) is conveniently carried out by combining a 2-chloroquinoline-3,4-diamine of Formula XIII with an isothiocyanate in the presence of a desulfurizing agent such as 1-[3-(dimethylamino)propyl]-3-ethylcarbodiimide hydrochloride and a base such as triethylamine. The reaction is carried out in a suitable solvent such as toluene or pyridine at an elevated temperature such as 80° C. Alternatively, to prepare compounds or salts of Formula XIV or XVI, wherein $R_{4a}$ or $R_2'$ is hydrogen, the reaction is conveniently carried out by adding cyanogen bromide to a solution of a 2-chloroquinoline-3,4-diamine of Formula XIII in a suitable solvent such as ethanol and heating at an elevated temperature such as 65° C. to 120° C., preferably 80° C. to 110° C. Optionally, a base such as triethylamine can be added.

In step (2) or (2a) of Reaction Scheme I, a 4-chloro-1H-imidazo[4,5-c]quinolin-2-amine of Formula XIV or XVI is aminated to provide a 1H-imidazo[4,5-c]quinoline-2,4-diamine of Formula XV or XVII, which are both subgenera of Formula I, II, and IV. The reaction is conveniently carried out by adding a solution of ammonia in a suitable solvent such as methanol to a compound of Formula XIV or XVI and heating the reaction at an elevated temperature such as 135° C. to 175° C., preferably 150° C. to 170° C.

Step (3) of Reaction Scheme I may be used to convert a compound of Formula XV to a compound of Formula XVa, wherein $R_{2a}$ is —$X_2$—$R_{5a}$ or —$X_2$—$N(R_{8a})$-$Q_a$-$R_{4a}$, using a variety of functional group transformations. For example, a compound of Formula XV wherein $R_{4a}$ is —$X_2$—$OCH_3$, which can be prepared by using an isothiocyanate in step (1) such as 2-methoxyethyl isothiocyanate or 3-methoxypropyl isothiocyanate, can be demethylated using conventional methods. The demethylation can be carried out by treating a compound of Formula XV wherein $R_{4a}$ is —$X_2$—$OCH_3$ with $BBr_3$ in a suitable solvent such as dichloromethane at a sub-ambient temperature such as −78° C. The resulting compound of Formula XV wherein $R_{4a}$ is —$X_2$—OH can be converted to a compound of Formula XV wherein $R_{4a}$ is —$X_2$—$NH_2$ by conversion of the hydroxy group to a leaving group such a methanesulfonate, treatment with sodium azide, and subsequent reduction using conventional methods. The compound of Formula XV wherein $R_{4a}$ is —$X_2$—$NH_2$ can be converted to a compound of Formula XVa using conventional methods. For example, a 1H-imidazo[4,5-c]quinoline-2,4-diamine wherein $R_{4a}$ is —$X_2$—$NH_2$ can react with an acid chloride of Formula $R_{4a}C(O)Cl$, a sulfonyl chloride of Formula $R_{4a}S(O)_2Cl$, or a sulfonic anhydride of Formula $(R_{4a}S(O)_2)_2O$ to provide a compound of Formula XVa wherein $R_{2a}$ is —$X_2$—$N(R_{8a})$-$Q_a$-$R_{4a}$ in which $Q_a$ is —C(O)— or —$S(O)_2$—. Numerous acid chlorides, sulfonyl chlorides, and sulfonic anhydrides are commercially available; others can be readily prepared using known synthetic methods. The reaction can be conveniently carried out by adding the acid chloride, sulfonyl chloride, or sulfonic anhydride to a solution of a compound of Formula XV wherein $R_{4a}$ is —$X_2$—$NH_2$ and a base such as triethylamine in a suitable solvent such as chloroform, dichloromethane, or acetonitrile. The reaction can be carried out at ambient temperature or a sub-ambient temperature such as 0° C.

Ureas of Formula XVa, wherein $R_{2a}$ is —$X_2$—$N(R_{8a})$-$Q_a$-$R_{4a}$ in which $Q_a$ is —$C(R_6)$—$N(R_{8a})$—W—, can be prepared by reacting a compound of Formula XV wherein $R_{4a}$ is —$X_2$—$NH_2$ with isocyanates of Formula $R_{4a}N$=C=O or carbamoyl chlorides of Formula $R_{4a}N$—$(R_{8a})$—C(O)Cl. Numerous isocyanates and carbamoyl chlorides are commercially available; others can be readily prepared using known synthetic methods. The reaction can be conveniently carried out as described above for the reaction with acid chlorides or sulfonyl chlorides. Alternatively, a compound of Formula XV wherein $R_{4a}$ is —$X_2$—$NH_2$ can be treated with an isocyanate of Formula $R_{4a}(CO)N$=C=O, a isothiocyanate of Formula $R_{4a}N$=C=S, or a sulfonyl isocyanate of Formula $R_{4a}S(O)_2N$=C=O to provide a compound of Formula XVa wherein $R_{4a}$ is —$X_2$—$N(R_{8a})$—$C(R_6)$—$N(R_{8a})$—$R_{4a}$, in which $R_6$, $R_{8a}$, and W are defined as above.

A 1H-imidazo[4,5-c]quinoline-2,4-diamine of Formula XV wherein $R_{4a}$ is —$X_2$—$NH_2$ can also be converted to a compound of Formula XVa, wherein $R_{2a}$ is —$X_2$—$R_{5a}$ by reaction with a chloroalkanesulfonyl chloride of Formula Cl—$R_{7a}S(O)_2Cl$ or a chloroalkanoyl chloride of Formula Cl—$R_{7a}C(O)Cl$, wherein $R_{7a}$ is as defined above. The reaction is conveniently carried out by adding the chloroalkanesulfonyl chloride or chloroalkanoyl chloride to a solution of the amine in a suitable solvent such as chloroform or dichloromethane in the presence of a base such as triethylamine at ambient temperature. The isolable intermediate chloroalkanesulfonamide or chloroalkanamide can then be treated with a base such as 1,8-diazabicyclo[5.4.0]undec-7-ene at ambient temperature in a suitable solvent such as N,N-dimethylformamide (DMF) to effect the cyclization to afford a compound of Formula XVa in which $R_{2a}$ is —$X_2$—$R_{5a}$.

In step (3a) of Reaction Scheme I, a 1H-imidazo[4,5-c]quinoline-2,4-diamine of Formula XVII is converted to a compound of Formula XVIII, a subgenus of Formulas I, II, and IV, using a variety of methods. For example, a 1H-imidazo[4,5-c]quinoline-2,4-diamine of Formula XVII can be converted to a compound of Formula XVIII, wherein $R_2$ is -$Q_2$-$R_{4a}$ by reaction with an acid chloride of Formula $R_{4a}C(O)Cl$ or Cl—$R_{7a}C(O)Cl$, a sulfonyl chloride of Formula $R_{4a}S(O)_2Cl$ or Cl—$R_{7a}S(O)_2Cl$, a sulfonic anhydride of Formula $(R_{4a}S(O)_2)_2O$, an isocyanate of Formula $R_{4a}N$=C=O, $R_{4a}(CO)N$=C=O, $R_{4a}N$=C=S, or $R_{4a}S(O)_2N$=C=O, or a carbamoyl chloride of Formula $R_{4a}N$—$(R_8)$—C(O)Cl according to the methods described above in step (3). Alternatively, a 1H-imidazo[4,5-c]quinoline-2,4-diamine of Formula XVII can be treated with a variety of arylalkylenyl or alkyl halides of in the presence of a base such as potassium carbonate in a suitable solvent such as DMF to provide a compound of Formula XVIII, wherein $R_2$ is $R_{4a}$. Numerous arylalkylenyl or alkyl halides are commercially available; others can be prepared by known methods. Some compounds of Formula XVIII wherein $R_2$ is $R_{4a}$ that are prepared in this step can be converted to compounds of Formula XVIII wherein $R_2$ is $R_{2a}$ according to the methods described above in step (3).

Reaction Scheme I

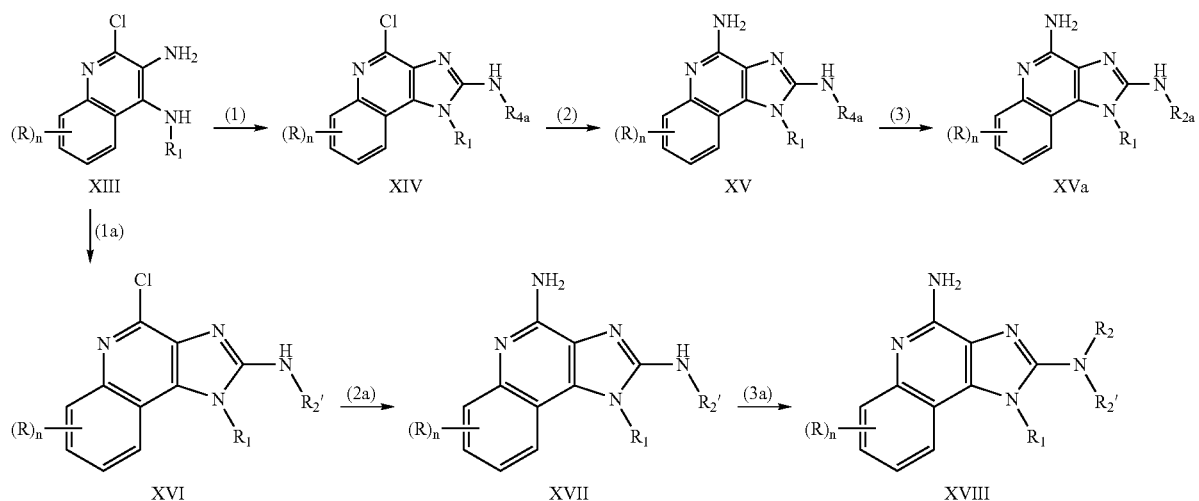

Compounds of the invention can also be prepared according to Reaction Scheme II, wherein R, $R_1$, $R_2$, $R_2'$, $R_{4a}$, $N(Bn)_2$, m, and n are as defined above, and D is —Br, —I, or —OCH$_2$Ph, wherein Ph is phenyl. In step (1) of Reaction Scheme II, a 3-nitroquinoline-2,4-diol of Formula XIX is converted to an amine-substituted quinolin-2-yltrifluoromethanesulfonate of Formula XX. The compound of Formula XIX wherein n and m are 0 is a commercially available compound, and other 3-nitroquinoline-2,4-diols of Formula XIX can be prepared from substituted anilines according to the methods described in Kohler et al, Chem. Ber. 60, p. 1108 (1927); Buckle et al, J. Med. Chem., 18, pp. 726-732 (1975), and Kappe et al, J. Heterocyclic Chem. 25, p. 857, (1988). Step (1) is conveniently carried out by adding two equivalents of trifluoromethanesulfonic anhydride to a solution of the 3-nitroquinoline-2,4-diol of Formula XIX in a suitable solvent such as dichloromethane in the presence of a base such as triethylamine. The reaction can be run at an elevated temperature, such as the reflux temperature of the solvent, and then cooled before the addition of one equivalent of an amine of Formula $R_1$—$NH_2$. The reaction can then be stirred at ambient temperature to provide a compound of Formula XX. The reaction can also be carried out under the conditions described in U.S. Pat. No. 5,395,937 (Nikolaides et al), and the intermediate 3-nitroquinoline-2,4-disulfonate can optionally be isolated before the reaction with the amine of Formula $R_1$—$NH_2$. Numerous amines of Formula $R_1$—$NH_2$ are commercially available; others can be prepared using known methods, including the methods described in Reaction Scheme I.

In step (2) of Reaction Scheme II, the trifluoromethanesulfonate group in a quinoline of Formula XX is displaced by an amine of Formula $HN(Bn)_2$ to provide quinoline of Formula XXI. The displacement is conveniently carried out by combining an amine of Formula $HN(Bn)_2$ and a compound of Formula XX in a suitable solvent such as toluene or xylenes in the presence of a base such as triethylamine and heating at an elevated temperature such as the reflux temperature of the solvent.

In step (3) of Reaction Scheme II, a compound of Formula XXI is reduced to provide a quinoline-2,3,4-triamine of Formula XXII. The reaction can be carried out by hydrogenation using platinum on carbon as the heterogeneous hydrogenation catalyst. The hydrogenation is conveniently carried out in a Parr apparatus in a suitable solvent such as toluene, methanol, acetonitrile, or ethyl acetate. The reaction can be carried out at ambient temperature. The reaction can be carried out using alternative methods as described in U.S. Pat. No. 5,395,937 (Nikolaides et al).

In step (4) of Reaction Scheme II, a quinoline-2,3,4-triamine of Formula XXII is cyclized to a 1H-imidazo[4,5-c]quinoline-2,4-diamine of Formula XXIII. The reaction is carried out according to the methods described in step (1) or (1a) of Reaction Scheme I.

In step (5) of Reaction Scheme II, the protecting groups are removed from the 4-amine of a compound of Formula XXIII to provide a 1H-imidazo[4,5-c]quinoline-2,4-diamine of Formula XXIV, a subgenus of Formulas I, II, and IV. The reaction is conveniently carried out by adding trifluoroacetic acid to a compound of Formula XXIII and heating at an elevated temperature such as 50-70° C.

In step (6) of Reaction Scheme II, a 1H-imidazo[4,5-c]quinoline-2,4-diamine of Formula XXIV is converted to a 1H-imidazo[4,5-c]quinoline-2,4-diamine of Formula XXV, a subgenus of Formulas I, II, and IV, using one or more of the methods described in step (3) and step (3a) of Reaction Scheme I.

In Reaction Scheme II, when m is 1, step (7) is used to convert a 1H-imidazo[4,5-c]quinoline-2,4-diamine of Formula XXV to a 1H-imidazo[4,5-c]quinoline-2,4-diamine of Formula IVe, a subgenus of Formulas I, II, and IV wherein $R_3$ is $R_{3a}$, using a variety of methods. When D is —Br or —I, compound of Formula XXIV can undergo known palladium-catalyzed coupling reactions such as the Suzuki coupling and the Heck reaction. For example, a bromine or iodine-substituted 1H-imidazo[4,5-c]quinoline-2,4-diamine of Formula XXV undergoes Suzuki coupling with a boronic acid of Formula $R_{3a}$—$B(OH)_2$, an anhydride thereof, or a boronic acid ester of Formula $R_{3a}$—$B(O$-alkyl$)_2$; wherein $R_{3a}$ is —$R_{4b}$, —$X_a$—$R_4$, —$X_b$—Y—$R_4$, or —$X_b$—$R_5$; where $X_a$ is alkenylene; $X_b$ is arylene, heteroarylene, and alkenylene interrupted or terminated by arylene or heteroarylene; $R_{4b}$ is aryl or heteroaryl where the aryl or heteroaryl groups can be unsubstituted or substituted as defined in $R_4$ above; and $R_4$, $R_5$, and Y are as defined above. The coupling is carried out by combining a compound of Formula XXV with a boronic acid or an ester or anhydride thereof in the presence of palladium (II) acetate, triphenylphosphine, and a base such as sodium carbonate in a suitable solvent such as n-propanol. The reaction can be carried out at an elevated temperature, for example, at the reflux temperature. Numerous boronic acids of Formula $R_{3a}$—B(OH)$_2$, anhydrides thereof, and boronic acid esters of Formula $R_{3a}$—B(O-alkyl)$_2$ are commercially available; others can be readily prepared using known synthetic methods.

The Heck reaction can also be used in step (7) of Reaction Scheme II to provide compounds of Formula IVe, wherein $R_3$ is —$X_a$—$R_{4b}$ and —$X_a$—Y—$R_4$. The Heck reaction is carried out by coupling a compound of Formula XXV with a compound of the Formula H$_2$C=C(H)—$R_{4b}$ or H$_2$C=C(H)—Y—$R_4$. Several of these vinyl-substituted compounds are commercially available; others can be prepared by known methods. The reaction is conveniently carried out by combining the compound of Formula XXV and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere.

Compounds of Formula IVe, wherein $R_3$ is —$X_c$—$R_4$, $X_c$ is alkynylene, and $R_4$ is as defined above, can also be prepared by palladium catalyzed coupling reactions such as the Stille coupling or Sonogashira coupling. These reactions are carried out by coupling a compound of Formula XXV with a compound of the Formula (alkyl)$_3$Sn—C≡C—$R_4$, (alkyl)$_3$Si—C≡C—$R_4$, or H—C≡C—$R_4$.

Compounds of Formula IVe prepared as described above by palladium-mediated coupling reactions, wherein $R_3$ is —$X_a$—$R_4$, —$X_a$—Y—$R_4$, —$X_{b2}$—Y—$R_4$, —$X_{b2}$—$R_5$, or —$X_c$—$R_4$, where $X_{b2}$ is alkenylene interrupted or terminated by arylene or heteroarylene, and $X_a$, $X_c$, Y, $R_4$, and $R_5$ are as defined above, can undergo reduction of the alkenylene or alkynylene group present to provide compounds of Formula IVe wherein $R_3$ is —$X_d$—$R_4$, —$X_d$—Y—$R_4$, —$X_e$—Y—$R_4$, or —$X_e$—$R_5$, where $X_d$ is alkylene; $X_e$ is alkylene interrupted or terminated by arylene or heteroarylene; and $R_4$, $R_5$, and Y are as defined above. The reduction can be carried out by hydrogenation using a conventional heterogeneous hydrogenation catalyst such as palladium on carbon. The reaction can conveniently be carried out on a Parr apparatus in a suitable solvent such as ethanol, methanol, or mixtures thereof.

Compounds of Formula XXV wherein D is —OCH$_2$Ph can be converted in step (7) to compounds of Formula IVe wherein $R_3$ is —O—$R_{4b}$, —O—X—$R_4$, —O—X—Y—$R_4$, or —O—X—$R_5$; wherein $R_4$, $R_{4b}$, $R_5$, X, and Y are as defined above. When D is —OCH$_2$Ph, step (7) is carried out in two parts. In part (i), the benzyl group in a benzyloxy-substituted 1H-imidazo[4,5-c]quinoline-2,4-diamine of Formula XXV is cleaved to provide a hydroxy group. The cleavage is conveniently carried out on a Parr apparatus under hydrogenolysis conditions using a suitable heterogeneous catalyst such as palladium or platinum on carbon in a solvent such as ethanol. Alternatively, the reaction can be carried out by transfer hydrogenation in the presence of a suitable hydrogenation catalyst. The transfer hydrogenation is conveniently carried out by adding ammonium formate to a solution of a compound of Formula XXV in a suitable solvent such as ethanol in the presence of a catalyst such as palladium on carbon. The reaction is carried out at an elevated temperature, for example, the refluxing temperature of the solvent.

In part (ii) of step (7) of Reaction Scheme II, a the hydroxy-substituted compound prepared in part (i) is converted to a compound of Formula IVe, wherein $R_3$ is —O—$R_{4b}$, —O—X—$R_4$, —O—X—Y—$R_4$, or —O—X—$R_5$, using a Williamson-type ether synthesis. The reaction is effected by treating a hydroxy-substituted 1H-imidazo[4,5-c]quinoline-2,4-diamine with an aryl, alkyl, or arylalkylenyl halide of Formula Halide-$R_{4b}$, Halide-alkylene-$R_4$, Halide-alkylene-Y—$R_4$, or Halide-alkylene-$R_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, and substituted fluorobenzenes. Other halides of these formulas can be prepared using conventional synthetic methods. The reaction is conveniently carried out by combining an alkyl, arylalkylenyl, or aryl halide with the hydroxy-substituted compound prepared in part (i) in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the halide reagent. Alternatively, part (ii) may be carried out using the Ullmann ether synthesis, in which an alkali metal aryloxide prepared from the hydroxy-substituted compound made in part (i) reacts with an aryl halide in the presence of copper salts, to provide a compound of Formula IVe, where $R_3$ is —O—$R_{4b}$, —O—$X_f$—$R_4$, or —O—$X_f$—Y—$R_4$, wherein $X_f$ is an arylene or heteroarylene. Numerous substituted and unsubstituted aryl halides are commercially available; others can be prepared using conventional methods.

Reaction Scheme II

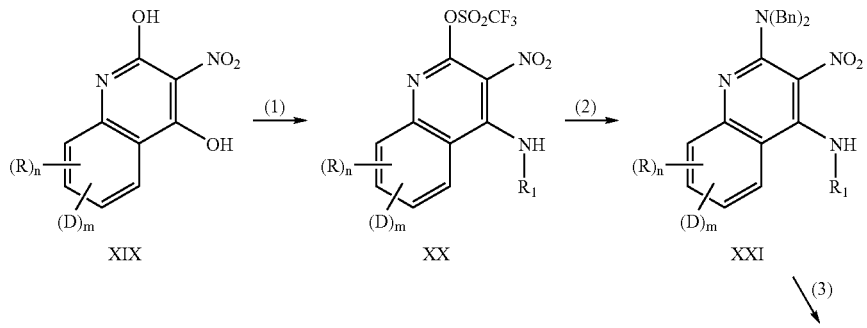

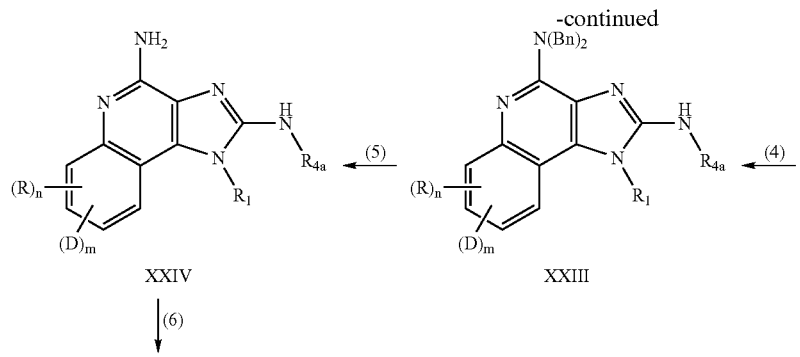

XXIV      XXIII      XXII

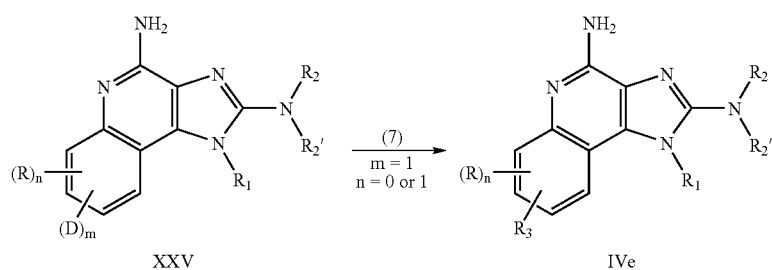

XXV      IVe

For some embodiments, compounds of the invention can undergo further synthetic elaboration using conventional methods. An example is shown in Reaction Scheme III, wherein R, $X_1$, $R_{4a}$, $N(Bn)_2$, and n are as defined above; Boc is tert-butoxycarbonyl; and $R_{1a}$ is —$X_1$—N($R_8$)-Q-,

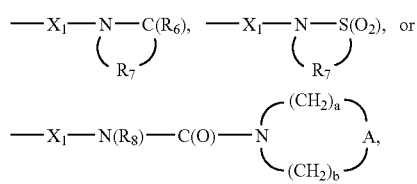

wherein $R_6$, $R_7$, $R_8$, Q, A, a and b are as defined above. Compounds of Formula XXVI can be prepared according to the methods described in Reaction Scheme II, wherein an amine of Formula Boc-NH—$X_1$—$NH_2$ is employed in step (1) of Reaction Scheme II.

In step (1) of Reaction Scheme III, the amine protecting groups are removed under acidic conditions. The conditions described in step (5) of Reaction Scheme II can be used to cleave both the Bn and Boc protecting groups to provide a 1-amino-substituted 1H-imidazo[4,5-c]quinoline-2,4-diamine of Formula XXVII, a subgenus of Formulas I, II, and IV.

In step (2) of Reaction Scheme III, the 1-amino group in a compound of Formula XXVII is treated with an acid chloride of Formula $R_4C(O)Cl$ or Cl—$R_7C(O)Cl$, a sulfonyl chloride of Formula $R_4S(O)_2Cl$ or Cl—$R_7S(O)_2Cl$, a sulfonic anhydride of Formula $(R_4S(O)_2)_2O$, an isocyanate of Formula $R_4N$=C=O, $R_4(CO)N$=C=O, $R_4N$=C=S, or $R_4S(O)_2$N=C=O, a carbamoyl chloride of Formula $R_4N$—($R_8$)—C(O)Cl or

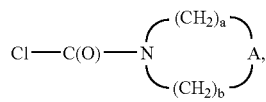

or a sulfamoyl chloride of Formula $R_4$—N($R_8$)—S(O)$_2$Cl according to the reaction conditions described in step (3) of Reaction Scheme I to provide an amide, sulfonamide, urea, or sulfamide. The product can be isolated as a 1H-imidazo[4,5-c]quinoline-2,4-diamine of Formula XXVIII, a subgenus of Formulas I, II, and IV, or as a pharmaceutically acceptable salt thereof.

Reaction Scheme III

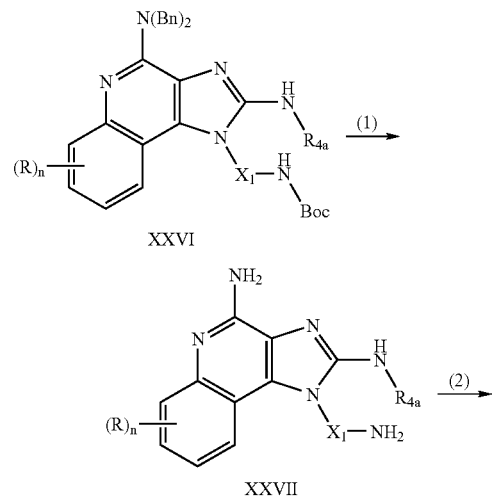

XXVI

XXVII

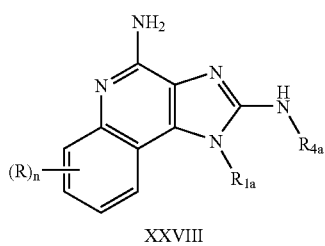

XXVIII

Imidazopyridine-2,4-diamines of the invention can be prepared according to Reaction Scheme IV, where $R_1$, $R_{A2}$, $R_{B2}$, Ph, $R_{4a}$, $R_2$, and $R_2'$ are as defined above. In step (1) of Reaction Scheme IV, a 2-phenoxypyridine-3,4-diamine of Formula XXIX is converted to a 4-phenoxy-1H-imidazo[4,5-c]pyridine of Formula XXX by reaction with a thiourea or cyanogen bromide. The reaction can be carried out as described in step (1) of Reaction Scheme I. Several 2-phenoxypyridine-3,4-diamines of Formula XXIX are known or can be prepared by published methods. See, for example, U.S. Pat. No. 6,545,016 (Dellaria et al); U.S. Pat. No. 6,743,920 (Lindstrom et al.), and U.S. Pat. No. 6,797,718 (Dellaria et al.).

In step (2) of Reaction Scheme IV, a 4-phenoxy-1H-imidazo[4,5-c]pyridine of Formula XXX is aminated to provide a 1H-imidazo[4,5-c]pyridine-2,4-diamine of Formula XXXI, a subgenus of Formulas I, II, and III. The reaction is conveniently carried out by adding a solution of ammonia in a suitable solvent such as methanol to a compound of Formula XXX and heating the reaction at an elevated temperature such as 170° C.

In step (3) of Reaction Scheme IV, a compound of Formula XXXI is converted to a compound of Formula XXXII using a variety of functional group transformations, for example, the methods described in steps (3) and (3a) of Reaction Scheme I. The product can be isolated as a compound of Formula XXXII, a subgenus of Formulas I, II, and III, or as a pharmaceutically acceptable salt thereof.

Reaction Scheme IV

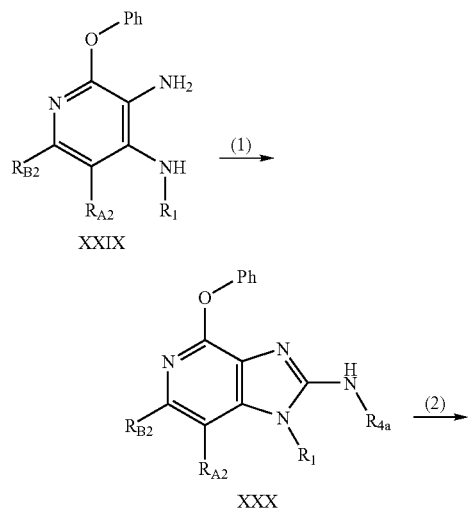

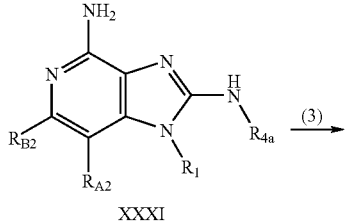

XXXI

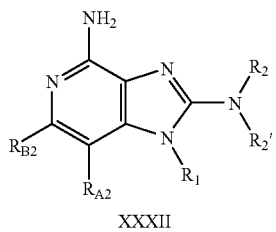

XXXII

Imidazo[4,5-c][1,5]naphthyridine-2,4-diamines of the invention can be prepared according to Reaction Scheme V, wherein D, R, $R_1$, $R_{4a}$, Ph, m, and p are as defined above. 3-Aminopyridine-2-carboxylic acids of Formula XXXIII are known and can be prepared by known methods. The compound where n and m are both 0 is commercially available. In step (1) of Reaction Scheme V, a 3-aminopyridine-2-carboxylic acid of Formula III is heated with acetic anhydride to provide a 2-methyl-4H-pyrido[3,2-d][1,3]oxazin-4-one of Formula XXXIV.

In step (2) of Reaction Scheme V a compound of Formula XXXIV is combined with sodium azide in a suitable solvent such as acetic acid to provide a tetraazolyl pyridine-2-carboxylic acid of Formula XXXV. The reaction conveniently may be run at ambient temperature.

In step (3) of Reaction Scheme V an acid of Formula XXXV is esterified by conventional methods to provide a compound of Formula XXXVI. The reaction is conveniently carried out by combining the acid of Formula XXXV with ethyl iodide in the presence of a base such as potassium carbonate in a suitable solvent such as acetone.

In step (4) of Reaction Scheme V a compound of Formula XXXVI is cyclized to provide a tetraazolo[1,5-a][1,5]naphthyridin-5-ol of Formula XXXVII. The reaction may be carried out by treating the compound of Formula XXXVI with an alkoxide base such as potassium ethoxide in a suitable solvent such as DMF. The reaction can be run at ambient temperature.

In step (5) of Reaction Scheme V a compound of Formula XXXVII is nitrated using a suitable nitrating agent such as nitric acid to provide a 4-nitrotetraazolo[1,5-a][1,5]naphthyridin-5-ol of Formula XXXVIII. The reaction is conveniently carried out by adding nitric acid to the compound of Formula XXXVII in a suitable solvent such as propionic acid and heating the mixture at an elevated temperature.

In step (6) of Reaction Scheme V the hydroxy group of a compound of Formula XXXVIII is converted to a trifluoromethanesulfonate to provide a compound of Formula XXXIX. The reaction is preferably carried out by combining a compound of Formula XXXVIII with a base, preferably a tertiary amine such as triethylamine, in a suitable solvent such as dichloromethane and then slowly adding trifluoromethanesulfonic anhydride. The addition is preferably carried out at a reduced temperature such as, for example, at about 0° C. The product can be isolated by conventional methods or it can be carried on without isolation as described below in connection with step (7).

In step (7) of Reaction Scheme V a compound of Formula XXXIX is reacted with an amine of formula $R_1$—$NH_2$ to provide a 4-nitrotetraazolo[1,5-a][1,5]naphthyridin-5-amine of Formula XL. The reaction can be carried out by adding the amine to the reaction mixture resulting from step (6). The reaction can also be carried out by adding the amine to a solution of the compound of Formula XXXIX and a tertiary amine such as triethylamine in a suitable solvent such as dichloromethane. The reaction may be run at ambient temperature.

In step (8) of Reaction Scheme V a compound of Formula XL is reduced to provide a tetraazolo[1,5-a][1,5]naphthyridin-4,5-diamine of Formula XLI. Preferably, the reduction is carried out using platinum on carbon as the heterogeneous hydrogenation catalyst. The reaction can conveniently be carried out on a Parr apparatus in a suitable solvent such as ethanol.

In step (9) of Reaction Scheme V a compound of Formula XLI is cyclized with a thiourea or cyanogen bromide to provide a 1H-tetraazolo[1,5-a]imidazo[4,5-c][1,5]naphthyridin-2-amine of Formula XLII. The cyclization reaction can be carried out according to the methods described in step (1) of Reaction Scheme I.

In step (10) of Reaction Scheme V a compound of Formula XLII is reacted with triphenylphosphine to provide a $N^4$-triphenylphosphinyl-1H-imidazo[4,5-c][1,5]naphthyridine-2,4-diamine of Formula XLIII. The reaction can be carried out by heating a compound of Formula XLII with triphenylphosphine in a suitable solvent such as 1,2-dichlorobenzene.

In step (11) of Reaction Scheme V a compound of Formula XLIII is hydrolyzed to provide a 1H-imidazo[4,5-c][1,5] naphthyridine-2,4-diamine of Formula XLIV, which is a subgenus of Formulas I, II, and VI. The hydrolysis can be carried out by conventional methods such as by heating in a lower alkanol in the presence of an acid.

In Reaction Scheme V, when m is 1, step (12) is used to convert a 1H-imidazo[4,5-c][1,5]naphthyridine-2,4-diamine of Formula XLIV to a 1H-imidazo[4,5-c][1,5]naphthyridine-2,4-diamine of Formula XLV, a subgenus of Formulas I, II, and VI, using one of the methods described in step (7) of Reaction Scheme II.

Reaction Scheme V

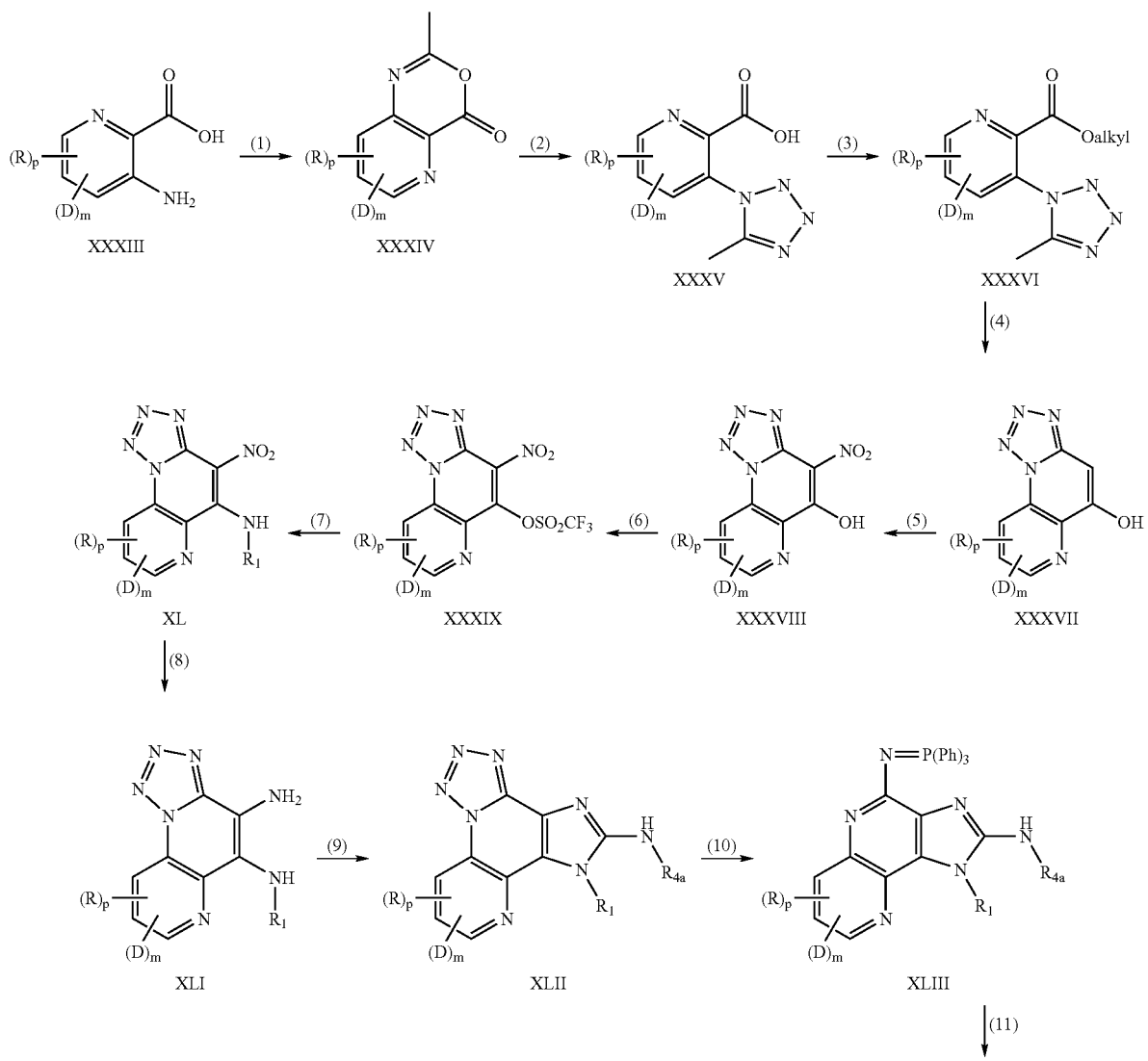

-continued

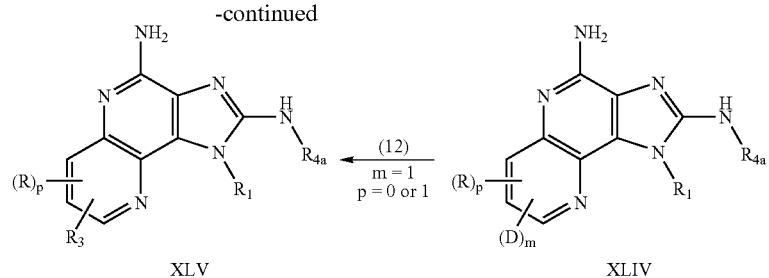

The methods shown in Reaction Scheme V and the methods described in U.S. Pat. No. 6,194,425 (Gerster et al) can be used to make other positional isomers of naphthyridines of Formula XLIV or XLV when a 2-aminonicotinic acid or a 3-aminoisonicotinic acid is used as the starting material instead of a compound of Formula XXXIII.

Compounds of the invention can also be prepared according to Reaction Scheme VI, wherein $R_b$ is alkyl, alkoxy, or —N($R_9$)$_2$; E is carbon (imidazoquinoline ring system) or nitrogen (imidazonaphthyridine ring system); n is an integer from 0 to 4 (imidazoquinoline ring system) or 0 to 3 (imidazonaphthyridine ring system); $R_2'$ is as defined above; and $R_{2b}$ and $R_{1b}$ are subsets of $R_2$ and $R_1$ as defined above that do not include those substituents that one skilled in the art would recognize as being susceptible to reduction under the acidic hydrogenation conditions of the reaction. These susceptible groups include, for example, alkenyl, alkynyl, and aryl groups and groups bearing nitro substituents.

As shown in Reaction Scheme VI, an 1H-imidazo[4,5-c]quinoline-2,4-diamine or 1H-imidazo[4,5-c][1,5]naphthyridine-2,4-diamine of Formula XLVI can be reduced to a 6,7,8,9-tetrahydroquinoline or tetrahydronaphthyridine of Formula XLVII. Compounds of Formula XLVI can be prepared according to the methods described in Reaction Schemes I, II, III, or V. The reaction is conveniently carried out under hetereogeneous hydrogenation conditions by adding platinum (IV) oxide to a solution of the compound of Formula XLVI in trifluoroacetic acid and placing the reaction under hydrogen pressure. The reaction can be carried out on a Parr apparatus at ambient temperature.

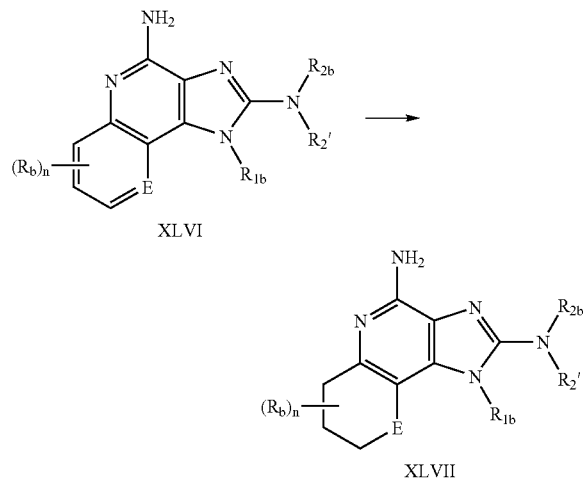

For certain embodiments, compounds of the invention can be prepared according to Reaction Scheme VII, wherein D, E, R, $R_1$, $R_3$, $R_{4a}$, $Q_a$, and m are as defined above; n is an integer from 0 to 4 (imidazoquinoline ring system) or 0 to 3 (imidazonaphthyridine ring system) with the proviso that when m is 1, n is 0 or 1; $R_{6x}$ is O or S; and $R_{11}$ is —C(O)—O—$C_{1-4}$ alkyl or hydrogen. In step (1) of Reaction Scheme I, a quinoline- or [1,5]naphthyridine-3,4-diamine of Formula XLVIII is reacted with a compound of Formula XLIX to provide a compound of Formula L. The reaction can be conveniently carried out under by combining a compound of Formula XLIX with a diamine of Formula XLVIII in a suitable solvent such as a lower alcohol or chloroform in the presence of an acid such as acetic acid, p-toluenesulfonic acid monohydrate, or a combination thereof. If cyclization and imidazole-ring formation does not occur under acidic conditions to provide a compound of Formula L, the uncyclized intermediate can be treated with a base such as sodium methoxide in a suitable solvent such as methanol to effect the cyclization. The reaction in step (1) of Reaction Scheme I may also be carried out according to the method of Kukla, M. J. et al., *J. Med. Chem.*, 34, pp. 3187-3197 (1991) or Elliott et al., *J. Org. Chem.*, 62, pp. 8071-8075, (1997).

Many compounds of Formula XLVIII are known and can be readily prepared using known synthetic routes; see for example, U.S. Pat. No. 4,689,338 (Gerster), U.S. Pat. No. 4,929,624 (Gerster et al.), U.S. Pat. No. 5,268,376 (Gerster), U.S. Pat. No. 5,389,640 (Gerster et al.), U.S. Pat. No. 6,194,425 (Gerster et al.), U.S. Pat. No. 6,331,539 (Crooks et al.), U.S. Pat. No. 6,451,810 (Coleman et al.), U.S. Pat. No. 6,541,485 (Crooks et al.) U.S. Pat. No. 6,660,747 (Crooks et al.), U.S. Pat. No. 6,670,372 (Charles et al.), U.S. Pat. No. 6,683,088 (Crooks et al.), U.S. Pat. No. 6,656,938 (Crooks et al.), and U.S. Pat. No. 6,664,264 (Dellaria et al.), U.S. Patent Application Publication No. 2004/0147543 (Hays et al.), and International Patent Application Publication Nos. WO2005/020999 (Lindstrom et al.) and WO2005/051317 (Krepski et al.).

Compounds of Formula XLIX are known or can be prepared by known methods. For example, compounds where -$Q_a$- is —C(O)—O— can be prepared by combining O-methylisourea or S-methylisothiourea or a salt thereof with one or two equivalents of a chloroformate, for example, methyl chloroformate in a suitable solvent such as 1,2-dichloroethane in the presence of a base such as pyridine. For some compounds, the reaction may be carried out in water in the presence of a base such as sodium hydroxide. The reaction can be carried out at room temperature. The preparation of compounds wherein -$Q_a$-$R_{4a}$ is —C(O)—O—$CH_3$ have been reported in Skibinski et al., *J. Appl. Chem.*, 37, pp. 291-294 (1993), Hamprecht, G. et al, *Liebigs Ann. Chem.*, 12, pp. 2363-2370 (1985), Viswananthan, N. Indian Patent 168,784; *Chem. Abstr.* 118, 22237, (1993), and U.S. Pat. No. 4,026,936

(Lauer and Walser). The preparation of compounds where -$Q_a$-$R_{4a}$ is —C(O)—$CH_3$ or —S(O)$_2$—$CH_3$ has also been reported; see, Williams, et al., *J. Antibiot.*, 2, pp. 189-201, (1998).

In step (2) of Reaction Scheme VII, a 1H-imidazo[4,5-c] quinoline or 1H-imidazo[4,5-c][1,5]naphthyridine of Formula L is oxidized to provide a 1H-imidazo[4,5-c]quinoline-5N-oxide or 1H-imidazo[4,5-c][1,5]naphthyridine-5N-oxide of Formula LI using a conventional oxidizing agent capable of forming N-oxides. The reaction is conveniently carried out by adding 3-chloroperoxybenzoic acid to a solution of a compound of Formula L in a solvent such as chloroform or dichloromethane. The reaction can be carried out at room temperature.

In step (3) of Reaction Scheme VII, a 1H-imidazo[4,5-c]quinoline-5N-oxide or 1H-imidazo[4,5-c][1,5]naphthyridine-5N-oxide of Formula LI is aminated to provide a 1H-imidazo[4,5-c]quinolin-4-amine or 1H-imidazo[4,5-c][1,5]naphthyridin-4-amine of Formula LII, a subgenus of Formulas I and II. Step (3) involves the activation of an N-oxide of Formula LI by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide to a solution of the N-oxide of Formula LI in a suitable solvent such as dichloromethane or chloroform and then adding p-toluenesulfonyl chloride or benzenesulfonyl chloride. The reaction can be carried out at room temperature.

Alternatively, the oxidation and amination can be carried out as a one-pot procedure without isolating the N-oxide of Formula LI by adding 3-chloroperoxybenzoic acid to a solution of a compound of Formula L in a solvent such as dichloromethane or chloroform and then adding ammonium hydroxide and p-toluenesulfonyl chloride or benzenesulfonyl chloride.

In Reaction Scheme VII, when m is 1, step (4) can be used to convert a compound of Formula LII to a 1H-imidazo[4,5-c]quinoline-2,4-diamine or 1H-imidazo[4,5-c][1,5]naphthyridine-2,4-diamine of Formula LIII, a subgenus of Formulas I and II in which $R_3$ is $R_{3a}$, using one of the methods described in step (7) of Reaction Scheme II.

Carbamates of Formula LII, wherein -$Q_a$-$R_{4a}$ is —C(O)—O—$CH_3$, are also useful precursors to 1H-imidazo[4,5-c]quinoline-2,4-diamines of Formula XVIII wherein both $R_2$ and $R_2'$ are hydrogen. The 2-amino substituted compound can be prepared by treating a carbamate of Formula LII with potassium hydroxide in water at an elevated temperature or with hydrogen bromide in acetic acid at room temperature.

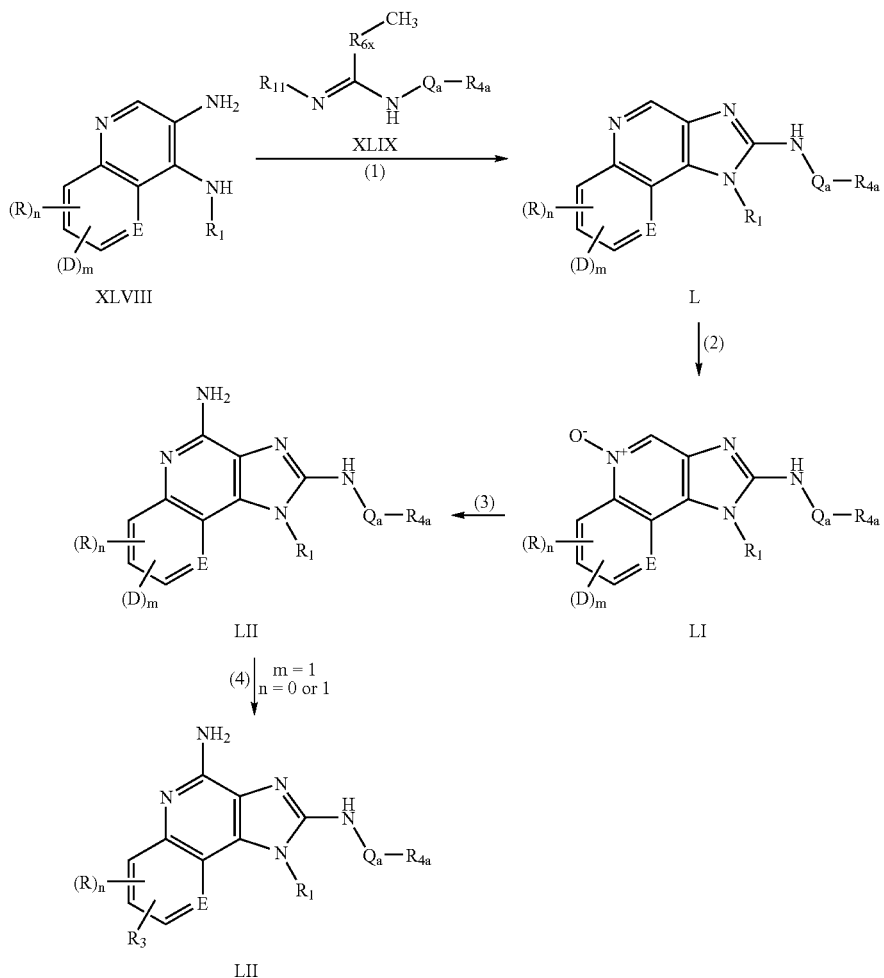

Reaction Scheme VII

Compounds of the invention can also be prepared using variations of the synthetic routes shown in Reaction Schemes I through VII that would be apparent to one of skill in the art. For example, the method of step (1) of Reaction Scheme VII can be used with starting materials of Formula XIII, XXIII, XXIX, or XLI to prepare compounds of the invention. Compounds of the invention can also be prepared using the synthetic routes described in the EXAMPLES below.

Prodrugs can be prepared in a variety of ways. For example, a compound wherein $R_1$ is —$X_1$—OH (e.g. hydroxyalkyl) can be converted into a prodrug wherein $R_1$ is, for example, —$X_1$—O—C($R_6$)—$R_4$, —$X_1$—O—C($R_6$)—O—$R_4$, or —$X_1$—O—C($R_6$)—N($R_8$)—$R_4$, wherein $X_1$, $R_4$, $R_6$, and $R_8$ are as defined above, using methods known to one skilled in the art. In addition, a compound wherein R is hydroxy may be converted to an ester, an ether, a carbonate, or a carbamate. For compounds containing an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N-($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$ alkyl)$_2$, $C_{1-6}$ alkoxycarbonyl, $C_{1-6}$ alkylcarbamoyl, and α-aminoacyl or α-aminoacyl-α-aminoacyl, where each α-aminoacyl group is independently selected from racemic, D, and L-amino acids. For compounds containing an alcohol functional group, particularly useful prodrugs are esters made from carboxylic acids containing one to six carbon atoms, unsubstituted or substituted benzoic acid esters, or esters made from naturally occurring L-amino acids.

Prodrugs can also be made from a compound containing an amino group by conversion of the amino group to a functional group such as an amide, carbamate, urea, amidine, or another hydroylizable group using conventional methods. A prodrug of this type can be made by the replacement of a hydrogen atom in an amino group, particularly the amino group at the 4-position, with a group such as —C(O)—R″, α-aminoacyl, α-aminoacyl-α-aminoacyl, —C(O)—O—R″, —C(O)—N(R″″)—R″, —C(=NY″)—R″, —CH(OH)—C(O)—OY′, —CH(O$C_{1-4}$ alkyl)$Y_0$, —CH$_2Y_3$, or —CH(CH$_3$)$Y_3$; wherein R″ and R″″ are each independently $C_{1-10}$ alkyl, $C_{3-7}$ cycloalkyl, or benzyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$; with the proviso that R″″ may also be hydrogen; each α-aminoacyl group is independently selected from racemic, D, or L-amino acids; Y′ is hydrogen, $C_{1-6}$ alkyl, or benzyl; $Y_0$ is $C_{1-6}$ alkyl, carboxy$C_{1-6}$ alkylenyl, amino$C_{1-4}$ alkylenyl, mono-N-$C_{1-6}$ alkylamino$C_{1-4}$ alkylenyl, or di-N,N-$C_{1-6}$ alkylamino$C_{1-4}$ alkylenyl; and $Y_3$ is mono-N-$C_{1-6}$ alkylamino, di-N,N-$C_{1-6}$ alkylamino, morpholin-4-yl, piperidin-1-yl, pyrrolidin-1-yl, or 4-$C_{1-4}$ alkylpiperazin-1-yl. For compounds containing an amine functional group, particularly useful prodrugs are amides derived from carboxylic acids containing one to ten carbon atoms, amides derived from amino acids, and carbamates containing one to ten carbon atoms.

Pharmaceutical Compositions and Biological Activity

Pharmaceutical compositions of the invention contain a therapeutically effective amount of a compound of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, cytokine inhibition, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of certain compounds or salts according to the invention include tumor necrosis factor-α (TNF-α). Among other effects, inhibition of TNF-α production can provide prophylaxis or therapeutic treatment of diseases in animals in which TNF is mediated, making the compounds or salts useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, *hemophilus influenza* b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of Formula I, II, III, IV, V, VI, VII, VIII, any of the embodiments described herein, or a combination thereof to the animal. An animal may also be vaccinated by administering an effective amount of a compound or salt of Formula I, II, III, IV, V, VI, VII, VIII, any of the embodiments described herein, or a combination thereof to the animal as a vaccine adjuvant. In one embodiment, there is provided a method of vaccinating an animal comprising administering an effective amount of a compound or salt described herein to the animal as a vaccine adjuvant.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography was carried out using a COMBIFLASH system (an automated high-performance flash purification product available from Teledyne Isco, Inc., Lincoln, Nebr., USA), a HORIZON HPFC system (an automated high-performance flash purification product available from Biotage, Inc, Charlottesville, Va., USA) or a combination thereof. For some of these purifications, either a FLASH 40+M silica cartridge or a FLASH 65I silica cartridge (both available from Biotage, Inc, Charlottesville, Va., USA) was used. The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

1-(2-Methylpropyl)-1H-imidazo[4,5-c]quinoline-2,4-diamine

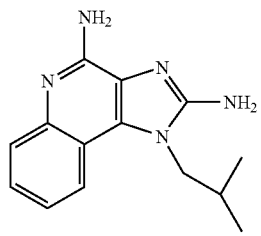

Part A

A solution of 2-chloro-$N^4$-(2-methylpropyl)-3,4-quinolinediamine (André et al, U.S. Pat. No. 4,988,815, Example 6, 8.92 g, 35.7 mmol) in ethanol (50 mL) was stirred at 100° C.; cyanogen bromide (5.67 g, 53.5 mmol) was added in one portion. The red solution was stirred overnight, washed three times with water, and washed once with brine. A precipitate formed in the aqueous washings and was isolated by filtration. The organic fraction was dried over magnesium sulfate, filtered through a layer of CELITE filer agent, concentrated under reduced pressure, further dried under high vacuum, and combined with the isolated precipitate to provide 9.81 g of 4-chloro-1-(2-methylpropyl)-1H-imidazo[4,5-c]quinoline-2-amine hydrobromide as a dark red solid.

Part B

4-Chloro-1-(2-methylpropyl)-1H-imidazo[4,5-c]quinoline-2-amine hydrobromide (8.61 g) and ammonia (131 mL of a 7 N solution in methanol) were added to a high-pressure vessel, which was sealed and heated overnight in an oven at 150° C. The resulting solution was concentrated under reduced pressure to provide 7 g of crude product. A portion of the product was purified by flash chromatography on silica gel (eluting with 3-4% methanol in dichloromethane with 1% ammonium hydroxide added.) The isolated product was washed with methanol, purified again by flash chromatography using the same conditions, and dried under high vacuum to provide 1-(2-methylpropyl)-1H-imidazo[4,5-c]quinoline-2,4-diamine as a gray, crystalline solid, mp >250° C. Anal. calcd. for $C_{14}H_{17}N_5$: C, 65.68; H, 6.71; N, 27.43. Found: C, 65.69; H, 6.79; N, 27.42.

Example 2

1-(2,4-Diamino-1H-imidazo[4,5-c]quinolin-1-yl)-2-methylpropan-2-ol hydrobromide

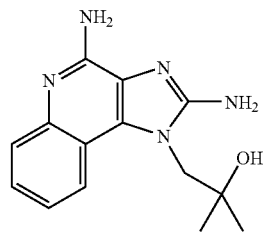

Part A

Cyanogen bromide (4.78 g, 45.2 mmol) was added to a solution of 1-[(3-amino-2-chloro-4-quinolinyl)amino]-2-methyl-2-propanol (André et al, U.S. Pat. No. 4,988,815, Example 13, 10.0 g, 37.6 mmol) in ethanol (200 mL), and the solution was heated overnight at 90° C. and allowed to cool to ambient temperature. A precipitate formed and was isolated by filtration, washed once with diethyl ether, and then washed several times with dichloromethane to provide 9.28 g of 1-(4-chloro-2-amino-1H-imidazo[4,5-c]quinolin-1-yl)-2-methylpropan-2-ol hydrobromide as a gray powder.

Part B 1-(4-Chloro-2-amino-1H-imidazo[4,5-c]quinolin-1-yl)-2-methylpropan-2-ol hydrobromide (2.00 g, 5.38 mmol) and ammonia (50 mL of a 7 N solution in methanol) were added to a high-pressure vessel, which was sealed and heated overnight in an oven at 150° C. The solvent was removed under reduced pressure, and the residue was suspended in acetonitrile, isolated by filtration, washed with warm acetonitrile (2×100 mL), washed with diethyl ether (100 mL), washed with methanol, and dried under high vacuum to provide 1.02 g of 1-(2,4-diamino-1H-imidazo[4,5-c]quinolin-1-yl)-2-methylpropan-2-ol hydrobromide as a white powder, mp >230° C.

Anal. calcd. for $C_{14}H_{17}N_5O \cdot 0.8HBr$: C, 50.04; H, 5.34; N, 20.84. Found: C, 49.64; H, 5.47; N, 21.00.

Example 3

N-[2-(2,4-Diamino-1H-imidazo[4,5-c]quinolin-1-yl)-1,1-dimethylethyl]methanesulfonamide

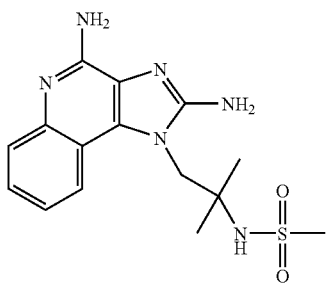

Part A

Triethylamine (75 mL, 0.54 mol) was slowly added to a solution of 2,4-dichloro-3-nitroquinoline (André et al, U.S. Pat. No. 4,988,815, Example 2, 114 g, 0.470 mol) in anhydrous 1-methyl-2-pyrrolidinone (NMP) (450 mL), and the resulting black solution was cooled to 0° C. A solution of 1,2-diamino-2-methylpropane (42 g, 0.54 mol) in anhydrous NMP (42 mL) was added dropwise over a period of three hours. After the addition was complete, the reaction was allowed to warm to ambient temperature, stirred for five hours, and poured slowly into warm water (4 L) with vigorous stirring. A yellow precipitate formed, and the suspension was stirred for one hour at ambient temperature. The precipitate was isolated by filtration and washed with cold water until the filtrate was colorless. The solid was dissolved in dichloromethane (4 L), and the resulting solution was washed sequentially with saturated aqueous sodium carbonate and brine, dried over magnesium sulfate and sodium sulfate, filtered through a layer of CELITE filter agent, and concentrated under reduced pressure to provide 130 g of $N^1$-(2-chloro-3-nitroquinolin-4-yl)-2-methylpropane-1,2-diamine as a bright yellow powder.

Part B

Triethylamine (1.77 mL, 12.7 mmol) was added to a solution of $N^1$-(2-chloro-3-nitroquinolin-4-yl)-2-methylpropane-1,2-diamine (2.5 g, 8.5 mmol) in dichloromethane (25 mL), and the resulting solution was cooled to 0° C. and stirred for five minutes. Methanesulfonyl chloride (1.07 g, 9.33 mmol) was added in portions over a period of five minutes, and the reaction was allowed to warm to ambient temperature and stirred overnight. An analysis by high-performance liquid chromatography (HPLC) indicated the reaction was incomplete, and additional methanesulfonyl chloride (0.5 equivalent) was added. The reaction was stirred for two hours and again determined to be incomplete. Additional methanesulfonyl chloride (0.5 equivalent) and triethylamine (1.5 equivalents) were added, and the reaction was stirred for two hours and then diluted with dichloromethane. The resulting solution was washed twice with brine and twice with saturated aqueous sodium bicarbonate, dried over magnesium sulfate, filtered, and concentrated under reduced pressure to provide 3.1 g of N-{2-[(2-chloro-3-nitroquinolin-4-yl)amino]-1,1-dimethylethyl}methanesulfonamide as a yellow solid.

Part C

N-{2-[(2-Chloro-3-nitroquinolin-4-yl)amino]-1,1-dimethylethyl}methanesulfonamide (3.1 g, 8.3 mmol), 5% platinum on carbon (310 mg), and acetonitrile (40 mL) were added to a Parr vessel and shaken under hydrogen pressure (50 psi, $3.4 \times 10^5$ Pa) for four hours. An analysis by HPLC indicated the presence of starting material, and additional platinum on carbon (310 mg) was added. The reaction was shaken under hydrogen pressure overnight and filtered through a layer of CELITE filter agent. The filter cake was washed with dichloromethane, and the filtrate was concentrated under reduced pressure to provide 2.55 g of N-{2-[(3-amino-2-chloroquinolin-4-yl)amino]-1,1-dimethylethyl}methanesulfonamide as a dark oil, which was used without purification.

Part D

Cyanogen bromide (0.945 g, 8.93 mmol) was added to a solution of N-{2-[(3-amino-2-chloroquinolin-4-yl)amino]-1,1-dimethylethyl}methanesulfonamide (2.55 g, 7.44 mmol) in ethanol (25 mL), and the solution was stirred at ambient temperature for two hours. An analysis by HPLC indicated that no reaction had taken place, and the reaction was then heated overnight at 90° C. and allowed to cool to ambient temperature. Water was added; a precipitate was present and was isolated by filtration and washed with diethyl ether to provide 510 mg of N-[2-(2-amino-4-chloro-1H-imidazo[4,5-c]quinolin-1-yl)-1,1-dimethylethyl]methanesulfonamide hydrobromide as a brown solid. The filtrate was concentrated under reduced pressure, and the residue was dissolved in methanol. Diethyl ether was added, and a gummy precipitate formed, which was dissolved again in methanol and concentrated under reduced pressure to provide an additional 1.1 g of the product as a dark brown solid.

Part E

Crude N-[2-(2-amino-4-chloro-1H-imidazo[4,5-c]quinolin-1-yl)-1,1-dimethylethyl]methanesulfonamide hydrobromide (0.400 g) and ammonia (25 mL of a 7 N solution in methanol) were added to a high-pressure vessel, which was sealed and heated overnight in an oven at 150° C. The resulting solution was concentrated under reduced pressure, and the residue was purified by flash chromatography on silica gel (eluting with 2-6% methanol in dichloromethane with 1% ammonium hydroxide added.) A portion of the product was recrystallized from acetonitrile and a small amount of methanol, isolated by filtration, and washed with diethyl ether to provide 39 mg of N-[2-(2,4-diamino-1H-imidazo[4,5-c]quinolin-1-yl)-1,1-dimethylethyl]methanesulfonamide as brown needles, mp >230° C.

Anal. calcd. for $C_{15}H_{20}N_6O_2S$: C, 51.71; H, 5.79; N, 24.12. Found: C, 51.61; H, 5.71; N, 24.17.

Example 4

1-Benzyl-1H-imidazo[4,5-c]quinoline-2,4-diamine

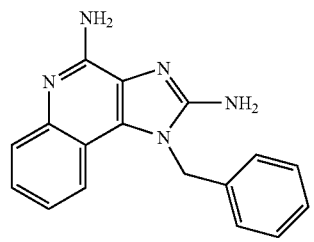

Part A

A solution of 2,4-dichloro-3-nitroquinoline (25 g, 0.10 mol) in N,N-dimethylformamide (DMF) (130 mL) was cooled to 0° C. Triethylamine (17.2 mL, 0.123 mol) and benzylamine (11.2 mL, 0.10 mol) were sequentially added, and the reaction was stirred at ambient temperature overnight. The reaction was poured into water (1 L), and the suspension was stirred for 30 minutes at ambient temperature. The resulting precipitate was isolated by filtration and washed with water to provide 31.92 g of N-benzyl-2-chloro-3-nitroquinolin-4-amine as a bright yellow powder.

Part B

N-Benzyl-2-chloro-3-nitroquinolin-4-amine (31.9 g, 0.102 mol), 5% platinum on carbon (3.2 g), and acetonitrile (325 mL) were added to a Parr vessel and shaken under hydrogen pressure (30 psi, $2.1 \times 10^5$ Pa) overnight. The mixture was filtered through a layer of CELITE filter agent, and the filtrate was concentrated under reduced pressure and further dried under high vacuum to provide 27.82 g of $N^4$-benzyl-2-chloroquinoline-3,4-diamine, which was used without purification.

Part C

Cyanogen bromide (2.2 g, 21 mmol) was added to a solution of $N^4$-benzyl-2-chloroquinoline-3,4-diamine (5.0 g, 17 mmol) in ethanol (50 mL), and the solution was heated at 90° C. for two hours. An analysis by liquid chromatography/mass spectrometry (LC/MS) indicated the presence of starting material. Additional cyanogen bromide (2.2 g, 21 mmol) was added, and the reaction was stirred for one hour at 90° C., stirred for three days at 50° C., and allowed to cool to ambient temperature. The solvent was removed under reduced pressure, and the resulting solid was washed with diethyl ether (1 L) to provide 6.84 g of 1-benzyl-4-chloro-1H-imidazo[4,5-c]quinoline-2-amine hydrobromide as a dark gray powder.

Part D

Crude 1-benzyl-4-chloro-1H-imidazo[4,5-c]quinoline-2-amine hydrobromide (0.500 g) and ammonia (20 mL of a 7 N solution in methanol) were added to a high-pressure vessel, which was sealed and heated in an oven at 170° C. for six days. The resulting solution was concentrated under reduced pressure, and the residue was purified by automated flash chromatography on silica gel (eluting with 0-10% methanol in dichloromethane with 1% ammonium hydroxide added) to provide 42 mg of 1-benzyl-1H-imidazo[4,5-c]quinoline-2,4-diamine as a brown powder, mp 254-256° C.

Anal. calcd. for $C_{17}H_{15}N_5 \cdot 0.7H_2O$: C, 67.62; H, 5.47; N, 23.19. Found: C, 67.67; H, 5.33; N, 22.92.

Example 5

$N^2$-Methyl-1-(2-methylpropyl)-1H-imidazo[4,5-c]quinoline-2,4-diamine

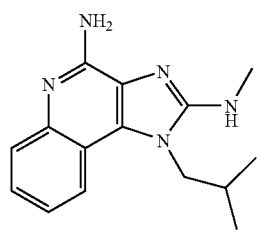

Part A

4-Methoxybenzylamine (40 g, 290 mmol) was cooled to 0° C., and p-anisaldehyde (39.7 g, 292 mmol) was added dropwise. The reaction was stirred at ambient temperature for two hours, concentrated under reduced pressure, and further dried under high vacuum overnight to provide 97 g of N-(4-methoxybenzyl)-N-[(4-methoxyphenyl)methylidene]amine as a white, waxy solid.

Part B

A solution of the material from Part A in ethanol (300 mL) was cooled to 0° C. and stirred rapidly. Solid sodium borohydride (22.1 g, 584 mmol) was added slowly over a period of several minutes, and the reaction was stirred at ambient temperature for two hours. Water (300 mL) was added, and the resulting mixture was shaken and allowed to stand overnight. The mixture was extracted with diethyl ether (3×100 mL), and the combined extracts were washed with water (200 mL), dried over magnesium sulfate, filtered through a layer of CELITE filter agent, concentrated under reduced pressure, and further dried under high vacuum to provide 67 g of N,N-bis(4-methoxybenzyl)amine as a white solid.

Part C

Triethyl amine (40.4 mL, 0.290 mol) and N,N-bis(4-methoxybenzyl)amine (62.0 g, 242 mmol) were sequentially added to a solution of [4-(2-methylpropyl)amino-3-nitroquinolin-2-yl]trifluoromethanesulfonate (Nikolaides et al, U.S. Pat. No. 5,395,937, Example 1, 95.0 g, 242 mmol) in toluene (300 mL) at ambient temperature. The solution was stirred at ambient temperature for a few minutes, heated at reflux for two hours, and allowed to cool to ambient temperature. Ethyl acetate and saturated aqueous sodium bicarbonate (300 mL) were added. The organic layer was separated and washed twice with saturated aqueous sodium bicarbonate. The combined aqueous fractions were filtered to remove a solid, and the filtrate was extracted with ethyl acetate (3×150 mL). The combined extracts were washed once with saturated aqueous sodium bicarbonate. All organic fractions were then combined and dried over magnesium sulfate, filtered through a layer of CELITE filter agent, concentrated under reduced pressure, and further dried under high vacuum for three days to provide $N^2,N^2$-bis(4-methoxybenzyl)-$N^4$-(2-methylpropyl)-3-nitroquinoline-2,4-diamine as a red oil, which was used without purification.

Part D

A portion of the crude material from Part C (218 g), 5% platinum on carbon (15 g), and acetonitrile (500 mL) were added to a Parr vessel and shaken under hydrogen pressure (45 psi, $3.1 \times 10^5$ Pa) overnight. An analysis by LC/MS indicated the presence of starting material, and additional 5% platinum on carbon (5 g) was added. The reaction was shaken under hydrogen pressure overnight, filtered, and concentrated under reduced pressure to provide 194 g of $N^2,N^2$-bis(4-methoxybenzyl)-$N^4$-(2-methylpropyl)quinoline-2,3,4-triamine as a red oil, which was used without purification.

Part E

Triethylamine (57 mL, 408 mmol) and methyl isothiocyanate (18 g, 245 mmol) were sequentially added to a suspension of a portion of the material from Part D (96 g crude) in toluene (100 mL), and the reaction was heated for one hour at 80° C. 1,(3-Dimethylaminopropyl)-3-ethylcarbodiimide hydrochloride (38 g, 245 mmol) was added slowly, and the reaction was heated at 80° C. for two hours, allowed to cool to ambient temperature, and concentrated under reduced pressure. The residue was dissolved in ethyl acetate, and the resulting solution was washed with saturated aqueous sodium bicarbonate, dried over magnesium sulfate, filtered, and concentrated under reduced pressure to provide a brown liquid. The crude product was purified by column chromatography on silica gel (eluting sequentially with 50% ethyl acetate in hexane and 10% methanol in ethyl acetate containing 1% ammonium hydroxide) to provide 15 g of $N^4,N^4$-bis(4-methoxybenzyl)-$N^2$-methyl-1-(2-methylpropyl)-1H-imidazo[4,5-c]quinoline-2,4-diamine as a thick, brown oil.

Part F

Trifluoroacetic acid (150 mL) was added to $N^4,N^4$-bis(4-methoxybenzyl)-$N^2$-methyl-1-(2-methylpropyl)-1H-imidazo[4,5-c]quinoline-2,4-diamine (15 g, 29.5 mmol), and the reaction was heated at 70° C. overnight and allowed to cool to ambient temperature. Aqueous sodium hydroxide (170 mL of 12 M) was added to adjust the solution to pH 9. The resulting mixture was extracted with chloroform (3×), and the combined extracts were washed with brine (3×), dried over magnesium sulfate, filtered through a layer of CELITE filter agent, and concentrated under reduced pressure. The residue was purified by automated flash chromagraphy (silica cartridge, eluting with 0-25% methanol in ethyl acetate). The resulting product was further purified twice by flash chromatography on silica gel (eluting first with 5-10% methanol in dichloromethane and then 5-7.5% methanol in dichloromethane) to provide 3 g of $N^2$-methyl-1-(2-methylpropyl)-1H-imidazo[4,5-c]quinoline-2,4-diamine.

MS (ESI) m/z 270.1 (M+H).

Example 6

$N^2$-Ethyl-1-(2-methylpropyl)-1H-imidazo[4,5-c]quinoline-2,4-diamine

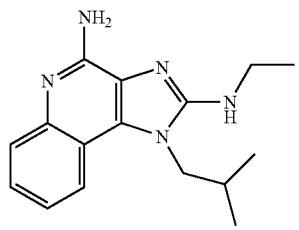

Part A

A portion of the crude material from Part C of Example 5 (30 g), 5% platinum on carbon (3 g), and acetonitrile (200 mL) were added to a Parr vessel and shaken under hydrogen pressure (45 psi, $3.1 \times 10^5$ Pa) overnight. Magnesium sulfate was added to the reaction mixture, which was filtered through a layer of CELITE filter agent and concentrated under reduced pressure to provide $N^2,N^2$-bis(4-methoxybenzyl)-$N^4$-(2-methylpropyl)quinoline-2,3,4-triamine as a red oil, which was used without purification.

Part B

Triethylamine (16.7 mL, 0.120 mol) and ethyl isothiocyanate (6.3 mL, 72 mmol) were sequentially added to a solution of the material from Part A in pyridine (100 mL), and the reaction was heated for five minutes at 80° C. 1,(3-Dimethylaminopropyl)-3-ethylcarbodiimide hydrochloride (38 g, 245 mmol) was added slowly, and the reaction was heated at 80° C. for three days, allowed to cool to ambient temperature, and concentrated under reduced pressure. The residue was dissolved in dichloromethane (200 mL), and the resulting solution was washed twice with saturated aqueous sodium bicarbonate, dried over magnesium sulfate, filtered through a layer of CELITE filter agent, and concentrated under reduced pressure to provide a brown oil. The crude product was purified by automated flash chromatography (silica cartridge, eluting with 0-10% methanol in dichloromethane) and then purified by flash chromatography on silica gel (eluting with 5% methanol in dichloromethane) to provide 8 g of $N^2$-ethyl-$N^4$,$N^4$-bis(4-methoxybenzyl)-1-(2-methylpropyl)-1H-imidazo[4,5-c]quinoline-2,4-diamine as a thick, brown oil.

Part C

Trifluoroacetic acid (20 mL) was added to $N^2$-ethyl-$N^4$,$N^4$-bis(4-methoxybenzyl)-1-(2-methylpropyl)-1H-imidazo[4,5-c]quinoline-2,4-diamine (2.0 g, 3.8 mmol), and the reaction was heated at 50° C. for four hours and allowed to cool to ambient temperature. Aqueous sodium hydroxide (6 M) was added to adjust the solution to pH 9, and then dichloromethane and saturated aqueous sodium bicarbonate were added. The organic layer was separated and washed twice with aqueous sodium bicarbonate, dried over magnesium sulfate, filtered through a layer of CELITE filter agent, and concentrated under reduced pressure. The residue was purified twice by automated flash chromatography (silica cartridge, eluting with 12% methanol in dichloromethane followed by silica cartridge, eluting with 3-12% methanol in dichloromethane). The resulting product was recrystallized from acetonitrile containing a few drops of methanol, combined with material from another run, and recrystallized again using the same solvents to provide 210 mg of $N^2$-ethyl-1-(2-methylpropyl)-1H-imidazo[4,5-c]quinoline-2,4-diamine as beige needles, mp 188-190° C.

Anal. calcd. for $C_{16}H_{21}N_5$: C, 67.82; H, 7.47; N, 24.71. Found: C, 67.50; H, 8.08; N, 24.38.

Example 7

1-[4-Amino-2-(ethylamino)-1H-imidazo[4,5-c]quinolin-1-yl]-2-methylpropan-2-ol

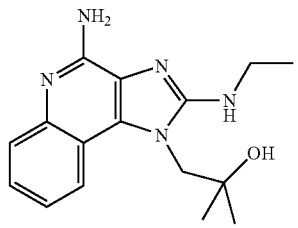

Part A

Triethylamine (3.15 mL, 22.6 mmol) and ethyl isothiocyanate (1.19 mL, 13.6 mmol) were sequentially added to a solution of 1-[(3-amino-2-chloro-4-quinolinyl)amino]-2-methyl-2-propanol (3.00 g, 11.3 mmol) in pyridine (50 mL), and the reaction was heated for five minutes at 80° C. 1,(3-Dimethylaminopropyl)-3-ethylcarbodiimide hydrochloride (2.60 g, 13.6 mmol) was added slowly, and the reaction was heated overnight at 80° C., allowed to cool to ambient temperature, and concentrated under reduced pressure. The residue was dissolved in ethyl acetate (300 mL), and the resulting solution was washed with brine (3×) and water (1×), dried over magnesium sulfate, filtered, and concentrated under reduced pressure. The crude product was purified by column chromatography on silica gel (eluting with 2-3% methanol in dichloromethane) to provide 2.78 g of 1-[4-chloro-2-(ethylamino)-1H-imidazo[4,5-c]quinolin-1-yl]-2-methylpropan-2-ol.

Part B

1-[4-Chloro-2-(ethylamino)-1H-imidazo[4,5-c]quinolin-1-yl]-2-methylpropan-2-ol (2.49 g, 7.81 mmol) and ammonia (70 mL of a 7 N solution in methanol) were added to a high-pressure vessel, which was sealed and heated overnight in an oven at 150° C. An analysis by HPLC indicated the presence of starting material, and additional ammonia in methanol (10 mL) was added. The reaction was heated for four hours at 150° C. and cooled to ambient temperature. The solvent was removed under reduced pressure, and the residue was purified by flash chromatography on silica gel (eluting with 2-2.5% methanol in dichloromethane with 1% ammonium hydroxide added.) A portion of the product was recrystallized from methanol, isolated by filtration, and washed with cold methanol to provide 496 mg of 1-[4-amino-2-(ethylamino)-1H-imidazo[4,5-c]quinolin-1-yl]-2-methylpropan-2-ol as white needles, mp 233-235° C.

Anal. calcd. for $C_{16}H_{21}N_5O \cdot 1.2CH_3OH$: C, 61.37; H, 7.37; N, 20.81. Found: C, 61.05; H, 7.56; N, 20.90.

Example 8

1-{4-Amino-2-[(2-methoxyethyl)amino]-1H-imidazo[4,5-c]quinolin-1-yl}-2-methylpropan-2-ol

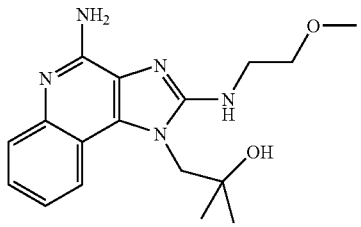

Part A

The method described in Part A of Example 7 was used to treat 1-[(3-amino-2-chloro-4-quinolinyl)amino]-2-methyl-2-propanol (3.00 g, 11.3 mmol) with 2-methoxyethyl isothiocyanate (1.59 g, 13.6 mmol) to provide 2.59 g of 1-{4-chloro-2-[(2-methoxyethyl)amino]-1H-imidazo[4,5-c]quinolin-1-yl}-2-methylpropan-2-ol after chromatographic purification.

Part B

1-{4-Chloro-2-[(2-methoxyethyl)amino]-1H-imidazo[4,5-c]quinolin-1-yl}-2-methylpropan-2-ol (2.1 g, 6.2 mmol) and ammonia (25 mL of a 7 N solution in methanol) were added to a high-pressure vessel, which was sealed and heated overnight in an oven at 150° C. and then allowed to cool to ambient temperature. The solvent was removed under reduced pressure, and the residue was purified by flash chromatography on silica gel (eluting with 2% methanol in dichloromethane with 1% ammonium hydroxide added.) The isolated product was dried under high vacuum overnight to provide 1.08 g of 1-{4-amino-2-[(2-methoxyethyl)amino]-1H-imidazo[4,5-c]quinolin-1-yl}-2-methylpropan-2-ol as a white solid, mp 176-178° C.

Anal. calcd. for $C_{17}H_{23}N_5O_2$: C, 61.99; H, 7.04; N, 21.26. Found: C, 61.63; H, 7.12; N, 21.15.

These data were obtained for a portion of the product obtained after chromatography.

Example 9

1-{4-Amino-2-[(3-methoxypropyl)amino]-1H-imidazo[4,5-c]quinolin-1-yl}-2-methylpropan-2-ol

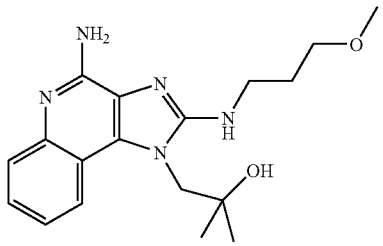

Part A

The method described in Part A of Example 7 was used to treat 1-[(3-amino-2-chloro-4-quinolinyl)amino]-2-methyl-2-propanol (3.00 g, 11.3 mmol) with 3-methoxypropylisothiocyanate (1.78 g, 13.6 mmol) to provide 2.9 g of 1-{4-chloro-2-[(3-methoxypropyl)amino]-1H-imidazo[4,5-c]quinolin-1-yl}-2-methylpropan-2-ol after chromatographic purification.

Part B

The method described in Part B of Example 8 was used to treat 1-{4-chloro-2-[(3-methoxypropyl)amino]-1H-imidazo[4,5-c]quinolin-1-yl}-2-methylpropan-2-ol (2.9 g, 8.0 mmol) with ammonia to provide, after chromatography, 0.83 g of 1-{4-amino-2-[(3-methoxypropyl)amino]-1H-imidazo[4,5-c]quinolin-1-yl}-2-methylpropan-2-ol as a white solid, mp 209-210° C.

Anal. calcd. for $C_{18}H_{25}N_5O_2 \cdot 0.49CH_3OH$: C, 61.90; H, 7.44; N, 19.51. Found: C, 61.60; H, 7.58; N, 19.90.

Examples 10-13

Part A

Methanol (200 mL) and hydrochloric acid (22 mL of 6 N) were added to $N^4$-(tert-butyl)-2-chloroquinoline-3,4-diamine (16.6 g, 66.5 mmol), and the reaction was heated overnight at 75° C. and concentrated under reduced pressure at 100° C. The solid residue was further dried under high vacuum for three hours and then mixed with diethyl ether. The solid was isolated by filtration, washed with diethyl ether, and dried under reduced pressure to provide 16.17 g of 2-chloroquinoline-3,4-diamine hydrochloride.

Part B

Triethylamine (2.0 equivalents) and the isothiocyanate shown in the table below (1.2 equivalents) were sequentially added to a 0.14-0.23 M solution of 2-chloroquinoline-3,4-diamine hydrochloride (1.0 equivalent) in pyridine, and the reaction was heated for five minutes at 80° C. 1,(3-Dimethylaminopropyl)-3-ethylcarbodiimide hydrochloride (1.2 equivalents) was added, and the reaction was heated overnight at 80° C., allowed to cool to ambient temperature, and concentrated under reduced pressure at 100° C. The residue was dissolved in chloroform (500 mL), and the resulting solution was washed with brine (3×300 mL) and water (1×300 mL), dried over magnesium sulfate, filtered, and concentrated under reduced pressure. The crude product was purified by automated flash chromatography (silica cartridge, eluting with 0-8% methanol in dichloromethane with 5% aqueous ammonium hydroxide added).

Part C

The material from Part B (230 mg -1.76 g) and ammonia (45 mL of a 7 N solution in methanol) were added to a high-pressure vessel, which was sealed and heated in an oven at 170° C. for two days (Examples 10 and 11) or for four days (Examples 12 and 13). The resulting solution was concentrated under reduced pressure, and the residue was purified by automated flash chromatography (silica cartridge, eluting with 0-10% methanol in dichloromethane with 5% ammonium hydroxide added) to provide the product with the structure shown in the table below. High resolution mass spectrometry data (ESI) for each example is also provided in the table below.

Examples 10-13

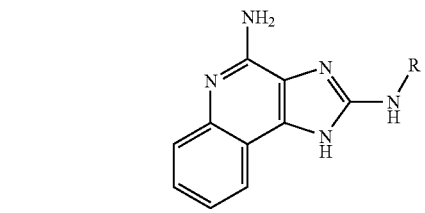

| Example | Isothiocyanate in Part B | R | Calculated Mass $(M + H)^+$ | Measured Mass $(M + H)^+$ |
|---|---|---|---|---|
| 10 | Ethyl isothiocyanate | $-CH_2CH_3$ | 228.1249 | 228.1252 |

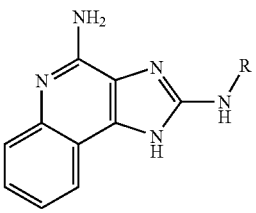

| Example | Isothiocyanate in Part B | R | Calculated Mass (M + H)+ | Measured Mass (M + H)+ |
|---|---|---|---|---|
| 11 | Methyl isothiocyanate | —CH₃ | 214.1093 | 214.1089 |
| 12 | 2-Methoxyethyl isothiocyanante | —CH₂CH₂OCH₃ | 258.1355 | 258.1353 |
| 13 | 2-Methoxypropyl isothiocyanate | —CH₂CH₂CH₂OCH₃ | 272.1511 | 272.1513 |

Example 14

$N^2$,1-Dimethyl-1H-imidazo[4,5-c]quinoline-2,4-diamine

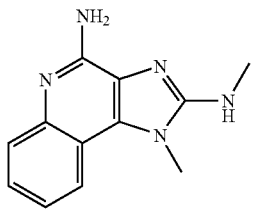

Part A

The method described in Part A of Example 4 was used to treat 2,4-dichloro-3-nitroquinoline (10.0 g, 40.8 mmol) with triethylamine (8.53 mL, 61.2 mmol) and methylamine (20.41 mL of a 2 M solution in tetrahydrofuran, 40.82 mmol) to provide 9.45 g of N-methyl-2-chloro-3-nitroquinolin-4-amine as a yellow powder.

Part B

The method described in Part B of Example 4 was used to hydrogenate (50 psi, 3.4×10⁵ Pa) N-methyl-2-chloro-3-nitroquinolin-4-amine (9.45 g, 39.4 mmol) to provide 8.4 g of $N^4$-methyl-2-chloroquinoline-3,4-diamine, which was used without purification.

Part C

Triethylamine (5.64 mL, 40.5 mmol) and methyl isothiocyanate (1.66 mL, 24.3 mmol) were sequentially added to a solution of $N^4$-methyl-2-chloroquinoline-3,4-diamine (4.2 g, 20 mmol) in pyridine (100 mL), and the reaction was stirred for five minutes at ambient temperature. 1,(3-Dimethylaminopropyl)-3-ethylcarbodiimide (3.77 g, 24.3 mmol) was added, and the reaction was stirred overnight at ambient temperature. An analysis by LC/MS indicated the presence of starting material; therefore, the reaction was heated overnight at 80° C. An analysis by LC/MS again indicated the presence of starting material; 1,(3-dimethylaminopropyl)-3-ethylcarbodiimide hydrochloride (4.56 g, 24.3 mmol) was added. The reaction was stirred overnight at 80° C., allowed to cool to ambient temperature, and diluted with water (500 mL). The mixture was extracted with ethyl acetate, and the extract was washed with water, dried over magnesium sulfate, filtered, and concentrated under reduced pressure. Dichloromethane (20 mL), methanol (2 mL), and diethyl ether (100 mL) were added to the resulting solid. A white solid was present and was isolated by filtration to provide 600 mg of an uncyclized thiourea intermediate. The filtrate was concentrated under reduced pressure and purified by automated flash chromatography on silica gel to provide 287 mg of 4-chloro-N,1-dimethyl-1H-imidazo[4,5-c]quinolin-2-amine.

Part D

4-Chloro-N,1-dimethyl-1H-imidazo[4,5-c]quinolin-2-amine (0.280 g, 0.88 mmol) and ammonia (15 mL of a 7 N solution in methanol) were added to a high-pressure vessel, which was sealed and heated in an oven at 145° C. for two days. An analysis by LC/MS indicated the presence of starting material, and heating at 145° C. was continued for a total of two weeks. The solvent was removed under reduced pressure, and the residue was purified by automated flash chromagraphy (silica cartridge, eluting with 1-20% methanol in dichloromethane with 1% aqueous ammonium hydroxide added) to provide 153 mg of $N^2$,1-dimethyl-1H-imidazo[4,5-c]quinoline-2,4-diamine.

MS (ESI) m/z 228.1227 (M+H)⁺.

Example 15

$N^2$-Ethyl-1-methyl-1H-imidazo[4,5-c]quinoline-2,4-diamine

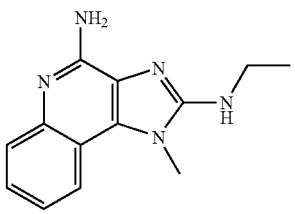

Part A

The method described in Part C of Example 14 was used to treat $N^4$-methyl-2-chloroquinoline-3,4-diamine (4.2 g, 20 mmol) with ethyl isothiocyanate (2.1 g, 24.3 mmol) to provide 201 mg of 4-chloro-N-ethyl-1-methyl-1H-imidazo[4,5-c]quinolin-2-amine after chromatographic purification.

Part B

4-Chloro-N-ethyl-1-methyl-1H-imidazo[4,5-c]quinolin-2-amine (0.200 g, 0.77 mmol) and ammonia (10 mL of a 7 N solution in methanol) were added to a high-pressure vessel, which was sealed and heated in an oven at 145° C. for 18 hours. An analysis by LC/MS indicated the presence of starting material. Additional ammonia in methanol was added, and heating at 145° C. was continued for an additional two days. An analysis by LC/MS indicated the presence of starting material, and heating at 145° C. was continued for an additional week. The solvent was removed under reduced pressure, and the residue was purified by prep HPLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Following chromatographic purification N²-ethyl-1-methyl-1H-imidazo[4,5-c]quinoline-2,4-diamine was isolated.

MS (ESI) m/z 242.1411 (M+H).

Example 16

N²-Ethyl-6,7-dimethyl-1-(2-methylpropyl)-1H-imidazo[4,5-c]pyridine-2,4-diamine

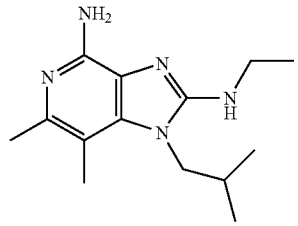

Part A

A modification of the method described in Part A of Example 4 was used to treat 2,4-dichloro-5,6-dimethyl-3-nitropyridine (Dellaria et al, U.S. Pat. No. 6,545,016, Example 7, Part A, 50.0 g, 0.194 mol) with triethylamine (47 mL, 0.34 mol) and isobutylamine (27 mL, 0.27 mol) in anhydrous DMF (500 mL). The work-up procedure was as follows. The reaction mixture was poured into hot water (1 L). The resulting mixture was extracted with chloroform (2×800 mL), and the combined extracts were dried over magnesium sulfate, filtered through a layer of CELITE filter agent, and concentrated under reduced pressure to provide 60.78 g of 2-chloro-5,6-dimethyl-4-(2-methylpropyl)-3-nitropyridine as a bright orange solid.

Part B

Sodium hydride (19.8 g of a 60% dispersion in mineral oil, 0.495 mol) in tetrahydrofuran (THF) (450 mL) was cooled to 0° C.; a solution of phenol (77.7 g, 0.826 mol) in THF (150 mL) was added slowly over a period of 30 minutes. The reaction was stirred at ambient temperature for 30 minutes, and a solution of 2-chloro-5,6-dimethyl-4-(2-methylpropyl)-3-nitropyridine (60.78 g, 0.236 mol) in THF (350 mL) was added. The reaction was heated to 70° C., heated at 50° C. overnight, allowed to cool to ambient temperature, and concentrated under reduced pressure. The residue was dissolved in ethyl acetate (800 mL). The resulting solution was washed sequentially with 1 N aqueous sodium hydroxide (1×800 mL), brine (3×400 mL), 1 N aqueous sodium hydroxide (1×400 mL), brine (1×400 mL), 1 N aqueous sodium hydroxide (1×400 mL), and deionized water (1×400 mL); dried over magnesium sulfate; filtered through a layer of CELITE filter agent; concentrated under reduced pressure; and further dried overnight under high vacuum to provide 80.46 g of 5,6-dimethyl-N-(2-methylpropyl)-3-nitro-2-phenoxypyridin-4-amine as an orange-red solid containing some mineral oil.

Part C

A portion of the material from Part B (25 g) was dissolved in acetonitrile (110 mL), and the resulting solution was washed with hexanes (3×80 mL) and then concentrated under reduced pressure. The residue was dissolved in acetonitrile (270 mL) and added to a Parr vessel with 5% platinum on carbon (14 g). The mixture was placed under hydrogen pressure (30 psi, 2.1×10⁵ Pa) overnight and then filtered twice through CELITE filter agent. The filtrate was concentrated to a volume of 100 mL, passed through a syringe filter, and then concentrated under reduced pressure to provide 14.28 g of 5,6-dimethyl-N⁴-(2-methylpropyl)-2-phenoxypyridine-3,4-diamine as a light brown oil.

Part D

Triethylamine (2.44 mL, 17.5 mmol) and ethyl isothiocyanate (0.92 g, 10.5 mmol) were sequentially added to a solution of 5,6-dimethyl-N⁴-(2-methylpropyl)-2-phenoxypyridine-3,4-diamine (2.5 g, 8.8 mmol) in pyridine (25 mL), and the reaction was heated for five minutes at 80° C. 1,(3-Dimethylaminopropyl)-3-ethylcarbodiimide hydrochloride (1.63 g, 10.5 mmol) was added, and the reaction was heated at 100° C. for two hours, allowed to cool to ambient temperature, and diluted with ethyl acetate. The resulting solution was washed sequentially with brine (2×) and saturated aqueous sodium bicarbonate (1×), dried over magnesium sulfate, filtered, and concentrated under reduced pressure to provide an oil. The crude product was purified by column chromatography on silica gel (eluting with 1-3% methanol in dichloromethane) to provide 1.73 g of N-ethyl-6,7-dimethyl-1-(2-methylpropyl)-4-phenoxy-1H-imidazo[4,5-c]pyridin-2-amine as an oil which solidified to white crystals upon standing overnight at ambient temperature.

Part E

N-Ethyl-6,7-dimethyl-1-(2-methylpropyl)-4-phenoxy-1H-imidazo[4,5-c]pyridin-2-amine (1.3 g, 3.8 mmol) and ammonia (25 mL of a 7 N solution in methanol) were added to a high-pressure vessel, which was sealed and heated in an oven at 170° C. for four days. The resulting solution was allowed to cool to ambient temperature and concentrated under reduced pressure, and the residue was purified by column chromatography on silica gel (eluting with 2-4% methanol in dichloromethane with 1% aqueous ammonium hydroxide added) to provide 294 mg of N²-ethyl-6,7-dimethyl-1-(2-methylpropyl)-1H-imidazo[4,5-c]pyridine-2,4-diamine as a yellow powder, mp 168-170° C.

Anal. calcd. for $C_{14}H_{23}N_5 \cdot 0.2C_2H_5OH$: C, 63.74; H, 8.89; N, 26.17. Found: C, 63.97; H, 9.28; N, 26.02.

An attempt to recrystallize the product from acetonitrile/ethanol was unsuccessful.

Example 17

6,7-Dimethyl-1-(2-methylpropyl)-1H-imidazo[4,5-c]pyridine-2,4-diamine

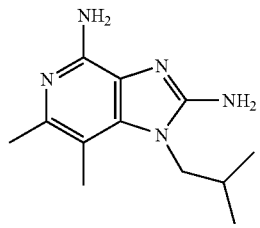

Part A

Cyanogen bromide (1.11 g, 10.5 mmol) was added to a solution of 5,6-dimethyl-N⁴-(2-methylpropyl)-2-phenoxypyridine-3,4-diamine (2.5 g, 8.8 mmol) in ethanol (50 mL), and the solution was heated overnight at 90° C. An analysis by LC/MS indicated the presence of starting material, and additional cyanogen bromide (100 mg) was added. The reaction was heated for one additional hour and allowed to cool to ambient temperature. Ethyl acetate and saturated aqueous sodium bicarbonate were added. The organic layer was separated, washed with brine, dried over magnesium sulfate, filtered, and concentrated under reduced pressure. The residue was purified by column chromatography on silica gel (eluting with 2-5% methanol in dichloromethane) to provide 1.46 g of 6,7-dimethyl-1-(2-methylpropyl)-4-phenoxy-1H-imidazo[4,5-c]pyridin-2-amine hydrobromide as a white powder.

Part B

The method described in Part E of Example 16 was used to aminate 6,7-dimethyl-1-(2-methylpropyl)-4-phenoxy-1H-imidazo[4,5-c]pyridin-2-amine hydrobromide (1.0 g). The chromatographic purification was carried out twice to provide 90 mg of 6,7-dimethyl-1-(2-methylpropyl)-1H-imidazo[4,5-c]pyridine-2,4-diamine as a white powder.

MS (ESI) m/z 235.1 (M+H)$^+$.

Example 18

1-(2,4-Diamino-6,7,8,9-tetrahydro-1H-imidazo[4,5-c]quinolin-1-yl)-2-methylpropan-2-ol

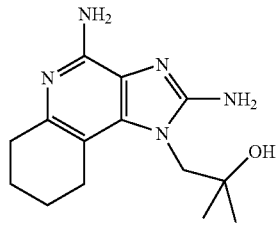

1-(2,4-Diamino-1H-imidazo[4,5-c]quinolin-1-yl)-2-methylpropan-2-ol (0.50 g, 1.8 mmol), trifluoroacetic acid (200 mL), and platinum (IV) oxide (300 mg) were added to a Parr vessel and shaken under hydrogen pressure (45 psi, $3.1\times10^5$ Pa) for eight days. The volatiles were removed under reduced pressure, and the residue was dissolved in methanol and filtered through a layer of CELITE filter agent. The filtrate was concentrated under reduced pressure, and the resulting solid was dissolved in methanol. Hydrogen chloride (30 mL of a 4 M solution in dioxane) was added, and the resulting solution was stirred for two hours. Ammonia (7 M in methanol) was added, and the volatiles were then removed under reduced pressure. Ammonia (7 M in methanol was added a second time, and the resulting mixture was concentrated under reduced pressure. The residue was purified by automated flash chromatography (silica cartridge, eluting with 0-8% methanol in dichloromethane with aqueous ammonium hydroxide added). The resulting white solid was washed with hot acetonitrile and dried in a vacuum oven to provide 280 mg of 1-(2,4-diamino-6,7,8,9-tetrahydro-1H-imidazo[4,5-c]quinolin-1-yl)-2-methylpropan-2-ol as a white solid, mp >270° C.

Anal. calcd. for $C_{14}H_{21}N_5O$: C, 61.07; H, 7.69; N, 25.43. Found: C, 60.81; H, 8.00; N, 25.60.

Examples 19-42

Part A

A solution of 3-nitro-2,4-quinolinediol (100.0 g, 485 mmol) in dichloromethane (400 mL) was cooled to 0° C., and triethylamine (202 mL, 1.46 mol) was added slowly. The resulting brown solution was stirred for several minutes, and trifluoromethanesulfonic anhydride (274 g, 0.970 mol) was added. The reaction was then heated at reflux for three hours and allowed to cool to ambient temperature. Half of the solution was separated and cooled to 0° C. tert-Butyl (3-aminopropyl)carbamate (58 g, 335 mmol) was added in portions, and the resulting solution was stirred at ambient temperature overnight, passed through a plug of silica gel (eluting with dichloromethane), and concentrated under reduced pressure to provide 302.5 g of 4-({3-[(tert-butoxycarbonyl)amino]propyl}amino)-3-nitroquinolin-2-yl trifluoromethanesulfonate as a thick red oil.

Part B

Triethylamine (56.8 mL, 408 mmol) and N,N-bis(4-methoxybenzyl)amine (93.5 g, 0.340 mol) were sequentially added to a solution of 4-({3-[(tert-butoxycarbonyl)amino]propyl} amino)-3-nitroquinolin-2-yl trifluoromethanesulfonate (168 g, 0.340 mol) in toluene (200 mL) at ambient temperature. The solution was stirred at ambient temperature for a few minutes, heated at 65° C. overnight, allowed to cool to ambient temperature, and concentrated under reduced pressure. The residue was dissolved in ethyl acetate (>200 mL), and the resulting solution was washed three times with water, dried over magnesium sulfate, filtered through a layer of CELITE filter agent, concentrated under reduced pressure, and further dried under high vacuum to provide tert-butyl 3-({2-[bis(4-methoxybenzyl)amino]-3-nitroquinolin-4-yl}amino)propylcarbamate as a red oil, which was used without purification.

Part C

The material from Part B, 5% platinum on carbon (17 g), and ethyl acetate (350 mL) were added to a Parr vessel and shaken under hydrogen pressure (45 psi, $3.1\times10^5$ Pa) overnight. Magnesium sulfate was added to the reaction mixture, which was filtered through a layer of CELITE filter agent and concentrated under reduced pressure to provide tert-butyl 3-({3-amino-2-[bis(4-methoxybenzyl)amino]quinolin-4-yl}amino)propylcarbamate as a viscous, red oil, which was used without purification.

Part D

Cyanogen bromide (53.9 g, 509 mmol) was added to a solution of the material from Part C and triethylamine (84.0 mL, 598 mmol) in ethanol (200 mL), and the reaction was heated at 65° C. overnight. Additional cyanogen bromide (0.75 equivalent) was added, and the reaction was heated at reflux for three hours, allowed to cool to ambient temperature, and concentrated under reduced pressure. The residue was dissolved in chloroform (250 mL), and the resulting solution was washed twice with brine, dried over magnesium sulfate, filtered through a layer of CELITE filter agent, concentrated under reduced pressure, and further dried under high vacuum. The crude product was purified by column chromatography on silica gel (eluting with methanol in dichloromethane) to provide tert-butyl 3-{2-amino-4-[bis(4-methoxybenzyl)amino]-1H-imidazo[4,5-c]quinolin-1-yl}propylcarbamate hydrobromide as a red semi-solid.

Part E

Trifluoroacetic acid (28.15 mL, 365.5 mmol) was added to tert-butyl 3-{2-amino-4-[bis(4-methoxybenzyl)amino]-1H-imidazo[4,5-c]quinolin-1-yl}propylcarbamate hydrobromide (8.3 g), and the reaction was heated at 50° C. for four hours, allowed to cool to ambient temperature, and stirred at ambient temperature for three days. The volatiles were removed under reduced pressure. The residue was purified by automated flash chromagraphy (silica cartridge, eluting with aqueous ammonium hydroxide:methanol:dichloromethane in a gradient from 0.3:4.8:95 to 2.5:47.5:50) to provide 630 mg of 1-(3-aminopropyl)-1H-imidazo[4,5-c]quinoline-2,4-diamine.

Part F

N,N-Diisopropylethylamine (37.7 μL, 0.216 mmol) was added to a solution of 1-(3-aminopropyl)-1H-imidazo[4,5-c]quinoline-2,4-diamine (25.2 mg, 0.098 mmol) in pyridine (1 mL) in a test tube. An acid chloride, sulfonyl chloride, isocyanate, or carbamoyl chloride indicated in the table below (0.11 mmol, 1.1 equivalents) was added to the test tube, which was then capped and shaken overnight at ambient temperature. Two drops of water were added to the test tube, and the solvent was removed by vacuum centrifugation. The compounds were purified by prep HPLC using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the reagent used for each example, the structure of the resulting compound, and the observed accurate mass for the isolated trifluoroacetate salt.

Examples 19-42

| Example | Reagent | R | Measured Mass (M + H) |
|---|---|---|---|
| 19 | NO ADDITION-SM ONLY | H | 257.1491 |
| 20 | Acetyl chloride | C(=O)CH₃ | 299.1620 |
| 21 | Methyl chloroformate | C(=O)OCH₃ | 315.1560 |
| 22 | Cyclopropanecarbonyl chloride | C(=O)-cyclopropyl | 325.1745 |
| 23 | Benzoyl chloride | C(=O)Ph | 361.1762 |
| 24 | 3-Cyanobenzoyl chloride | C(=O)-(3-CN-C₆H₄) | 386.1702 |
| 25 | Hydrocinnamoyl chloride | C(=O)CH₂CH₂Ph | 389.2081 |

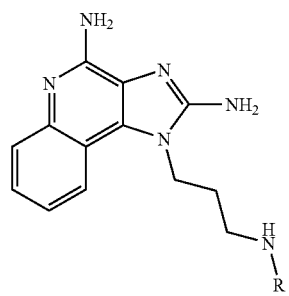

| Example | Reagent | R | Measured Mass (M + H) |
|---|---|---|---|
| 26 | 3-Chlorobenzoyl chloride | 3-chlorobenzoyl | 395.1358 |
| 27 | Nicotinoyl chloride hydrochloride | nicotinoyl (pyridin-3-ylcarbonyl) | 362.1707 |
| 28 | Methanesulfonyl chloride | methanesulfonyl | 335.1280 |
| 29 | Isopropylsulfonyl chloride | isopropylsulfonyl | 363.1624 |
| 30 | Dimethylsulfamoyl chloride | dimethylsulfamoyl | 364.1570 |
| 31 | Benzenesulfonyl chloride | benzenesulfonyl | 397.1416 |
| 32 | 3-Fluorobenzenesulfonyl chloride | 3-fluorobenzenesulfonyl | 415.1329 |
| 33 | beta-Styrene sulfonyl chloride | (E)-2-phenylethenesulfonyl | 423.1591 |
| 34 | 3-Methoxybenzenesulfonyl chloride | 3-methoxybenzenesulfonyl | 427.1533 |

-continued
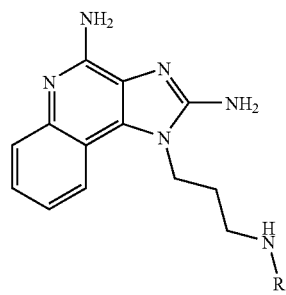
| Example | Reagent | R | Measured Mass (M + H) |
|---|---|---|---|
| 35 | Methyl isothiocyanate | -C(=S)-NH-CH₃ | 330.1493 |
| 36 | Isopropyl isocyanate | -C(=S)-NH-CH(CH₃)₂ | 342.2016 |
| 37 | Cyclopropyl isothiocyanate | -C(=S)-NH-cyclopropyl | 356.1651 |
| 38 | Phenyl isocyanate | -C(=O)-NH-phenyl | 376.1870 |
| 39 | 3-Pyridyl isothiocyanate | -C(=O)-NH-(3-pyridyl) | 393.1572 |
| 40 | 3-Chlorophenyl isocyanate | -C(=O)-NH-(3-chlorophenyl) | 410.1477 |
| 41 | N,N-Dimethylcarbamoyl chloride | -C(=O)-N(CH₃)₂ | 328.1886 |

-continued

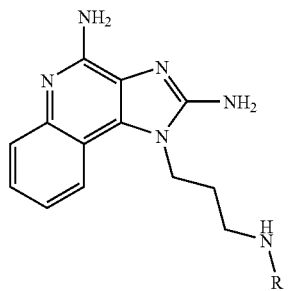

| Example | Reagent | R | Measured Mass (M + H) |
|---|---|---|---|
| 42 | N-Methyl-N-Phenylcarbamoyl chloride | ![structure with acetyl-N(CH3)-phenyl] | 390.2037 |

Example 43

1-(2-Fluoro-2-methylpropyl)-1H-imidazo[4,5-c]quinoline-2,4-diamine

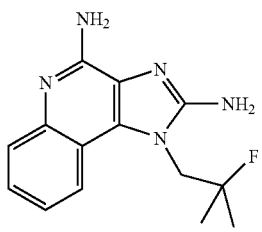

Part A

A solution of tert-butyl 2-hydroxy-2-methylpropylcarbamate (19.2 g, 101 mmol) in dichloromethane (500 mL) was stirred at −78° C. under a nitrogen atmosphere, and (diethylamino)sulfur trifluoride (DAST) (18.0 g, 112 mmol) was added dropwise. The solution was allowed to warm to room temperature and stirred overnight. Saturated aqueous sodium bicarbonate (150 mL) was added. The organic layer was then separated and washed sequentially with saturated aqueous sodium bicarbonate (150 mL), water (150 mL), and brine (150 mL); dried over magnesium sulfate; filtered; and concentrated under reduced pressure. The resulting oil was purified by automated flash chromatography (FLASH 65I cartridge, eluting with 10% ethyl acetate in hexane) to provide 13.7 g of tert-butyl 2-fluoro-2-methylpropylcarbamate as a light yellow oil that crystallized overnight.

Part B

Hydrogen chloride (50 mL of a 4 M solution in 1,4-dioxane) was added to a solution of tert-butyl 2-fluoro-2-methylpropylcarbamate (13.7 g, 71.6 mmol) in dichloromethane (300 mL), and the reaction was stirred for five hours at room temperature and concentrated under reduced pressure. The residue was three times dissolved in toluene and concentrated under reduced pressure to provide 8.08 g of 2-fluoro-2-methylpropan-1-amine hydrochloride as a white solid.

Part C

Triethylamine (2.76 g, 27.3 mmol) was added to a mixture of 2,4-dichloro-3-nitroquinoline (André et al, U.S. Pat. No. 4,988,815, Example 2, 4.44 g, 18.2 mmol) and DMF (50 mL), and then 2-fluoro-2-methylpropan-1-amine hydrochloride (2.5 g, 20 mmol) was added. The reaction was stirred at room temperature overnight and then poured into water (500 mL). The resulting mixture was stirred for 15 minutes. A solid was present and was isolated by filtration to provide 4.8 g of 2-chloro-N-(2-fluoro-2-methylpropyl)-3-nitroquinolin-4-amine as a yellow solid.

Part D

A Parr vessel was charged sequentially with 2-chloro-N-(2-fluoro-2-methylpropyl)-3-nitroquinolin-4-amine (4.75 g, 15.8 mmol), acetonitrile (50 mL), and 5% platinum on carbon (475 mg) and placed under hydrogen pressure (40 psi, 2.8× $10^5$ Pa) overnight. The reaction mixture was filtered through a layer of CELITE filter aid. The filter cake was washed with methanol. The filtrate was concentrated under reduced pressure to provide 4.45 g of 2-chloro-$N^4$-(2-fluoro-2-methylpropyl)quinoline-3,4-diamine as a solid.

Part E

Cyanogen bromide (2.1 g, 19.8 mmol) was added to a solution of the material from Part D in ethanol (100 mL), and the reaction was heated at 100° C. overnight. The heat was increased, and heating was continued for two hours. An analysis by LC/MS indicated the presence of starting material, and additional cyanogen bromide (1.05 g, 9.91 mmol) was added. The reaction was heated at reflux for an additional two hours, and the reaction was still incomplete. Additional cyanogen bromide (2.1 g, 19.8 mmol) was added, and the reaction was heated at reflux overnight, allowed to cool, and filtered. The filter cake was washed with diethyl ether (100 mL) and then dried under vacuum for four hours to provide 2.32 g of 4-chloro-1-(2-fluoro-2-methylpropyl)-1H-imidazo[4,5-c]quinolin-2-amine hydrobromide as a brown solid.

Part F

Crude 4-chloro-1-(2-fluoro-2-methylpropyl)-1H-imidazo[4,5-c]quinolin-2-amine hydrobromide (1.14 g) and ammonia (approximately 100 mL of a 7 N solution in methanol) were added to a pressure vessel, which was sealed and heated at 150° C. for five days. Additional ammonia in methanol was added after three days and again after four days. When the reaction was complete, the volatiles were removed under reduced pressure, and the residue was combined with material from another run. The crude product was purified by automated flash chromatography (silica cartridge, eluting with aqueous ammonium hydroxide:methanol:dichloromethane in a gradient from 0:0:100 to 1:14:85) to provide 270 mg of 1-(2-fluoro-2-methylpropyl)-1H-imidazo[4,5-c]quinoline-2,4-diamine as a light tan solid, mp 251° C.

Anal. calcd. for $C_{14}H_{16}FN_5 \cdot 0.1H_2O$: C, 61.12; H, 5.94; N, 25.46. Found: C, 60.93; H, 6.15; N, 25.40.

Example 44

1-[(1R)-1-Phenylethyl]-1H-imidazo[4,5-c]quinoline-2,4-diamine

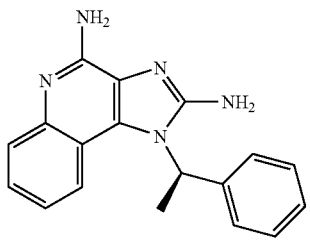

Part A

The method described in Part A of Example 4 was used to treat 2,4-dichloro-3-nitroquinoline (20.6 g, 85.1 mmol) in DMF (100 mL) with triethylamine (35 mL, 0.225 mol) and (R)-(+)-α-methylbenzylamine (13.3 mL, 102 mmol). After the precipitate was isolated by filtration, it was washed with water and diethyl ether to provide 24.35 g of 2-chloro-3-nitro-N-[(1R)-1-phenylethyl]quinolin-4-amine as an orange solid.

Part B

The method of Part B of Example 4 was used to hydrogenate 2-chloro-3-nitro-N-[(1R)-1-phenylethyl]quinolin-4-amine (24.35 g, 73.3 mmol) with the modifications that the reaction was stopped after one hour, and magnesium sulfate was added to the mixture before filtration. 2-Chloro-$N^4$-[(1R)-1-phenylethyl]quinoline-3,4-diamine (21.0 g) was isolated as an amber oil.

Part C

A solution of 2-chloro-$N^4$-[(1R)-1-phenylethyl]quinoline-3,4-diamine (10.0 g, 33.6 mmol) in ethanol (100 mL) was heated to 80° C. Cyanogen bromide (3.84 g, 36.9 mmol) was added, and the dark solution was heated at 80° C. for two hours. An analysis by LC/MS indicated the presence of starting material. Additional cyanogen bromide (3.84 g, 36.9 mmol) was added, and the reaction was stirred overnight at 80° C. The solvent was removed under reduced pressure, and the resulting oil was stirred with diethyl ether (300 L), isolated by filtration, washed with diethyl ether, and dried under vacuum to provide 13.77 g of 4-chloro-1-[(1R)-1-phenylethyl]-1H-imidazo[4,5-c]quinolin-2-amine hydrobromide as a brown solid.

Part D

4-Chloro-1-[(1R)-1-phenylethyl]-1H-imidazo[4,5-c]quinolin-2-amine hydrobromide (4.2 g, 13 mmol) and ammonia (65 mL of a 7 N solution in methanol) were added to a high-pressure vessel, which was sealed and heated in an oven at 135° C. overnight. The reaction mixture was concentrated under reduced pressure, and the residue was purified by automated flash chromatography (silica cartridge, eluting with aqueous ammonium hydroxide:methanol:dichloromethane in a gradient from 0:0:100 to 0.4:7.6:92). The chromatographed product was washed with diethyl ether to provide 362 mg of 1-[(1R)-1-phenylethyl]-1H-imidazo[4,5-c]quinoline-2,4-diamine as brown needles, mp 156-160° C.

Anal. calcd. for $C_{18}H_{17}N_5 \cdot 0.3H_2O$: C, 70.02; H, 5.75; N, 22.68. Found: C, 69.59; H, 5.56; N, 22.37.

Example 45

1-[(1S)-1-Phenylethyl]-1H-imidazo[4,5-c]quinoline-2,4-diamine

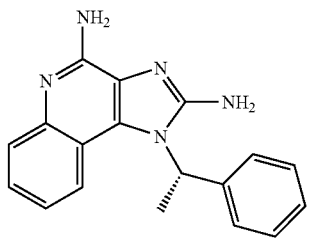

Part A

The method described in Part A of Example 4 was used to treat 2,4-dichloro-3-nitroquinoline (19.4 g, 78.5 mmol) in DMF (100 mL) with triethylamine (32 mL, 0.235 mol) and (S)-(−)-α-methylbenzylamine (11.5 g, 94.2 mmol) with the modification that the reaction was allowed to warm to room temperature and stirred for two hours. After the isolated precipitate was washed with water, it was dried under high vacuum overnight to provide 25.1 g of 2-chloro-3-nitro-N-[(1S)-1-phenylethyl]quinolin-4-amine as an orange solid.

Part B

The method of Part B of Example 44 was used to hydrogenate 2-chloro-3-nitro-N-[(1S)-1-phenylethyl]quinolin-4-amine (24.35 g, 73.3 mmol) to provide 2-chloro-$N^4$-[(1S)-1-phenylethyl]quinoline-3,4-diamine as an amber oil.

Part C

A solution of 2-chloro-$N^4$-[(1S)-1-phenylethyl]quinoline-3,4-diamine (13.0 g, 43.7 mmol) in ethanol (100 mL) was heated to 80° C. for 30 minutes. Cyanogen bromide (4.6 g, 44 mmol) was added, and the dark solution was heated at 80° C. for one hour. An analysis by LC/MS indicated the presence of starting material. Additional cyanogen bromide (4.6 g, 44 mmol) was added, and the reaction was stirred overnight at 80° C. The reaction was still incomplete, and additional cyanogen bromide (4.6 g, 44 mmol) was added. The reaction was heated overnight at 100° C. after a fourth equivalent of cyanogen bromide (4.6 g, 44 mmol) was added. The solvent was removed under reduced pressure, and aqueous sodium hydroxide (200 mL of 2 N) was slowly added to the resulting oil. The mixture was stirred for two hours at room temperature, and a precipitate formed, which was isolated by filtration. The solid was then purified by automated flash chromatography (silica cartridge, eluting with aqueous ammonium hydroxide:methanol:dichloromethane in a gradient from 0:0:100 to 0.3:4.7:95) to provide 9.4 g of 4-chloro-1-[(1S)-1-phenylethyl]-1H-imidazo[4,5-c]quinolin-2-amine hydrobromide as a brown solid. A portion of the product was purified again by automated flash chromatography (silica cartridge, eluting with aqueous ammonium hydroxide:methanol:

dichloromethane in a gradient from 0:0:100 to 0.2:3.8:96) to provide a sample of the product as gray needles, mp 170-172° C.

Anal. calcd. for $C_{18}H_{15}ClN_5 \cdot 0.3HBr$: C, 62.29; H, 4.44; N, 16.14. Found: C, 62.20; H, 4.38; N, 16.15.

Part D

4-Chloro-1-[(1S)-1-phenylethyl]-1H-imidazo[4,5-c]quinolin-2-amine hydrobromide (4.0 g, 12 mmol) was treated with ammonia (65 mL of a 7 N solution in methanol) according to the method in Part D of Example 44. The crude product was purified twice by automated flash chromatography (silica cartridge, eluting with aqueous ammonium hydroxide:methanol:dichloromethane in a gradient from 0:0:100 to 0.2:3.8:96). The chromatographed product was washed with diethyl ether several times and dried in a vacuum oven to provide 285 mg of 1-[(1S)-1-phenylethyl]-1H-imidazo[4,5-c]quinoline-2,4-diamine as a brown solid, mp 135-140° C.

Anal. calcd. for $C_{18}H_{17}N_5 \cdot 0.9CH_4O$: C, 68.33; H, 6.25; N, 21.08. Found: C, 68.09; H, 6.14; N, 21.11.

Example 46

1-[(2,4-Diamino-1H-imidazo[4,5-c]quinolin-1-yl)methyl]cyclobutanol

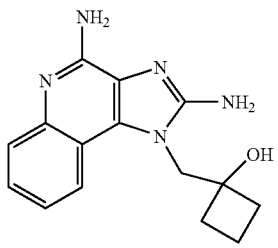

Part A

Potassium cyanide (39 mg, 0.60 mmol) and 18-Crown-6 (159 mg, 0.60 mmol) were combined with methanol (8 mL), and the mixture was stirred for ten minutes and sonicated until all solids dissolved. The methanol was removed under reduced pressure, and the residue was dried under high vacuum for ten minutes and then dissolved in trimethylsilyl cyanide (8.4 mL, 63 mmol). The resulting solution was added dropwise to neat, cold (0° C.) cyclobutanone (4.20 g, 59.9 mmol), and the orange mixture was stirred for five minutes at 0° C. and for two hours at room temperature to provide (1-trimethylsilanyloxy)cyclobutanecarbonitrile.

Part B

A mixture of the material from Part A and THF (240 mL) was cooled to 0° C. Lithium aluminum hydride (2.27 g, 59.9 mmol) was added in two portions over a period of five minutes, and the resulting mixture was stirred for one hour at 0° C. to 5° C. Water (2.5 mL) was added dropwise. The cooling bath was removed, and aqueous sodium hydroxide (2.5 mL of 2 M) was added. The mixture was stirred for ten minutes, and water (7.5 mL) was added. The mixture was stirred for 1.5 hours, and magnesium sulfate was added. The mixture was stirred for ten minutes and then filtered through a layer of CELITE filter agent. The filter cake was washed with THF (200 mL). The filtrate was concentrated under reduced pressure to provide 6.31 g of a 50:50 mixture of 1-(aminomethyl)cyclobutanol and [(1-trimethylsilanyloxy)cyclobutyl]methylamine as a white solid.

Part C

A solution of 2,4-dichloro-3-nitroquinoline (12.4 g, 46.0 mmol) in dichloromethane (150 mL) was cooled to 0° C., and triethylamine (7.8 mL, 55 mmol) was added. A solution of the material from Part B in dichloromethane (30 mL) was added dropwise, and the reaction was allowed to warm to room temperature slowly and stirred overnight. Saturated aqueous sodium bicarbonate (100 mL) was added, and a solid formed in the aqueous layer. The aqueous layer was extracted with dichloromethane (2×50 mL) and then filtered to isolate the solid. The combined organic fractions were dried over magnesium sulfate, filtered, and concentrated under reduced pressure. The residue from the organic fractions was triturated with acetonitrile and isolated by filtration to provide 4.63 g of 1-{[(2-chloro-3-nitroquinolin-4-yl)amino]methyl}cyclobutanol as a yellow solid. The filtrate from the trituration was concentrated under reduced pressure, and the residue was combined with the solid filtered from the aqueous layer, methanol (100 mL), and potassium carbonate (30 g). The mixture was stirred for two hours and concentrated under reduced pressure. The residue was triturated with water (100 mL) for two hours and isolated by filtration to provide 6.22 g of 1-{[(2-chloro-3-nitroquinolin-4-yl)amino]methyl}cyclobutanol as a yellow solid.

Part D

Platinum on carbon (0.40 g of 5%) was added to a solution of 1-{[(2-chloro-3-nitroquinolin-4-yl)amino]methyl}cyclobutanol (4.0 g, 13 mmol) in ethyl acetate (65 mL), and the mixture was placed under hydrogen pressure (40 psi, $2.8 \times 10^5$ Pa) on a Parr apparatus for 3.5 hours. The mixture was filtered through a layer of CELITE filter agent, and the filter cake was washed with ethyl acetate (100 mL). The filtrate was concentrated under reduced pressure to provide 1-{[(3-amino-2-chloroquinolin-4-yl)amino]methyl}cyclobutanol as a yellow solid.

Part E

A solution of the material from Part D in ethanol (30 mL) was heated to reflux. Cyanogen bromide (0.74 g, 7.15 mmol) was added, and the reaction was heated at reflux overnight and allowed to cool to room temperature. A precipitate was present and was isolated by filtration, triturated with saturated aqueous sodium bicarbonate, and isolated by filtration to provide 1.14 g of 1-[(2-amino-4-chloro-1H-imidazo[4,5-c]quinolin-1-yl)methyl]cyclobutanol as a white solid.

Part F

1-[(2-Amino-4-chloro-1H-imidazo[4,5-c]quinolin-1-yl)methyl]cyclobutanol (1.14 g, 3.77 mmol) and ammonia (15 mL of a 7 N solution in methanol) were added to a pressure vessel, which was sealed and heated at 150° C. for five days. Additional ammonia in methanol (50 mL) was added after two days. When the reaction was complete, the volatiles were removed under reduced pressure, and the residue was triturated sequentially with methanol and saturated aqueous sodium bicarbonate and isolated by filtration. The resulting yellow solid was purified by automated flash chromatography on silica gel (40+M cartridge, eluting with 0% to 75% CMA in chloroform) followed by recrystallization from methanol. The crystals were dried overnight in a vacuum oven at 90° C. to provide 0.240 g of 1-[(2,4-diamino-1H-imidazo[4,5-c]quinolin-1-yl)methyl]cyclobutanol as pale yellow crystals, mp 295° C. (decomposition).

MS (ESI) m/z 284 (M+H)$^+$;

Anal. calcd for $C_{15}H_{17}N_5O$: C, 63.59; H, 6.05; N, 24.72. Found: C, 63.48; H, 5.77; N, 24.63.

Examples 47-53

Part A

A solution of tert-butyl 4-[(3-amino-2-chloroquinolin-4-yl)amino]butylcarbamate (Nanba et al, U.S. Pat. No. 6,069,149, Example 14, 9.5 g, 26 mmol) in ethanol (100 mL) was heated to 110° C.; cyanogen bromide (2.98 g, 28.6 mmol) was added. The reaction was stirred for three hours at 110° C., and an analysis by LC/MS indicated the presence of starting material. Additional cyanogen bromide (0.55 equivalent) was added, and the reaction was stirred for three days at 110° C. and allowed to cool to room temperature. Most of the solvent was removed under reduced pressure, and 2 N aqueous sodium hydroxide (500 mL) was added. The mixture was stirred for 30 minutes, and ethyl acetate (400 mL) was added. A precipitate formed and was isolated by filtration to provide 7.188 g of tert-butyl 4-(2-amino-4-chloro-1H-imidazo[4,5-c]quinolin-1-yl)butylcarbamate as a cream-colored solid.

Part B tert-Butyl 4-(2-amino-4-chloro-1H-imidazo[4,5-c]quinolin-1-yl)butylcarbamate (5.5 g, 14 mmol) and ammonia (50 mL of a 7 N solution in methanol) were added to a high-pressure vessel, which was sealed and heated in an oven at 170° C. for two days. The resulting solution was allowed to cool to room temperature and concentrated under reduced pressure. The resulting dark oil was partially dissolved in methanol, and diethyl ether was added. The mixture was stirred for one hour, and a solid was isolated by filtration. The solid was washed sequentially with diethyl ether and 90:10 dichloromethane:methanol (100 mL) and dried on the filter funnel for 30 minutes. The resulting green solid (2.52 g) was purified by automated flash chromatography on silica gel (eluting with aqueous ammonium hydroxide:methanol:dichloromethane in a gradient from 0:0:100 to 2.5:47.5:50) to provide 167 mg of 1-(4-aminobutyl)-1H-imidazo[4,5-c]quinoline-2,4-diamine as a dark green solid.

Part C

N,N-Diisopropylethylamine (29.4 µL, 0.169 mmol) was added to a solution of 1-(4-aminobutyl)-1H-imidazo[4,5-c]quinoline-2,4-diamine (22.8 mg, 0.0845 mmol) in N,N-dimethylacetamide (DMA) (1 mL) in a test tube. An acid chloride, sulfonyl chloride, isocyanate, or carbonyl chloride indicated in the table below (0.0887 mmol, 1.05 equivalents) was added to the test tube, which was then capped and vortexed for four hours at room temperature. Two drops of water were added to the test tube, and the solvent was removed by vacuum centrifugation. The compounds were purified by reversed phase prep HPLC according to the method described in Examples 19-42, Part F. The table below shows the reagent used for each example, the structure of the resulting compound, and the observed accurate mass for the isolated trifluoroacetate salt.

Examples 47-53

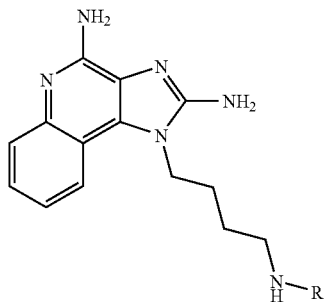

| Example | Reagent | R | Measured Mass (M + H) |
|---|---|---|---|
| 47 | None | H | 271.1670 |
| 48 | Acetyl chloride | —C(O)CH₃ | 313.1785 |
| 49 | Benzoyl chloride | —C(O)Ph | 375.1952 |
| 50 | Methanesulfonyl chloride | —S(O)₂CH₃ | 349.1477 |
| 51 | Benzenesulfonyl chloride | —S(O)₂Ph | 411.1611 |
| 52 | Isopropyl isocyanate | —C(O)NHCH(CH₃)₂ | 356.2211 |
| 53 | 4-Morpholinylcarbonyl chloride | —C(O)-morpholinyl | 384.2126 |

Examples 54-148

The methods of Part F of Examples 19-42 were used to treat 1-(3-aminopropyl)-1H-imidazo[4,5-c]quinoline-2,4-diamine with an acid chloride, sulfonyl chloride, isocyanate, or carbamoyl chloride from the table below and purify the products. The table below shows the reagent used for each example, the structure of the resulting compound, and the observed accurate mass for the isolated trifluoroacetate salt.

Examples 54-148
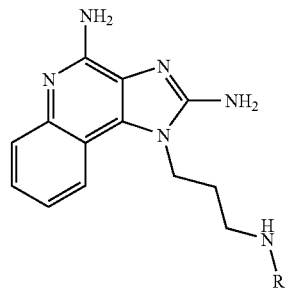
| Example | Reagent | R | Measured Mass (M+H) |
|---|---|---|---|
| 54 | Propionyl chloride | -C(=O)CH₂CH₃ | 313.1756 |
| 55 | Butyryl chloride | -C(=O)CH₂CH₂CH₃ | 327.1947 |
| 56 | Ethyl chloroformate | -C(=O)OCH₂CH₃ | 329.1726 |
| 57 | Methoxyacetyl chloride | -C(=O)CH₂OCH₃ | 329.1736 |
| 58 | Cyclobutanecarbonyl chloride | -C(=O)-cyclobutyl | 339.1927 |
| 59 | 3-Furoyl chloride | -C(=O)-(3-furyl) | 351.1560 |
| 60 | 3-Methylthiopropionyl chloride | -C(=O)CH₂CH₂SCH₃ | 359.1649 |
| 61 | Thiophene-2-cabronyl chloride | -C(=O)-(2-thienyl) | 367.1347 |

-continued
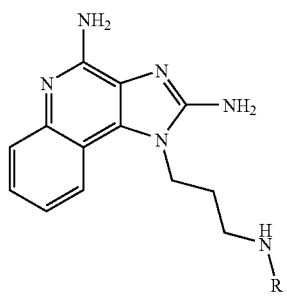
| Example | Reagent | R | Measured Mass (M +H) |
|---|---|---|---|
| 62 | Cyclopentylacetyl chloride | *CH₂C(O)-cyclopentyl* | 367.2255 |
| 63 | Cyclohexanecarbonyl chloride | *C(O)-cyclohexyl* | 367.2244 |
| 64 | m-Toluoyl chloride | *C(O)-(3-methylphenyl)* | 375.1926 |
| 65 | p-Toluoyl chloride | *C(O)-(4-methylphenyl)* | 375.1939 |
| 66 | Phenylacetyl chloride | *C(O)CH₂-phenyl* | 375.1944 |
| 67 | o-Toluoyl chloride | *C(O)-(2-methylphenyl)* | 375.1931 |
| 68 | 2-Thiopheneacetyl chloride | *C(O)CH₂-(2-thienyl)* | 381.1517 |

-continued

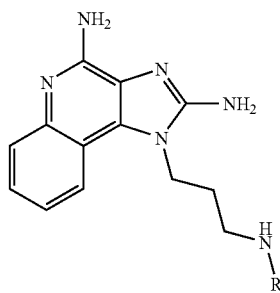

| Example | Reagent | R | Measured Mass (M+H) |
|---|---|---|---|
| 69 | 4-Cyanobenzoyl chloride | 4-cyanobenzoyl | 386.1721 |
| 70 | Cinnamoyl chloride | cinnamoyl | 387.1933 |
| 71 | 3-Methoxybenzoyl chloride | 3-methoxybenzoyl | 391.1894 |
| 72 | 4-Methoxybenzoyl chloride | 4-methoxybenzoyl | 391.1906 |
| 73 | 2-Chlorobenzoyl chloride | 2-chlorobenzoyl | 395.1367 |
| 74 | 3-Chlorobenzoyl chloride | 3-chlorobenzoyl | 395.1377 |
| 75 | Isonicotinoyl chloride hydrochloride | isonicotinoyl | 362.1727 |
| 76 | Picolinoyl chloride hydrochloride | picolinoyl | 362.1729 |

-continued
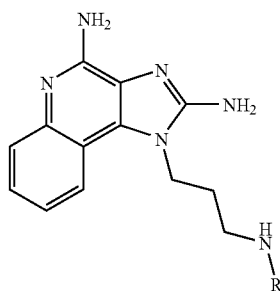
| Example | Reagent | R | Measured Mass (M+H) |
|---|---|---|---|
| 77 | trans-2-Phenyl-1-Cyclopropanecarbonyl chloride | | 401.2079 |
| 78 | 4-Dimethylaminobenzoyl chloride | | 404.2204 |
| 79 | 3-Dimethylaminobenzoyl chloride | | 404.2208 |
| 80 | 4-Chorophenylacetyl chloride | | 409.1578 |
| 81 | 3,4-Dimethoxybenzoyl chloride | | 421.1985 |
| 82 | 3,5-Dimethoxybenzoyl chloride | | 421.1985 |

-continued

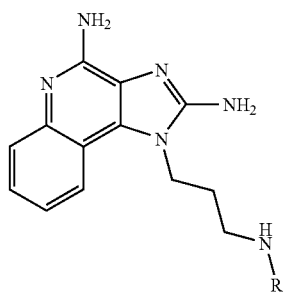

| Example | Reagent | R | Measured Mass (M +H) |
|---|---|---|---|
| 83 | 4-(Trifluoromethyl)benzoyl chloride | 4-(trifluoromethyl)benzoyl | 429.1630 |
| 84 | 3-(Trifluoromethyl)benzoyl chloride | 3-(trifluoromethyl)benzoyl | 429.1652 |
| 85 | 3,4-Dichlorobenzoyl chloride | 3,4-dichlorobenzoyl | 429.0995 |
| 86 | 2,4-Dichlorobenzoyl chloride | 2,4-dichlorobenzoyl | 429.0993 |
| 87 | Ethanesulfonyl chloride | ethanesulfonyl | 349.1478 |
| 88 | 1-Propanesulfonyl chloride | 1-propanesulfonyl | 363.1596 |
| 89 | 1-Butanesulfonyl chloride | 1-butanesulfonyl | 377.1746 |
| 90 | Trifluoromethanesulfonyl chloride | trifluoromethanesulfonyl | 389.0991 |

-continued
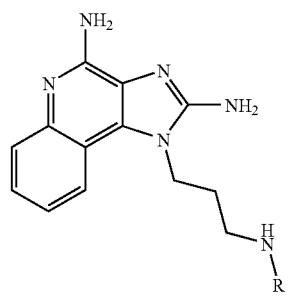
| Example | Reagent | R | Measured Mass (M +H) |
|---|---|---|---|
| 91 | 2-Thiophenesulfonyl chloride | | 403.0991 |
| 92 | 3-Methylbenzenesulfonyl chloride | | 411.1585 |
| 93 | o-Toluenesulfonyl chloride | | 411.1588 |
| 94 | p-Toluenesulfonyl chloride | | 411.1605 |
| 95 | 2-Fluorobenzenesulfonyl chloride | | 415.1378 |
| 96 | 4-Fluorobenzenesulfonyl chloride | | 415.1378 |
| 97 | 2-Cyanobenzenesulfonyl chloride | | 422.1394 |
| 98 | 3-Cyanobenzenesulfonyl chloride | | 422.1377 |

-continued

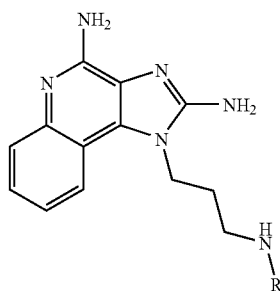

| Example | Reagent | R | Measured Mass (M+H) |
|---|---|---|---|
| 99 | 4-Cyanobenzenesulfonyl chloride | 4-cyanophenylsulfonyl | 422.1362 |
| 100 | 4-Methoxybenzenesulfonyl chloride | 4-methoxyphenylsulfonyl | 427.1529 |
| 101 | 2-Chlorobenzenesulfonyl chloride | 2-chlorophenylsulfonyl | 431.1058 |
| 102 | 3-Chlorobenzenesulfonyl chloride | 4-chlorophenylsulfonyl | 431.1035 |
| 103 | 3-Chloro-4-methylbenzene-1-sulfonyl chloride | 3-chloro-4-methylphenylsulfonyl | 445.1200 |
| 104 | 8-Quinolinesulfonyl chloride | 8-quinolinylsulfonyl | 448.1533 |
| 105 | N-Acetylsulfanilyl chloride | 4-acetamidophenylsulfonyl | 454.1623 |
| 106 | 3,4-Dimethoxybenzenesulfonyl chloride | 3,4-dimethoxyphenylsulfonyl | 457.1637 |

-continued

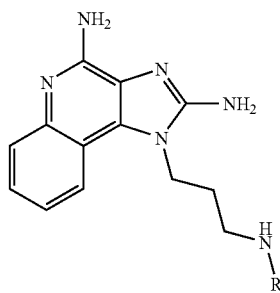

| Example | Reagent | R | Measured Mass (M +H) |
|---|---|---|---|
| 107 | 3-(Trifluoromethyl)benzenesulfonyl chloride | *3-(trifluoromethyl)phenylsulfonyl* | 465.1318 |
| 108 | 4-(Trifluoromethyl)benzenesulfonyl chloride | *4-(trifluoromethyl)phenylsulfonyl* | 465.1293 |
| 109 | 10-Camphorsulfonyl chloride | *camphorsulfonyl* | 471.2157 |
| 110 | 3-(Trifluoromethoxy)benzenesulfonyl chloride | *3-(trifluoromethoxy)phenylsulfonyl* | 481.1241 |
| 111 | 4-(Trifluoromethoxy)benzenesulfonyl chloride | *4-(trifluoromethoxy)phenylsulfonyl* | 481.1243 |
| 112 | Methyl isocyanate | *C(O)NHCH₃* | 314.1761 |
| 113 | Ethyl isocyanate | *C(O)NHCH₂CH₃* | 328.1898 |
| 114 | Cyclopropylmethyl isothiocyanate | *C(S)NHCH₂-cyclopropyl* | 370.1796 |

-continued
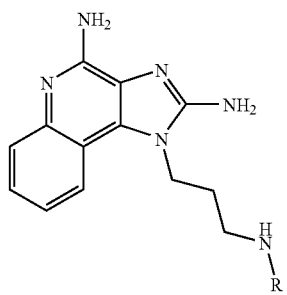
| Example | Reagent | R | Measured Mass (M +H) |
|---|---|---|---|
| 115 | Isobutyl isothiocyanate | | 372.1953 |
| 116 | Cyclohexyl isocyanate | | 382.2318 |
| 117 | Benzyl isocyanate | | 390.2048 |
| 118 | m-Tolyl isocyanate | | 390.2025 |
| 119 | o-Tolyl isocyanate | | 390.2034 |
| 120 | p-Tolyl isocyanate | | 390.2036 |

-continued

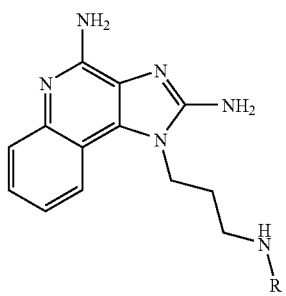

| Example | Reagent | R | Measured Mass (M+H) |
|---|---|---|---|
| 121 | Phenyl isothiocyanate | thiocarbamoyl-phenyl | 392.1642 |
| 122 | Cyclohexyl isothiocyanate | thiocarbamoyl-cyclohexyl | 398.2129 |
| 123 | Ethyl 3-isothiopropionate | carbamoyl-CH2CH2-C(O)O-CH2CH3 | 400.2101 |
| 124 | 2-Tetrahydrofurfuryl isothiocyanate | thiocarbamoyl-CH2-(tetrahydrofuran-2-yl) | 400.1915 |
| 125 | Benzoyl isocyanate | carbamoyl-C(O)-phenyl | 404.1840 |
| 126 | 2,6-Dimethylphenyl isocyanate | carbamoyl-(2,6-dimethylphenyl) | 404.2197 |

-continued
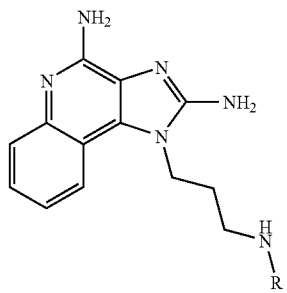
| Example | Reagent | R | Measured Mass (M +H) |
|---|---|---|---|
| 127 | 2-Phenyl ethylisocyanate | ![R group: acetyl-NH-CH2CH2-phenyl] | 404.2187 |
| 128 | 2-Methoxyphenyl isocyanate | ![R group: acetyl-NH-(2-methoxyphenyl)] | 406.1992 |
| 129 | 3-Methoxyphenyl isocyanate | ![R group: acetyl-NH-(3-methoxyphenyl)] | 406.1978 |
| 130 | 4-Methoxyphenyl isocyanate | ![R group: acetyl-NH-(4-methoxyphenyl)] | 406.1992 |
| 131 | 3-Methylphenyl isothiocyanate | ![R group: thioacetyl-NH-(3-methylphenyl)] | 406.1816 |

-continued
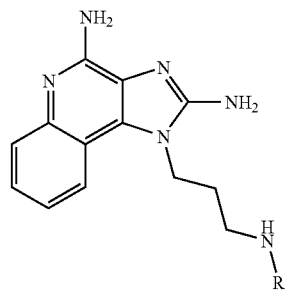
| Example | Reagent | R | Measured Mass (M +H) |
|---|---|---|---|
| 132 | o-Tolyl isothiocyanate | ![structure] | 406.1821 |
| 133 | p-Tolyl isothiocyanate | ![structure] | 406.1795 |
| 134 | 2-(Thien-2-yl)ethyl isocyanate | ![structure] | 410.1758 |
| 135 | 2-Chlorophenyl isocyanate | ![structure] | 410.1488 |
| 136 | 3,4-Difluorophenyl isocyanate | ![structure] | 412.1685 |

-continued
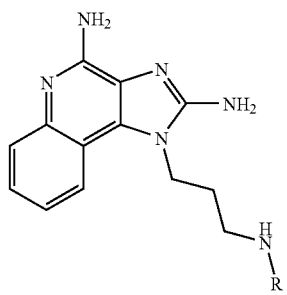
| Example | Reagent | R | Measured Mass (M +H) |
|---|---|---|---|
| 137 | trans-2-Phenylcyclopropyl isocyanate | | 416.2184 |
| 138 | 3-Cyanophenyl isothiocyanate | | 417.1635 |
| 139 | 3-Acetylphenyl isocyanate | | 418.1981 |
| 140 | 4-Acetylphenyl isocyanate | | 418.1993 |
| 141 | 1-Naphthyl isocyanate | | 426.2020 |

-continued
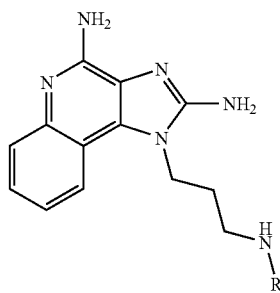
| Example | Reagent | R | Measured Mass (M+H) |
|---|---|---|---|
| 142 | 2-Morpholinoethyl isothiocyanate | 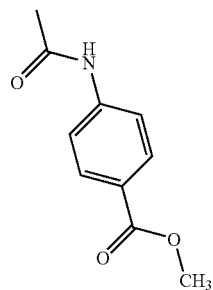 | 429.2202 |
| 143 | Methyl 4-isocyanatobenzoate | 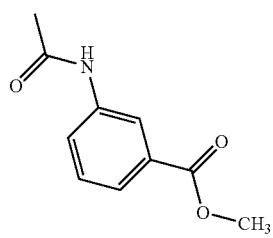 | 434.1916 |
| 144 | 3-Carbomethoxyphenylisocyanate | 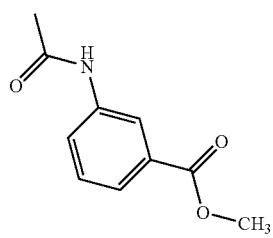 | 434.1927 |
| 145 | 4-(Dimethylamino)phenyl isothiocyanate | 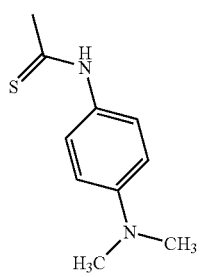 | 435.2053 |
| 146 | 2-Oxo-1-imidazolidinecarbonyl chloride | 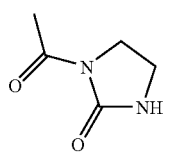 | 369.1774 |

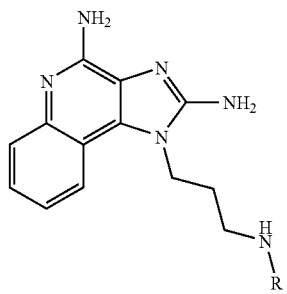

| Example | Reagent | R | Measured Mass (M +H) |
|---|---|---|---|
| 147 | 4-Morpholinylcarbonyl chloride | *morpholinylcarbonyl group* | 370.2015 |
| 148 | 4-Methyl-1-piperazinecarbonyl chloride | *4-methylpiperazinylcarbonyl group* | 383.2286 |

Examples 149-171

Part A

Triethylamine (30.98 g, 306.1 mmol) was added to a solution of 2,4-dichloro-3-nitroquinoline (50.0 g, 204 mmol) in DMF (200 mL). A solution of N-Boc-ethylenediamine (32.7 g, 204 mmol) in DMF (100 mL) was then added in small portions. The reaction was stirred at room temperature, and then most of the DMF was removed under reduced pressure. Water (600 mL) was added to the residue, and the mixture was stirred for three hours. A solid formed and was isolated by filtration, washed with water, and dried under house vacuum to provide 71 g of tert-butyl 2-[(2-chloro-3-nitroquinolin-4-yl)amino]ethylcarbamate as a yellow solid. A portion of the material (15 g) was dissolved in dichloromethane (200 mL), and the resulting solution was washed with brine (2×100 mL) and deionized water (2×100 mL), dried over magnesium sulfate, filtered, concentrated under reduced pressure, and further dried on a vacuum pump for three days to provide 13.99 g of product.

Part B

Platinum on carbon (1.5 g of 5%) was added to a solution of tert-butyl 2-[(2-chloro-3-nitroquinolin-4-yl)amino]ethylcarbamate (13.99 g, 38.19 mmol) in acetonitrile (100 mL) in a Parr vessel. The mixture was placed under hydrogen pressure (30 psi, $2.1 \times 10^5$ Pa) for three hours and then filtered through a layer of CELITE filter agent. The filtrate was concentrated under reduced pressure and further dried overnight on a vacuum pump to provide 13.46 g of tert-butyl 2-[(3-amino-2-chloroquinolin-4-yl)amino]ethylcarbamate as a light brown solid.

Part C

Cyanogen bromide (4.6 g, 44 mmol) was added to a solution of tert-butyl 2-[(3-amino-2-chloroquinolin-4-yl)amino]ethylcarbamate (13.46 g, 39.96 mmol) in ethanol (140 mL), and the reaction was heated at reflux overnight. An analysis by LC/MS indicated the presence of starting material, and additional cyanogen bromide (1.25 g, 12.0 mmol) was added. The reaction was heated at reflux for an additional two hours, and the reaction was still incomplete. Additional cyanogen bromide (1.25 g, 12.0 mmol) was added, and the reaction was heated at reflux for two hours and allowed to cool to room temperature. Most of the solvent was removed under reduced pressure, and aqueous sodium hydroxide (700 mL of 2 N) was added. The mixture was stirred for 30 minutes, and the aqueous portion was decanted away. Ethyl acetate (500 mL) was added, and the mixture was stirred for 20 minutes. The ethyl acetate was then decanted away, and the residue was filtered. The filter cake was washed several times with diethyl ether (1 L total), and the resulting solid was stirred vigorously with diethyl ether (500 mL). The solid was collected by filtration and dried under vacuum overnight to provide 7.02 g of tert-butyl 2-(2-amino-4-chloro-1H-imidazo[4,5-c]quinolin-1-yl)ethylcarbamate as a reddish-brown solid.

Part D tert-Butyl 2-(2-amino-4-chloro-1H-imidazo[4,5-c]quinolin-1-yl)ethylcarbamate (3.5 g, 9.7 mmol) and ammonia (approximately 100 mL of a 7 N solution in methanol) were added to a pressure vessel, which was sealed and heated at 150° C. overnight. The volatiles were removed under reduced pressure, and the residue was purified by automated flash chromatography (silica cartridge, eluting with aqueous ammonium hydroxide:methanol:dichloromethane in a gradient from 0:0:100 to 1.5:28.5:70) to provide 840 mg of 1-(2-aminoethyl)-1H-imidazo[4,5-c]quinoline-2,4-diamine as a dark grey solid.

Part E

An acid chloride, sulfonyl chloride, isocyanate, or carbonyl chloride indicated in the table below (0.105 mmol, 1.05 equivalents) was added to a test tube containing a solution of N,N-diisopropylethylamine (35.3 µL, 0.203 mmol) and 1-(2-aminoethyl)-1H-imidazo[4,5-c]quinoline-2,4-diamine (24.4 mg, 0.100 mmol) in DMA (1 mL). The tube was then capped and vortexed for overnight at room temperature. Ammonium hydroxide (250 µL) was added to each tube, and the contents were vortexed overnight at room temperature. Two drops of water were added to the test tube, and the solvent was removed by vacuum centrifugation. The compounds were purified by reversed phase prep HPLC according to the method described in Examples 19-42, Part F. The table below shows the reagent used for each example, the structure of the resulting compound, and the observed accurate mass for the isolated trifluoroacetate salt.

Examples 149-171

| Example | Reagent | R | Measured Mass (M + H) |
|---|---|---|---|
| 149 | None | —H | 243.1341 |
| 150 | Acetyl chloride | —C(=O)CH₃ | 285.1453 |
| 151 | Methyl chloroformate | —C(=O)O—CH₃ | 301.1420 |
| 152 | Isobutyryl chloride | —C(=O)CH(CH₃)₂ | 313.1793 |
| 153 | Cyclopentanecarbonyl chloride | —C(=O)-cyclopentyl | 339.1931 |
| 154 | Benzoyl chloride | —C(=O)Ph | 347.1614 |
| 155 | 3-Chlorobenzoyl chloride | —C(=O)(3-Cl-Ph) | 381.1241 |

-continued

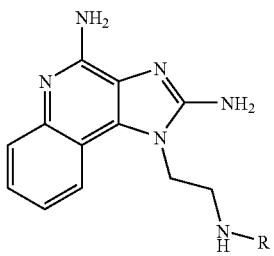

| Example | Reagent | R | Measured Mass (M + H) |
|---|---|---|---|
| 156 | Isonicotinoyl chloride hydrochloride | —C(=O)(4-pyridyl) | 348.1555 |
| 157 | Nicotinoyl chloride hydrochloride | —C(=O)(3-pyridyl) | 348.1588 |
| 158 | Picolinoyl chloride hydrochloride | —C(=O)(2-pyridyl) | 348.1595 |
| 159 | Methanesulfonyl chloride | —S(=O)₂CH₃ | 321.1143 |
| 160 | Ethanesulfonyl chloride | —S(=O)₂CH₂CH₃ | 335.1288 |
| 161 | Isopropylsulfonyl chloride | —S(=O)₂CH(CH₃)₂ | 349.1440 |
| 162 | Dimethylsulfamoyl chloride | —S(=O)₂N(CH₃)₂ | 350.1421 |
| 163 | 1-Methylimidazole-4-sulfonyl chloride | —S(=O)₂(1-methylimidazol-4-yl) | 387.1354 |

-continued

[Structure: 4-amino-2-amino-1H-imidazo[4,5-c]quinoline with 1-(2-(NHR)ethyl) substituent]

| Example | Reagent | R | Measured Mass (M + H) |
|---------|---------|---|------------------------|
| 164 | Methyl isocyanate | -C(=O)-NH-CH₃ | 300.1559 |
| 165 | Ethyl isocyanate | -C(=O)-NH-CH₂CH₃ | 314.1749 |
| 166 | Isopropyl isocyanate | -C(=O)-NH-CH(CH₃)₂ | 328.1905 |
| 167 | Phenyl isocyanate | -C(=O)-NH-phenyl | 362.1723 |
| 168 | N,N-Dimethylcarbamoyl chloride | -C(=O)-N(CH₃)₂ | 314.1714 |
| 169 | 1-Piperidinecarbonyl chloride | -C(=O)-piperidinyl | 354.2038 |
| 170 | 4-Morpholinylcarbonyl chloride | -C(=O)-morpholinyl | 356.1844 |

-continued

[Structure: 4-amino-2-amino-1H-imidazo[4,5-c]quinoline isomer with 1-(2-(NHR)ethyl) substituent]

| Example | Reagent | R | Measured Mass (M + H) |
|---------|---------|---|------------------------|
| 171 | 4-Methyl-1-piperazinecarbonyl chloride | -C(=O)-(4-methylpiperazinyl) | 369.2175 |

Examples 172-174

Part A

Triethylamine (5.24 g, 51.8 mmol) and benzylamine (4.15 mL, 38.0 mmol) were sequentially added to a solution of 7-bromo-4-chloro-3-nitroquinoline (10.0 g, 34.5 mmol, see U.S. Patent Publication Application No. US 2004/0147543 (Hays et al.), Example 1 Parts A through D) in DMF (100 mL). The reaction was stirred at room temperature for three days, poured into water (800 mL), and stirred vigorously for 20 minutes. A precipitate formed and was isolated by filtration, washed with diethyl ether (800 mL), and dried under vacuum for four hours to provide 10.98 g of N-benzyl-7-bromo-3-nitroquinolin-4-amine as a yellow solid.

Part B

Platinum on carbon (1.2 g of 5%) was added to a solution of N-benzyl-7-bromo-3-nitroquinolin-4-amine (10.9 g, 30.4 mmol) in acetonitrile (300 mL) in a Parr vessel. The mixture was placed under hydrogen pressure (30 psi, $2.1 \times 10^5$ Pa) overnight and then filtered through a layer of CELITE filter agent. The filter cake was washed with methanol. The filtrate was concentrated under reduced pressure and further dried for two hours on a vacuum pump to provide 6.33 g of $N^4$-benzyl-7-bromoquinoline-3,4-diamine as a dark green solid.

Part C

Cyanogen bromide (3.4 g, 10.3 mmol) was added to a solution of the material from Part B in ethanol (100 mL), and the reaction was heated at reflux overnight and allowed to cool to room temperature. Aqueous sodium hydroxide (6 M) was added to adjust the reaction to pH 11. The solvent was removed under reduced pressure, and ethyl acetate (200 mL) and deionized water (150 mL) were added. The mixture was stirred for 30 minutes. The aqueous layer was separated and extracted with ethyl acetate (2×150 mL). The combined organic fractions were washed with aqueous sodium hydroxide (300 mL of 2 M), dried over magnesium sulfate, filtered, and concentrated under reduced pressure. The residue (4.6 g) was purified by automated flash chromatography (silica cartridge, eluting with aqueous ammonium hydroxide:methanol:dichloromethane in a gradient from 0:0:100 to 0.7:14.3:85) to provide 2.91 g of 1-benzyl-7-bromo-1H-imidazo[4,5-c]quinolin-2-amine as a light brown solid.

Part D

3-Chloroperoxybenzoic acid (3.7 g of approximately 77% pure material) was added to a solution of 1-benzyl-7-bromo- 1H-imidazo[4,5-c]quinolin-2-amine (2.91 g, 8.24 mmol), and the reaction was stirred for two hours at room temperature. Concentrated aqueous ammonium hydroxide (50 mL) and p-toluenesulfonyl chloride (3.1 g, 16 mmol) were added, and the mixture was stirred overnight at room temperature. The organic layer was separated and washed with water (3×200 mL), dried over magnesium sulfate, filtered, and concentrated under reduced pressure. The crude product (1.88 g) was purified by automated flash chromatography (silica cartridge, eluting with aqueous ammonium hydroxide:methanol:dichloromethane in a gradient from 0:0:100 to 0.55:10.45:89) to provide 123 g of 1-benzyl-7-bromo-1H-imidazo[4,5-c]quinolin-2,4-diamine as a reddish-brown solid.

MS (ESI) calcd. for $C_{17}H_{14}BrN_5$ 368.0519 (M+H). Found: 368.0511.

Part E

A solution of 1-benzyl-7-bromo-1H-imidazo[4,5-c]quinolin-2,4-diamine (26.7 mg, 0.072 mmol) in 7:3 volume:volume (v:v) chloroform:methanol (2 mL) was added to a test tube, and the solvent was removed by vacuum centrifugation. The boronic acid (0.08 mmol) indicated in the table below and n-propanol (1.6 mL) were sequentially added, and the test tube was purged with nitrogen. Palladium (II) acetate (0.150 mL of a 4 mg/mL solution in toluene, 0.0027 mmol), 2 M aqueous sodium carbonate solution (600 µL), deionized water (113 µL), and a solution of 0.15 mol % triphenylphosphine in n-propanol (53 µL, 0.0078 mmol) were sequentially added. The test tube was purged with nitrogen, capped, and then heated at 80° C. overnight in a sand bath.

The contents of each test tube were passed through a Waters Oasis Sample Extractions Cartridge MCX (6 cc) according to the following procedure. Hydrochloric acid (3 mL of 1 N in methanol) was added to adjust each example to pH 5-7, and the resulting solution was passed through the cartridge optionally using light nitrogen pressure. The cartridge was washed with methanol (5 mL) optionally using light nitrogen pressure and transferred to a clean test tube. A solution of 1% ammonia in methanol (2×5 mL) was then passed through the cartridge optionally using light nitrogen pressure, and the basic solution was collected and concentrated by vacuum centrifugation. The compounds were purified by reversed phase prep HPLC using the method described in Examples 19-42, Part F. The table below shows the boronic acid added to each test tube, the structure of the resulting compound, and the observed accurate mass for the isolated trifluoroacetate salt.

Examples 172-174

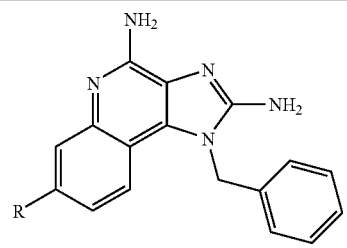

| Example | Reagent | R | Measured Mass (M + H) |
|---|---|---|---|
| 172 | None | Br– | 368.0505 |

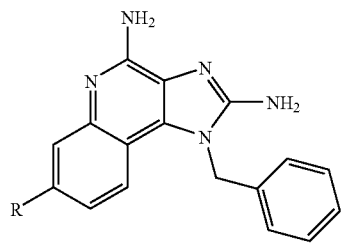

| Example | Reagent | R | Measured Mass (M + H) |
|---|---|---|---|
| 173 | Phenylboronic acid | phenyl | 366.1742 |
| 174 | Pyridine-3-boronic acid | pyridin-3-yl | 367.1689 |

Examples 175-180

Part A

1-Amino-2-methylpropan-2-ol (575 mg, 6.45 mmol) and triethylamine (889 mg, 8.79 mmol) were added to a solution of 7-bromo-2,4-dichloro-3-nitroquinoline (1.9 g, 5.9 mmol) in DMF (25 mL), and the reaction was stirred at room temperature for two hours and poured into water (750 mL). A precipitate formed and was isolated by filtration, washed with water (500 mL), and dried under vacuum for two hours to provide 1.94 g of 1-[(7-bromo-2-chloro-3-nitroquinolin-4-yl)amino]-2-methylpropan-2-ol as a yellow solid.

Part B

Platinum on carbon (0.2 g of 5%) was added to a solution of 1-[(7-bromo-2-chloro-3-nitroquinolin-4-yl)amino]-2-methylpropan-2-ol (1.94 g, 5.16 mmol) in acetonitrile in a Parr vessel. The mixture was placed under hydrogen pressure (40 psi, $2.8 \times 10^5$ Pa) for two hours and then filtered through a layer of CELITE filter agent. The filter cake was washed with methanol. The filtrate was concentrated under reduced pressure to provide 1.5 g of 1-[(3-amino-7-bromo-2-chloroquinolin-4-yl)amino]-2-methylpropan-2-ol as an oil.

Part C

A suspension of 1-[(3-amino-7-bromo-2-chloroquinolin-4-yl)amino]-2-methylpropan-2-ol (1.5 g, 4.35 mmol) in ethanol (25 mL) was heated to 80° C. Cyanogen bromide (0.50 g, 4.8 mmol) was added to the resulting solution, and the reaction was heated at 80° C. overnight and allowed to cool. A precipitate was present and was isolated by filtration, washed with diethyl ether, and dried under vacuum for one hour to provide 1.34 g of 1-(2-amino-7-bromo-4-chloro-1H-imidazo[4,5-c]quinolin-1-yl)-2-methylpropan-2-ol hydrobromide as a pinkish-white solid, mp >260° C.

Anal. calcd. for $C_{14}H_{14}BrClN_4O \cdot 1.0HBr$: C, 37.32; H, 3.36; N, 12.23. Found: C, 37.58; H, 3.15; N, 12.40.

Part D 1-(2-Amino-7-bromo-4-chloro-1H-imidazo[4,5-c]quinolin-1-yl)-2-methylpropan-2-ol hydrobromide (1.18 g, 3.19 mmol) and ammonia (50 mL of a 7 N solution in methanol) were added to a pressure vessel, which was sealed and heated at 140° C. for five days. Additional ammonia in methanol was added after two days. When the reaction was complete, the volatiles were removed under reduced pressure, and the residue was stirred with aqueous sodium hydroxide (100 mL of 2

N) for 15 minutes. A solid was present and was isolated by filtration, washed with water and diethyl ether, and dried under vacuum to provide 681 mg of 1-(2,4-diamino-7-bromo-1H-imidazo[4,5-c]quinolin-1-yl)-2-methylpropan-2-ol as a gray solid.

Part E

The methods of Examples 172-174, Part E were followed using 1-(2,4-diamino-7-bromo-1H-imidazo[4,5-c]quinolin-1-yl)-2-methylpropan-2-ol (35.7 mg, 0.10 mmol) in lieu of 7-bromo-1-benzyl-1H-imidazo[4,5-c]quinolin-2,4-diamine with the modification that after the reaction was heated overnight, methanol (1 mL) and additional palladium (II) acetate (0.150 mL of a 4 mg/mL solution in toluene, 0.0027 mmol) were added to each tube. The reaction was heated at 80° C. for an additional five hours. The table below shows the boronic acid added to each test tube, the structure of the resulting compound, and the observed accurate mass for the isolated trifluoroacetate salt.

Examples 175-180

Example 181

Methyl [4-amino-1-(2-hydroxy-2-methylpropyl)-1H-imidazo[4,5-c]quinolin-2-yl]carbamate

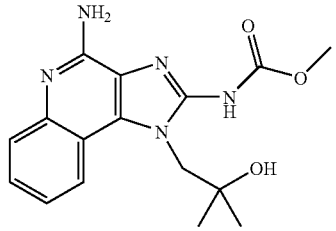

Part A

A mixture of 1-[(3-amino-4-quinolinyl)amino]-2-methyl-2-propanol (1.0 g, 4.3 mmol), 1,3-dimethoxycarbonyl-O-methylisourea (prepared according to the general method of Viswanathan, N. Indian Patent No. 168,784, 1.64 g, 8.64 mmol), acetic acid (1.3 g, 22 mmol), and p-toluenesulfonic

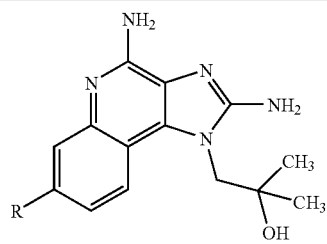

| Example | Reagent | R | Measured Mass (M + H) |
|---|---|---|---|
| 175 | None | Br— | 350.0601 |
| 176 | Pyridine-3-boronic acid | 3-pyridyl | 349.1752 |
| 177 | 4-(Hydroxymethyl)phenylboronic acid | 4-(HOCH$_2$)C$_6$H$_4$— | 378.1920 |
| 178 | 4-Methoxyphenylboronic acid | 4-(CH$_3$O)C$_6$H$_4$— | 378.1918 |
| 179 | 3-Chlorophenylboronic acid | 3-Cl-C$_6$H$_4$— | 382.1423 |
| 180 | 4-Chlorophenylboronic acid | 4-Cl-C$_6$H$_4$— | 382.1434 | acid (0.82 g, 4.3 mmol) in methanol (20 mL) was heated at reflux for 16 hours. The volatiles were removed under reduced pressure, and the residue was dissolved in chloroform (100 mL). The solution was washed sequentially with water (100 mL), aqueous sodium carbonate (100 mL of 4% w/w), water (100 mL), and brine (100 mL) and then concentrated under reduced pressure. The residue was purified by automated flash chromatography (40+M silica cartridge, eluting with 0% to 25% CMA in chloroform) followed by recrystallization from acetonitrile to provide 0.64 g of methyl [1-(2-hydroxy-2-methylpropyl)-1H-imidazo[4,5-c]quinolin-2-yl]carbamate as a white solid, mp 225° C.

MS (APCI) m/z 315.14 (M+H)$^+$;

Anal. calcd. for $C_{16}H_{18}N_4O_3$: C, 61.14; H, 5.77; N, 17.82. Found: C, 61.10; H, 5.61; N, 17.96.

Part B

3-Chloroperoxybenzoic acid (1.83 g of approximately 75% pure material) was added to a stirred solution of methyl [1-(2-hydroxy-2-methylpropyl)-1H-imidazo[4,5-c]quinolin-2-yl]carbamate (1.0 g, 3.18 mmol) in dichloromethane (25 mL), and the reaction was stirred for 24 hours at room temperature. A precipitate formed and was collected by filtration, washed with a minimal amount of dichloromethane, and dried to provide 0.8 g of methyl [1-(2-hydroxy-2-methylpropyl)-5-oxido-1H-imidazo[4,5-c]quinolin-2-yl]carbamate as a solid.

MS (ESI) m/z 331.26 (M+H)$^+$.

Part C

A suspension of methyl [1-(2-hydroxy-2-methylpropyl)-5-oxido-1H-imidazo[4,5-c]quinolin-2-yl]carbamate (0.80 g, 2.4 mmol) in methanol (10 mL) was stirred vigorously and cooled to 0° C. Concentrated ammonium hydroxide (0.8 mL, 25 mmol) was added followed by benzenesulfonyl chloride (0.9 g, 5 mmol), which was added dropwise. The mixture was stirred for two hours at 0° C. to 5° C. An analysis by LC/MS indicated the reaction was incomplete. Additional benzenesulfonyl chloride (0.9 g) was added, and the reaction mixture was stirred overnight at room temperature. The solvent was removed under reduced pressure, and the residue was purified by automated flash chromatography (40+M silica cartridge, eluting with 0% to 25% CMA in chloroform) followed by recrystallization from ethyl acetate to provide 0.36 g of methyl [4-amino-1-(2-hydroxy-2-methylpropyl)-1H-imidazo[4,5-c]quinolin-2-yl]carbamate as a white solid, mp 255-258° C. (decomposition).

MS (ESI) m/z 330.33 (M+H)$^+$;

Anal. calcd. for $C_{16}H_{19}N_5O_3 \cdot 0.3H_2O$: C, 57.41; H, 5.90; N, 20.92. Found: C, 57.64; H, 6.11; N, 20.91.

Example 182

Methyl [4-amino-1-(2-methylpropyl)-1H-imidazo[4,5-c][1,5]naphthyridin-2-yl]carbamate

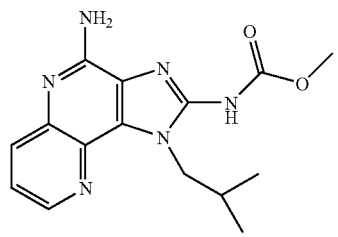

Part A

A mixture of $N^4$-(2-methylpropyl)[1,5]naphthyridine-3,4-diamine (Gerster et al, U.S. Pat. No. 6,194,425, Example 30 Part A, 4.10 g, 19.0 mmol), 1,3-dimethoxycarbonyl-O-methylisourea (7.21 g, 37.9 mmol), acetic acid (5.69 g, 94.8 mmol), and p-toluenesulfonic acid (3.60 g, 19.0 mmol) in methanol (50 mL) was heated at reflux for 16 hours. The volatiles were removed under reduced pressure, and the residue was dissolved in chloroform (150 mL). The solution was washed sequentially with water (150 mL), aqueous sodium carbonate (150 mL of 4% w/w), water (150 mL), and brine (150 mL) and then concentrated under reduced pressure. The residue was purified by automated flash chromatography (40+M silica cartridge, eluting with 0% to 20% CMA in chloroform) followed by recrystallization from acetonitrile to provide 1.78 g of methyl [1-(2-methylpropyl)-1H-imidazo[4,5-c][1,5]naphthyridin-2-yl]carbamate as a white solid, mp 195-197° C.

MS (ESI) m/z 300.29 (M+H)$^+$;

Anal. calcd. for $C_{15}H_{17}N_5O_2$: C, 60.19; H, 5.72; N, 23.40. Found: C, 60.03; H, 5.49; N, 23.38.

Part B

3-Chloroperoxybenzoic acid (1.73 g of approximately 75% pure material) was added to a stirred solution of methyl [1-(2-methylpropyl)-1H-imidazo[4,5-c][1,5]naphthyridin-2-yl]carbamate (1.5 g, 5.01 mmol) in dichloromethane (40 mL), and the reaction was stirred for 76 hours at room temperature. A precipitate formed and was collected by filtration, washed with a minimal amount of dichloromethane, and dried to provide 0.9 g of methyl [1-(2-methylpropyl)-5-oxido-1H-imidazo[4,5-c][1,5]naphthyridin-2-yl]carbamate as a solid.

MS (ESI) m/z 316.29 (M+H)$^+$.

Part C

A suspension of methyl [1-(2-methylpropyl)-5-oxido-1H-imidazo[4,5-c][1,5]naphthyridin-2-yl]carbamate (0.9 g, 3 mmol) in methanol (25 mL) was stirred vigorously and heated to 50° C. Concentrated ammonium hydroxide (0.95 mL, 14 mmol) was added followed by benzenesulfonyl chloride (1.06 g, 5.99 mmol), which was added dropwise. The mixture was stirred for two hours at 50° C. An analysis by LC/MS indicated the reaction was incomplete. Additional benzenesulfonyl chloride (1.06 g) and concentrated ammonium hydroxide (0.95 mL) were added, and the reaction mixture was stirred overnight at 45° C. The solvent was removed under reduced pressure, and the residue dissolved in chloroform (100 mL). The solution was washed sequentially with aqueous sodium carbonate (2×100 mL of 4% w/w) and water (100 mL) and then purified by automated flash chromatography (40+M silica cartridge, eluting with 5% to 25% CMA in chloroform) followed by recrystallization from ethyl acetate to provide 0.28 g of methyl [4-amino-1-(2-methylpropyl)-1H-imidazo[4,5-c][1,5]naphthyridin-2-yl]carbamate as a yellow solid.

MS (APCI) m/z 315.19 (M+H)$^+$;

$^1$HNMR (300 MHz, DMSO) δ 10.09 (bs, 1H), 8.52 (d, J=2.8 Hz, 1H), 7.90 (d, J=7.7 Hz, 1H), 7.47 (dd, J=8.5, 3.2 Hz, 1H), 6.79 (br s, 2H), 4.54 (d, J=7.3 Hz, 2H), 3.72 (s, 3H), 2.25 (m, 1H), 0.86 (m, 6H).

Exemplary Compounds

Certain exemplary compounds, including some of those described above in the Examples, have one of the following Formulas (IVa, Va, VIa, IVb, or VIb) and an $R_1$ substituent shown in the following table, wherein each line of the table is matched with a Formula (IVa, Va, VIa, IVb, or VIb) to represent a specific embodiment of the invention.

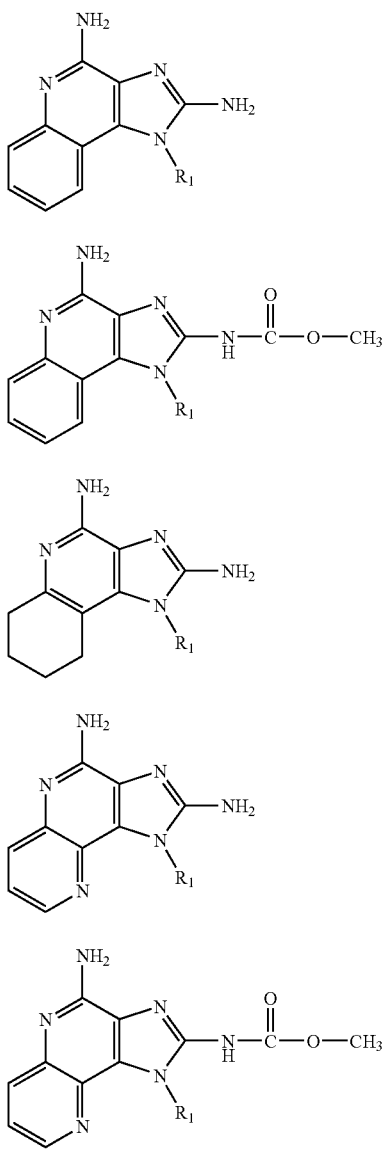

| R₁ |
|---|
| 2-methylpropyl |
| 2-hydroxy-2-methylpropyl |
| 2-methyl-2-[(methylsulfonyl)amino]propyl |
| 2-[(cyclohexylcarbonyl)amino]-2-methylpropyl |
| 4-[(methylsulfonyl)amino]butyl |
| 4-(acetylamino)butyl |
| 4-[(morpholin-4-ylcarbonyl)amino]butyl |
| 2,2-dimethyl-4-oxopentyl |
| 2-(4-methylpiperazin-1-yl)ethyl |
| [1-(methylsulfonyl)piperidin-4-yl]methyl |
| (1-hydroxycyclobutyl)methyl |
| (1-acetylpiperidin-4-yl)methyl |
| 2-(4-acetylpiperazin-1-yl)ethyl |
| 2-[4-(methylsulfonyl)piperazin-1-yl]ethyl |
| tetrahydro-2H-pyran-4-ylmethyl |

Certain exemplary compounds, including some of those described above in the Examples, have one of the following Formulas (IVc, Vb, or VIc) and an $R_2$ substituent shown in the following table, wherein each line of the table is matched with a Formula (IVc, Vb, or VIc) to represent a specific embodiment of the invention.

| $R_2$ |
|---|
| methyl |
| ethyl |
| 2-methoxyethyl |
| 3-methoxypropyl |
| 2-hydroxyethyl |
| 3-hydroxypropyl |

Certain exemplary compounds, including some of those described above in the Examples, have one of the following Formulas (IVd or VId) and an $R_1$ substituent shown in the following table, wherein each line of the table is matched with a Formula (IVd or VId) to represent a specific embodiment of the invention.

| R₁ |
| --- |
| benzyl |
| 4-fluorobenzyl |
| 2,4-difluorobenzyl |
| 3,4-difluorobenzyl |
| 4-(trifluoromethyl)benzyl |

Compounds of the invention have been found to modulate cytokine biosynthesis by inducing the production of interferon a and/or tumor necrosis factor α when tested using one of the methods described below. Particular examples include, but are not limited to, the compounds of Examples 1-4, 8, 10, 12-14, 18-23, 25-28, 31, 32, 34-37, 41-45, 49-52, 54-56, 62-64, 67, 71, 73, 76, 83, 107, 131-133, 140, 141, 145, 147, 150, 151, 153-155, 157, 158, 161, 163, 168, 169, 171, and 172.

Cytokine Induction in Human Cells

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION IN HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 µM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 µM) than the final tested concentration range.

Incubation

Compound solution is then added to the wells containing the PBMC suspension bringing the test compound concentrations to the desired range (usually 30-0.014 µM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-αF (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Certain compounds of the invention modulate cytokine biosynthesis by inhibiting production of tumor necrosis factor α (TNF-α) when tested using the method described below. Particular examples, include but are not limited to, the compounds of Examples 7, 8, and 9.

TNF-α Inhibition in Mouse Cells

The mouse macrophage cell line Raw 264.7 is used to assess the ability of compounds to inhibit tumor necrosis factor-α (TNF-α) production upon stimulation by lipopolysaccharide (LPS).

Single Concentration Assay:

Blood Cell Preparation for Culture

Raw cells (ATCC) are harvested by gentle scraping and then counted. The cell suspension is brought to $3 \times 10^5$ cells/mL in RPMI with 10% fetal bovine serum (FBS). Cell suspension (100 µL) is added to 96-well flat bottom sterile tissues culture plates (Becton Dickinson Labware, Lincoln Park, N.J.). The final concentration of cells is $3 \times 10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from *Salmonella typhimurium*, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:

Blood Cell Preparation for Culture

Raw cells (ATCC) are harvested by gentle scraping and then counted. The cell suspension is brought to $4 \times 10^5$ cells/mL in RPMI with 10% FBS. Cell suspension (250 μL) is added to 48-well flat bottom sterile tissues culture plates (Costar, Cambridge, Mass.). The final concentration of cells is $1 \times 10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from *Salmonella typhimurium*, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of the following Formula II:

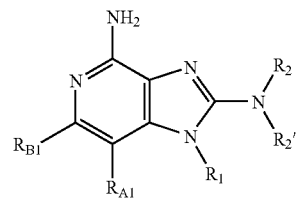

wherein:
$R_2$ and $R_2'$ are independently selected from the group consisting of hydrogen, $C_{1-4}$ alkyl, hydroxy$C_{2-4}$ alkylenyl, and alkoxy$C_{2-4}$ alkylenyl;

$R_{A1}$ and $R_{B1}$ taken together form a fused benzene ring wherein the benzene ring is unsubstituted or substituted by one $R_3$ group, or substituted by one $R_3$ group and one R group, or substituted by one or more R groups;

or $R_{A1}$ and $R_{B1}$ taken together form a fused 5 to 7 membered saturated, carbocyclic ring wherein the ring is unsubstituted or substituted by one or more R groups;

R is selected from the group consisting of halogen, hydroxy, alkyl, alkenyl, haloalkyl, alkoxy, alkylthio, and —N($R_9$)$_2$;

$R_1$ is selected from the group consisting of:
hydrogen, alkyl, arylalkylenyl, hydroxyalkyl, dihydroxyalkyl, haloalkyl,
—$X_1$—$Y_1$—$R_4'$,
—$X_1$—$Y_1$—$X_1'$—$Y_1'$—$R_4'$, and
—$X_1$—$R_5'$;

$X_1$ is alkylene;
$X_1'$ is $C_{1-4}$ alkylene or phenylene;
$Y_1$ is —N($R_8$)—C(O)—, —N($R_8$)—S(O)$_2$—, —N($R_8$)—C($R_6$)—N($R_8$)—, —N($R_8$)—C($R_6$)—N($R_8$)—C(O)—, or —N($R_8$)—C($R_6$)—O—;
$Y_1'$ is —S—, —NHC(O)—, —C(O)—O—, or —C(O)—;
$R_4'$ is alkyl, aryl, heteroaryl, heterocyclyl, arylalkylenyl, heteroarylalkylenyl, or arylalkenylenyl, wherein alkyl, aryl, heteroaryl, heterocyclyl, or arylalkylenyl is optionally substituted by one or more substituents independently selected from the group consisting of alkyl, halogen, haloalkyl, haloalkoxy, heterocyclyl, cyano, alkoxy, dialkylamino, and, in the case of alkyl or heterocyclyl, oxo;
$R_5'$ is

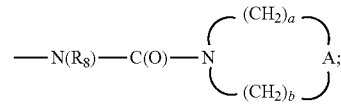

$R_3$ is
—Z—$R_4$,
Z is selected from the group consisting of a bond and —O—;
$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

A is selected from the group consisting of —O—, —C(O)—, —S(O)$_{0-2}$—, and —N(R$_4$)—;

a and b are independently integers from 1 to 6 with the proviso that a+b is $\leq$7;

R$_6$ is selected from the group consisting of =O and =S;

R$_8$ is selected from the group consisting of hydrogen, alkyl, alkoxyalkylenyl, and arylalkylenyl; and R$_9$ is selected from the group consisting of hydrogen and alkyl;

or a pharmaceutically acceptable salt thereof.

2. A compound of the following Formula IV:

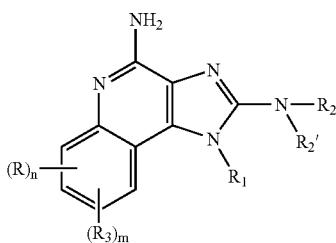

IV wherein:

R$_2$ and R$_2$' are independently selected from the group consisting of hydrogen, C$_{1-4}$ alkyl, hydroxyC$_{2-4}$ alkylenyl, and alkoxyC$_{2-4}$ alkylenyl;

R is selected from the group consisting of halogen, hydroxy, alkyl, alkenyl, haloalkyl, alkoxy, alkylthio, and —N(R$_9$)$_2$;

R$_1$ is selected from the group consisting of:
hydrogen, alkyl, arylalkylenyl, hydroxyalkyl, dihydroxyalkyl, haloalkyl,
—X$_1$—Y$_1$—R$_4$',
—X$_1$—Y$_1$—X$_1$'—Y$_1$'—R$_4$', and
—X$_1$—R$_5$';

X$_1$ is alkylene;

X$_1$' is C$_{1-4}$ alkylene or phenylene;

Y$_1$ is —N(R$_8$)—C(O)—, —N(R$_8$)—S(O)$_2$—, —N(R$_8$)—C(R$_6$)—N(R$_8$)—, —N(R$_8$)—C(R$_6$)—N(R$_8$)—C(O)—, or —N(R$_8$)—C(R$_6$)—O—;

Y$_1$' is —S—, —NHC(O)—, —C(O)—O—, or —C(O)—;

R$_4$' is alkyl, aryl, heteroaryl, heterocyclyl, arylalkylenyl, heteroarylalkylenyl, or arylalkenylenyl, wherein alkyl, aryl, heteroaryl, heterocyclyl, or arylalkylenyl is optionally substituted by one or more substituents independently selected from the group consisting of alkyl, halogen, haloalkyl, haloalkoxy, heterocyclyl, cyano, alkoxy, dialkylamino, and, in the case of alkyl or heterocyclyl, oxo;

R$_5$' is

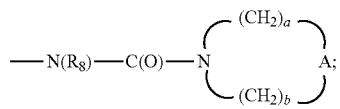

R$_3$ is
—Z—R$_4$,

Z is selected from the group consisting of a bond and —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

A is selected from the group consisting of —O—, —C(O)—, —S(O)$_{0-2}$—, and —N(R$_4$)—;

a and b are independently integers from 1 to 6 with the proviso that a+b is $\leq$7;

n is an integer from 0 to 4;

m is 0 or 1, with the proviso that when m is 1, n is 0 or 1;

R$_6$ is selected from the group consisting of =O and =S;

R$_8$ is selected from the group consisting of hydrogen, alkyl, alkoxyalkylenyl, and arylalkylenyl; and R$_9$ is selected from the group consisting of hydrogen and alkyl;

or a pharmaceutically acceptable salt thereof.

3. The compound or salt of claim 2 wherein m is 0, and n is 0.

4. The compound or salt of claim 1 wherein R$_1$ is hydrogen.

5. The compound or salt of claim 1 wherein R$_1$ is selected from the group consisting of alkyl, hydroxyalkyl, dihydroxyalkyl, haloalkyl, —X$_1$—Y$_1$—R$_4$', and —X$_1$—R$_5$'; wherein X$_1$ is alkylene, Y$_1$ is —N(R$_8$)—C(O)—, —N(R$_8$)—S(O)$_2$—, —N(R$_8$)—C(R$_6$)—N(R$_8$)—, or —N(R$_8$)—C(R$_6$)—O—; R$_4$ is alkyl, aryl, heteroaryl, arylalkylenyl, heteroarylalkylenyl, or arylalkenylenyl, wherein alkyl, aryl, heteroaryl, or arylalkylenyl is optionally substituted by one or more substituents independently selected from the group consisting of alkyl, halogen, haloalkyl, haloalkoxy, heterocyclyl, cyano, alkoxy, and dialkylamino; and R$_5$ is

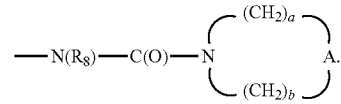

6. The compound or salt of claim 5 wherein R$_1$ is selected from the group consisting of 2-hydroxy-2-methylpropyl, 2-methylpropyl, 2-fluoro-2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, 2-[(cyclohexylcarbonyl)amino]-2-methylpropyl, and (1-hydroxycyclobutyl)methyl.

7. The compound or salt of claim 1 wherein R$_2$ is hydrogen and R$_2$' is selected from the group consisting of hydrogen, C$_{1-4}$ alkyl, C$_{1-4}$ alkoxyC$_{2-4}$ alkylenyl, and hydroxyC$_{2-4}$ alkylenyl.

8. The compound or salt of claim 7 wherein R$_2$ is hydrogen, and R$_2$' is hydrogen.

9. A pharmaceutical composition comprising a therapeutically effective amount of a compound or salt of claim 1 in combination with a pharmaceutically acceptable carrier.

10. A method of inducing biosynthesis of at least one of interferon-alpha or tumor necrosis factor-alpha in an animal comprising administering an effective amount of a compound or salt of claim 1 to the animal.

11. The compound or salt of claim 2 wherein $R_1$ is hydrogen.

12. The compound or salt of claim 2 wherein $R_1$ is selected from the group consisting of alkyl, hydroxyalkyl, dihydroxyalkyl, haloalkyl, —$X_1$—$Y_1$—$R_4'$, and —$X_1$—$R_5'$; wherein $X_1$ is alkylene, $Y_1$ is —N($R_8$)—C(O)—, —N($R_8$)—S(O)$_2$—, —N($R_8$)—C($R_6$)—N($R_8$)—, or —N($R_8$)—C($R_6$)—O—; $R_4$ is alkyl, aryl, heteroaryl, arylalkylenyl, heteroarylalkylenyl, or arylalkenylenyl, wherein alkyl, aryl, heteroaryl, or arylalkylenyl is optionally substituted by one or more substituents independently selected from the group consisting of alkyl, halogen, haloalkyl, haloalkoxy, heterocyclyl, cyano, alkoxy, and dialkylamino; and $R_5$ is

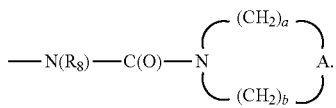

13. The compound or salt of claim 12 wherein $R_1$ is selected from the group consisting of 2-hydroxy-2-methylpropyl, 2-methylpropyl, 2-fluoro-2-methylpropyl, 4-[(methylsulfonyl)amino]butyl, 2-methyl-2-[(methylsulfonyl)amino]propyl, 3-(acetylamino)propyl, 4-(acetylamino)butyl, 4-[(morpholin-4-ylcarbonyl)amino]butyl, 3-(isobutyrylamino)propyl, 2-[(cyclohexylcarbonyl)amino]-2-methylpropyl, and (1-hydroxycyclobutyl)methyl.

14. The compound or salt of claim 2 wherein $R_2$ is hydrogen and $R_2'$ is selected from the group consisting of hydrogen, $C_{1-4}$ alkyl, $C_{1-4}$alkoxy$C_{2-4}$ alkylenyl, and hydroxy$C_{2-4}$ alkylenyl.

15. The compound or salt of claim 14 wherein $R_2$ is hydrogen, and $R_2'$ is hydrogen.

16. A pharmaceutical composition comprising a therapeutically effective amount of a compound or salt of claim 2 in combination with a pharmaceutically acceptable carrier.

17. A method of inducing biosynthesis of at least one of interferon-alpha or tumor necrosis factor-alpha in an animal comprising administering an effective amount of a compound or salt of claim 2 to the animal.

18. The compound or salt of claim 1 wherein $R_1$ is benzyl.

19. The compound or salt of claim 2 wherein $R_1$ is benzyl.

* * * * *